(12) United States Patent
Cho et al.

(10) Patent No.: US 7,179,964 B2
(45) Date of Patent: *Feb. 20, 2007

(54) TRANSGENIC PLANTS WITH ELEVATED THIOREDOXIN LEVELS

(75) Inventors: Myeong-Je Cho, Alameda, CA (US); Joshua H. Wong, San Francisco, CA (US); Peggy G. Lemaux, Moraga, CA (US); Bob B. Buchanan, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 499 days.

This patent is subject to a terminal disclaimer.

(21) Appl. No.: 10/194,885

(22) Filed: Jul. 12, 2002

(65) Prior Publication Data

US 2003/0135878 A1    Jul. 17, 2003

Related U.S. Application Data

(63) Continuation-in-part of application No. 09/538,864, filed on Mar. 29, 2000, now Pat. No. 6,784,346.

(60) Provisional application No. 60/307,006, filed on Jul. 19, 2001.

(51) Int. Cl.
C12N 15/82 (2006.01)
A01H 5/00 (2006.01)

(52) U.S. Cl. ............ 800/298; 800/287; 800/320.1; 800/290; 800/306; 800/284

(58) Field of Classification Search ........ 800/298, 800/278, 290, 284, 320.1, 306; 435/468, 435/101

See application file for complete search history.

(56) References Cited

U.S. PATENT DOCUMENTS

| 5,543,576 A | 8/1996 | van Ooijen et al. |
| 5,569,833 A | 10/1996 | Vincentz et al. |
| 5,792,506 A | 8/1998 | Buchanan et al. |
| 5,889,189 A | 3/1999 | Rodriguez |
| 5,952,034 A | 9/1999 | Buchanan et al. |
| 6,113,951 A | 9/2000 | Buchanan et al. |
| 6,114,504 A | 9/2000 | Buchanan et al. |
| 6,190,723 B1 | 2/2001 | Buchanan et al. |
| 6,380,372 B1* | 4/2002 | Cho et al. ............. 536/23.1 |
| 6,784,346 B1* | 8/2004 | Cho et al. ............. 800/320 |
| 2003/0145347 A1* | 7/2003 | Lanahan et al. ........ 800/278 |

FOREIGN PATENT DOCUMENTS

| WO | WO 96/03505 | 2/1996 |
| WO | WO 00/36126 | 6/2000 |
| WO | WO 01/98509 A2 | 12/2001 |

OTHER PUBLICATIONS

Brugidou et al (1993, Mol. Gen. Genet. 238:285-293).*
Wong et al (1995, Plant Physiology 108(2) SUPPL.:67).*
Cho, M.J. et al. (1998) "Subcellular Targeting of Barley Hordein Promoter-uidA Fusions in Transgenic Barley Seed" *In Vitro Cellular and Developmental Biology* 34(3) part 2:48A. Abstract only.
Gautier et al. (1998) "Characterization of wheat thioredoxin *h* cDNA and production of an active *Triticum aestivum* protein in *Escherichia coli*" *European Journal of Biochemistry* 252: 314-324.
Ishiwatari et al. (1996) *Plant* 195 (3): 456-463.
Rivera-Madrid et al. (Jun. 1995) *PNAS USA* 92: 5620-5624.
Sewalt et al. (1997) *J. Agric. food Chem.*, 45: 1977-1983.
Shi et al. (1996) *Plant Molecular Biology* 32: 653-662.
Dai, Shaodong et al. (1996) "Crystal Structure of *Arabidopsis thaliana* NADPH Dependent Thioredoxin Reductase at 2.5 A Resolution" J. Mol. Biol. 264: 1044-1057.
Jacquot, Jean-Pierre et al. (1994) "*Arabidopsis thaliana* NAPHP Thioredoxin Redutase" J. M. I. Biol. 235: 1357-1363.

* cited by examiner

*Primary Examiner*—Stuart F. Baum
(74) *Attorney, Agent, or Firm*—Morrison & Foerster LLP

(57) ABSTRACT

The present invention is directed to a transgenic plant wherein at least a part of said plant includes a recombinant nucleic acid with a promoter active in the part operably linked to a nucleic acid encoding a thioredoxin polypeptide wherein the promoter is a seed or grain maturation-specific promoter and the thioredoxin polypeptide includes the amino acid sequence WCGPC. The present invention is further directed to transgenic plants that overexpress thioredoxin in seed wherein the overexpression of thioredoxin h effects a significant increase in the reduction of proteins (—SH as compared to S—S) of the albumin fraction of the seed.

15 Claims, 32 Drawing Sheets

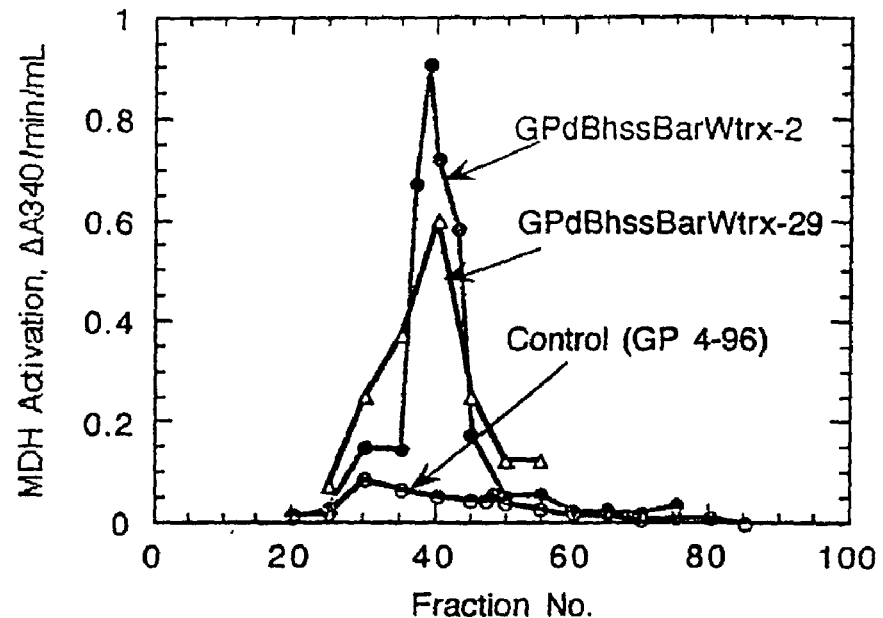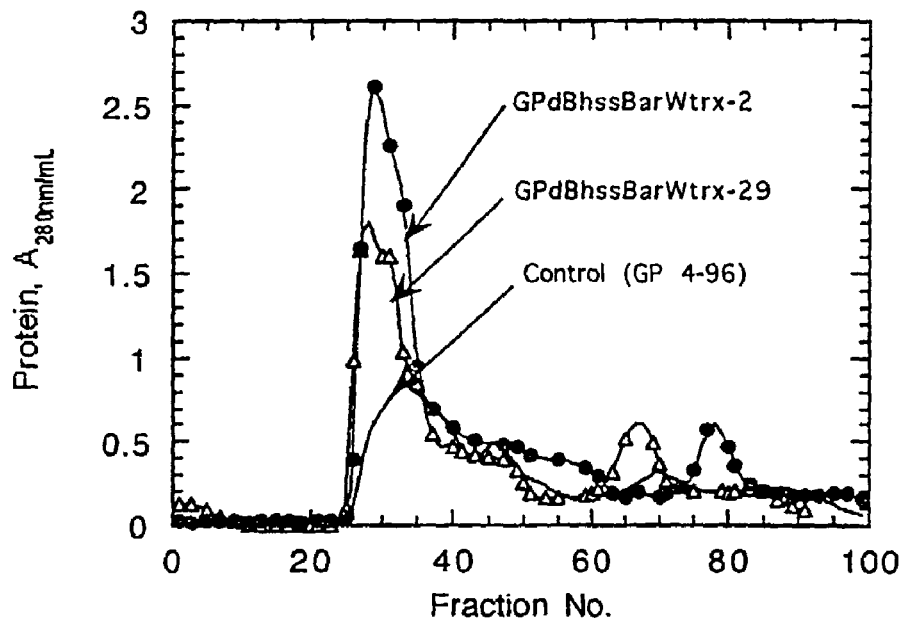
FIGURE 2

1. Wheat germ thioredoxin
2. Control (GP 4-96), nontransformed
3. Control, null segregant (GPdBssBarWtrx-29-11-10)
4. Transformed, heterozygous line (GPdBssBarWtrx-29)
5. Transformed, homozygous line 1 (GPdBssBarWtrx-29-3)
6. Transformed, homozygous line 2 (GPdBssBarWtrx-29-3-2)
7. Prestained standards AAGCTTTAACAACCCACACATTGATTGCAACTTAGTCCTACACAAGTTT
TCCATTCTTGTTTCAGGCTAACAACCTATACAAGGTTCCAAAATCATGC
AAAAGTGATGCTAGGTTGATAATGTGTGACATGTAAAGTGAATAAGG
TGAGTCATGCATACCAAACCTCGGGATTTCTATACTTTGTGTATGATCA
TATGCACAACTAAAAGGCAACTTTGATTATCAATTGAAAAGTACCG
CTTGTAGCTTGTGCAACCTAACACAATGTCCAAAAATCCATTTGCAAA
AGCATCCAAACACAATTGTTAAAGCTGTTCAAACAAACAAAGAAGAG
ATGAAGCCTGGCTACTATAAATAGGCAGGTAGTATAGAGATCTACACA
AGCACAAGCATCAAAACCAAGAAACACTAGTTAACACCAATCCACT<u>A</u>
<u>TGAAGACCTTCCTCATCTTTGCACTCCTCGCCATTGCGGCAACAAGTACG</u>
<u>ATTGCA</u>

FIGURE 6

CTTCGAGTGCCCGCCGATTTGCCAGCAATGGCTAACAGACACATATTCT
GCCAAAACCCCAGAACAATAATCACTTCTCGTAGATGAAGAGAACAG
ACCAAGATACAAACGTCCACGCTTCAGCAAACAGTACCCCAGAACTAG
GATTAAGCCGATTACGCGGCTTTAGCAGACCGTCCAAAAAAACTGTTTT
GCAAAGCTCCAATTCCTCCTTGCTTATCCAATTTCTTTTGTGTTGGCAAA
CTGCACTTGTCCAACCGATTTTGTTCTTCCCGTGTTTCTTCTTAGGCTAAC
TAACACAGCCGTGCACATAGCCATGGTCCGGAATCTTCACCTCGTCCCT
ATAAAAGCCCAGCCAATCTCCACAATCTCATCATCACCGAGAACACCG
AGAACCACAAAACTAGAGATCAATTCATTGACAGTCCACCGAG<u>ATGGC</u>
<u>TAAGCGGCTGGTCCTCTTTGTGGCGGTAATCGTCGCCCTCGTGGCTCTCA</u>
<u>CCACCGCT</u>

FIGURE 7

```
atg gcg gcg tcg gca acg gcg gcg gca gtg gcg gcg gag gtg atc tcg        48
Met Ala Ala Ser Ala Thr Ala Ala Ala Val Ala Ala Glu Val Ile Ser
 1           5                  10                  15 gtc cac agc ctg gag cag tgg acc atg cag atc gag gag gcc aac acc        96
Val His Ser Leu Glu Gln Trp Thr Met Gln Ile Glu Glu Ala Asn Thr
                 20                  25                  30 gcc aag aag ctg gtg gtg att gac ttc act gca tca tgg tgc gga cca       144
Ala Lys Lys Leu Val Val Ile Asp Phe Thr Ala Ser Trp Cys Gly Pro
         35                  40                  45 tgc cgc atc atg gct cca gtt ttc gct gat ctc gcc aag aag ttc cca       192
Cys Arg Ile Met Ala Pro Val Phe Ala Asp Leu Ala Lys Lys Phe Pro
     50                  55                  60 aat gct gtt ttc ctc aag gtc gac gtg gat gaa ctg aag ccc att gct       240
Asn Ala Val Phe Leu Lys Val Asp Val Asp Glu Leu Lys Pro Ile Ala
 65                  70                  75                  80 gag caa ttc agt gtc gag gcc atg cca acg ttc ctg ttc atg aag gaa       288
Glu Gln Phe Ser Val Glu Ala Met Pro Thr Phe Leu Phe Met Lys Glu
                 85                  90                  95 gga gac gtc aag gac agg gtt gtc gga gct atc aag gag gaa ctg acc       336
Gly Asp Val Lys Asp Arg Val Val Gly Ala Ile Lys Glu Glu Leu Thr
            100                 105                 110 gcc aag gtt ggg ctt cac gcg gcg gcc cag taa                           369
Ala Lys Val Gly Leu His Ala Ala Ala Gln
        115                 120
```

FIGURE 20

Figure 3. Scan Profile of Protein of Fraction 26 and 28 from Reversed-Phase C4 HPLC Column after Separation by SDS/PAGE.

Figure 4. 1D SDS/PAGE of Reversed Phase Albumin Fractions from Transgenic Wheat (without NADPH and NTR).

Figure 5. IEF (pH 5-8)/Tris-Tricine (16.5%) PAGE of Albumin Fraction from Transgenic Wheat Overexpressing Thioredoxin h.

```
a  MEGSAAAPLRTRVCIIGSGPAAHTAAIYAARAELKPVLFEGWMANDIAAGGQLTTTTDVE
b  MEEAAAGPLHTRVCIIGSGPAAHTAAVYAARAELKPVLFEGWLANDIAAGGQLTTTTDVE
c  MNG--LETHNTRLCIVGSGPAAHTAAIYAARAELKPLLFEGWMANDIAPGGQLTTTTDVE
d  MGT---T-KHSKLLILGSGPAGYTAAVYAARANLQPVLITG-----MEKGGQLTTTTEVE a  NFPGFPTGIMGIDLMDNCRAQSVRFGTNILSETVTEVDFSARPFRVTSDSTTVLADTVVV
b  NFPGFPDGILGIDLMDRCRAQSVRFGTKIFSETVTSVDFSSRPFRVSSDDTVVHADSVVV
c  NFPGFPEGILGVELTDKFRKQSERFGTTIFTETVTKVDFSSKPFKLFTDSKAILADAVIL
d  NWPGDPNDLTGPLLMERMHEHATKFETEIIFDHINKVDLQNRPFRLNGDNGEYTCDALII a  ATGAVARRLHFSGSD----TYWNRGISACAVCDGAAPIFRNKPIAVIGGGDSAMEEGNFL
b  ATGAVARRLHFAGSD----AFWNRGITACAVCDGAAPIFRNKPIAVVGGGDSAMEEANFL
c  ATGAVAKRLSFVGSGEASGGFWNRGISACAVCDGAAPIFRNKPLAVIGGGDSAMEEANFL
d  ATGASARYLGLPSEE----AFKGRGVSACATCDG--FFYRNQKVAVIGGGNTAVEEALYL a  TKYGSQVYIIHRRNTFRASKIMQARALS---NPKIQVVWDSEVVEAYGGAGGGPLAGVKV
b  TKYGSRVYIIHRRDAFRASKIMQARALS---NPKIQVVWDSEVVEAYGGSDGGPLGGVKV
c  TKYGSKVYIIHRRDAFRASKIMQQRALS---NPKIDVIWNSSVVEAYGDGERDVLGGLKV
d  SNIASEVHLIHRRDGFRAEKILIKRLMDKVENGNIILHTNRTLEEVTGDQMG--VTGVRL a  KNLVTG-EVSDLQVSGLFFAIGHEPATKFLNGQLELHADGYVATKPG----STHTSVEGV
b  KNLVTG-EVSDFRVAGLFFAIGHEPATKFLAGQLELDSEGYVATKPG----STHTSVKGV
c  KNVVTG-DVSDLKVSGLFFAIGHEPATKFLDGGVELDSDGYVVTKPG----TTQTSVPGV
d  RDTQNSDNIESLDVAGLFVAIGHSPNTAIFEGQLELEN-GYIKVQSGIHGNATQTSIPGV a  FAAGDVQDKKYRQAITAAGSGCMAALDAEHYLQEVGAQVGKSD
b  FAAGDVQDKKYRQAITAAGSGCMAALDAEHYLQEVGAQEGKTD
c  FAAGDVQDKKYRQAITAAGTGCMAALDAEHYLQEIGSQQGKSD
d  FAAGDVMDHIYRQAITSAGTGCMAALDAERYLDGLADAK----
```

Alignment of NADPh-Thioredoxin Reductases from Different Sources.
Conserved regions in the sequences of the three plants are highlighted.
a: Barley    b: Wheat    c: Arabidopsis    d: E. coli

FIGURE 30

```
a  MAGTDSSASSRQSS-FNSLAKDLELPLEQGCLTIVVLGASGALPRRKRSRHFYHLFEQGF
b  MAGTDSSASSRQSS-FNSLAKDLELPLEKGCLTIVVLGASGDLAKKKTFPALYHLFEQGF
c  MSG-GSSPRSRRSS-FNSLSRDLELPSEQGCLSVIVLGASGDLAKKKTFPALFHLFAQGF
d  MAAS-WCIEKRGSIRLDSFR-DNDNIPETGCLSIIVLGASGDLAKKKTFPALFNLYRQGF
e  MGSGQWHVEKRSTFRNDSFVREYGIVPETGCLSIIVLGASGDLAKKKTFPALFNLYRQGF a  LQSGEVHIVGYARTNLSDDGLRGRIRAYLKGAS----EEHVSEFLQLIKYVSGSYDSGEG
b  LQSGEVHIVGYARTNLSDDGLRGRIRAYLKGAS----EEHVSEFLQLIKYVSGSYDSGEG
c  IQSGEVHIFGYARSNLSDDGLRGRIRGYLKGAS----EEHLSDFLQLIKYVSGSYDSGEG
d  LQSNEVHIFGYARTKISDDDLRGRIRGYLSQGK--ENEEEVSEFLQLIKYVSGSYDSGEG
e  LNPDEVHIFGYARTKISDEELRDRIRGYLVDEKNAEQAEALSKFLQLIKYVSGPYDAEEG a  PEKLNKEISDYEMSNNS--GSSRRLFYLALPPSVYPSVCKMIRTYCMSPTSRTGWTRVIV
b  PEKLNKEISDYEMSNNS--GSSRRLFYLALPPSVYPSVCKMIRTYCMSPTSRAGWTRVIV
c  PEKLNKEISEYEKSNKS--ESPRRLFYLALPPSVYPSVCKMIRTYCMNPS---GWTRVIV
d  PSLODKATAEHEIAKNSTEGSSRRLFYPALPPSVYPSVCRMIKNYCMNKSDLGGWTRIVV
e  PQRLDKAISEHEISKNSTEGSSRRLFYLALPPSVYPSVCKMIKTCCMNKSDLGGWTRIVV a  EKPFGRDLDSAEELSSQLGELFQEDQLYRIDHYLGKELVQNLLVLRFANRLFLPLWNRDN
b  EKPFGRGLDSAEELSSQLGELFEEDQLYRIDHYLGKELVQNLLVLRFANRLFLPLWNRDN
c  EKPFGKDLDSSEELSAQLGELFDENQLYRIDHYLGKELVQNLLVLRFANRLFLPLWNRDN
d  EKPFGKDLASAEQLSSQIGELFDPQIYRIDHYLGKELVQNLLVLRFANRLFLPLWNRDN
e  EKPFGKDLESAEQLSSQIGELFDESQIYRIDHYLGKELVQNMLVLRFANRRFLPLWNRDN a  VDNIQIVFREDFGTDGRGGYFDQYGIIRDIIQNHLLQVFCLVAMEKPVSLKPEHIRDEKV
b  VDNIQIVFREDFGTDGRGGYFDQYGIIRGIIQNHLLQVFCLVAMEKPVSLKPEHIRDEKV
c  IDNIQIVFREDFGTDGRGGYFDQYGIIRDIIQNHLLQVFCLVAMEKPVSLKPEHIRDEKV
d  IDNIQIVFREDFGTEGRGGYFDEYGIIRDIIQNQLLQVLCLVAMEKPVSQKPEHIRDEKV
e  IENVQIVFREDFGTEGRGGYFDEYGIIRDIIQNHLLQVLCLVAMEKPISLKPEHIRDEKV a  KVLQSVNPIKDEEVVLGQYQGYKDDPTVPDDSNTPTFASIVLRVHNERWEGVPFILKAGK
b  KVLQSVNPIKDEEVVLGQYQGYKEDPTVPDDSNTPTFASIVLRVHNERWEGVPFILKAGK
c  KVLQSVNPIKHDEVVLGQYEGYKDDPTVPDDSNTPTFASVVFRVHNERWEGVPFILKAGK
d  KVLQSMLPIKDEEVVLGQYEGYKDDPTVPDNSNTPTFATMVLRIHNERWEGVPFIMKAGK
e  KVLQSVVPISDDEVVLGQYEGYRDDDTVPNDSNTPTFATTILRIHNERWEGVPFILKAGK a  ALNSRKAEIRVQFKDVPGDIFKCKKQGRNEFVIRLQPSEAMYMKLT----VKKPGLEMAT
b  ALNSRKAEIRVQFKDVPGDIFKCKKQGRNEFVIRLQPSEAMYMKLT----VKKPGLEMAT
c  ALSSRKAEVRVQFKDVPGDIFKCKFQGRNEFVIRLQPSEAMYMKLT----VKKPGLEMAT
d  ALNSRKAEIRVQFKDVPGDIFRCKKQGRNEFVIRLQPSEAMYMKLT----VKKPGLEMST
e  ALNSRKAEIRIQFKDVPGDIFRCQKQGRNEFVIRLQPSEAMYMKLT----VKQPGLDMNT a  EQSELDLSYGMRYQDVKIPEAYERLILDTIRGDQQHFVRRDELKAAWQIFTPLLHNIDAG
b  EQSELDLSYGMRYQDVKIPEAYERLILDTIRGDQQHFVRRDELKAAWQIFTPLLHDIDAG
c  EQSELDLSYGMRYQNMKIPEACERLILDTIRGDQQHFVRRDELKAAWQIFTPLLHDIDEG
d  VQSELDLSYRQRYQGVVIPEAYERLILDTIRGDQQHFVRRDELKAAWEIFTPLLHRIDDG
e  VQSELDLSYGQRYQGVAIPEAYERLILDTIKGDQQHFVRRDELKVAWEIFTPLLHRIDKG a  KLKAVSYKPGSRGPKEADELSEKVGYMQTHGYIWIPPXLA
b  KLKAVSYKPGSRGPKEADELSEKVGYMQTHGYIWIPPTLA
c  KVKSIPYQPGSRGPKEADELSERVGYMQTHGYIWIPPTLA
d  EVKPIPYKPGSRGPAEADELLQNVGYVQTHGYICIPPTL-
e  EVKSIPYKPGSRGPKEADQLLEKAGYLQTHGYIWIPPTL-
```

Alignment of G6PDHs from Different Sources.
Conserved regions in the sequences of the five plants are highlighted.
a: barley     b: wheat       c: rice
d: tobacco    e: Arabidopsis

FIGURE 31

```
a   MAAS---ATAAAVAA-EVISVHSLEQWTMQIEEANTAKKLVVIDFTASWCGPCRIMAPVF
b   MAASAATATAAAVGAGEVISVHSLEQWTMQIEEANAAKKLVVIDFTASWCGPCRIMAPIF
c   MAA---------EEGVVIACHNKDEFDAQMTKAKEAGKVVIIDFTASWCGPCRFIAPVF
d   MAAN----DATSSEEGQVFGCHKVEEWNEYFKKGVETKKLVVVDFTASWCGPCRFIAPIL
e   MAS----------EEGQVIACHTVETWNEQLQKANESKTLVVVDFTASWCGPCRFIAPFF
f   -----------MSD--KIIHLTDDSFDTDVLKADG---AILVDFWAEWCGPCKMIAPIL a   ADLAKKFP-NAVFLKVDVDELKPIAEQFSVEAMPTFLFMKEGDVKDRVVGAI-KEELTAK
b   ADLAKKFP-AAVFLKVDVDELKSIAEQFSVEAMPTFLFMKEGDVKDRVVGAI-KEELTNK
c   AEYAKKFP-GAVFLKVDVDELKEVAEKYNVEAMPTFLFIKDGAEADKVVGAR-KDDLQNT
d   ADIAKKMP-HVIFLKVDVDELKTVSAEWSVEAMPTFVFIKDGKEVDRVVGAK-KEELQQT
e   ADLAKKLP-NVLFLKVDTDELKSVASDWAIQAMPTFMFLKEGKILDKVVGAK-KDELQST
f   DEIADEYQGKLTVAKLNIDQNPGTAPKYGIRGIPTLLLFKNGEVAATKVGALSKGQLKEF a   VGLHAAAQ------
b   VGLHAAQ-------
c   IVKEVGATAASASA
d   IVKEAAPATVTA--
e   IAKHLA--------
f   LDANLA--------
```

Alignment of Thioredoxins from Different Sources.
Conserved regions in the sequences of the five plants are highlighted.
a: Barley        b: Wheat          c: Rice
d: Tobacco       e: Arabidopsis    f: E. coli

FIGURE 32

SEQUENCE LISTING

```
<160> NUMBER OF SEQ ID NOS: 55

<210> SEQ ID NO 1
<211> LENGTH: 5
<212> TYPE: PRT
<213> ORGANISM: Artificial Sequence
<220> FEATURE:
<223> OTHER INFORMATION: Thioredoxin Polypeptide
<220> FEATURE:
<221> NAME/KEY: VARIANT
<222> LOCATION: 3
<223> OTHER INFORMATION: Xaa = Gly or Pro

<400> SEQUENCE: 1

Trp Cys Xaa Pro Cys
1               5

<210> SEQ ID NO 2
<211> LENGTH: 14
<212> TYPE: PRT
<213> ORGANISM: Wheat

<400> SEQUENCE: 2

Asp Cys Cys Gln Gln Leu Ala Asp Ile Ser Glu Trp Cys Arg
1               5                   10

<210> SEQ ID NO 3
<211> LENGTH: 15
<212> TYPE: PRT
<213> ORGANISM: Wheat

<400> SEQUENCE: 3

Glu Tyr Val Ala Gln Gln Thr Cys Gly Val Gly Ile Val Gly Ser
1               5                   10                  15

<210> SEQ ID NO 4
<211> LENGTH: 17
<212> TYPE: PRT
<213> ORGANISM: Wheat

<400> SEQUENCE: 4

Asp Ala Leu Leu Gln Gln Cys Ser Pro Val Ala Asp Met Ser Phe Leu
1               5                   10                  15

Arg
```

-continued

<210> SEQ ID NO 5
<211> LENGTH: 21
<212> TYPE: PRT
<213> ORGANISM: Wheat

<400> SEQUENCE: 5

Ser Gly Pro Trp Met Cys Tyr Pro Gly Gln Ala Phe Gln Val Pro Ala
 1               5                  10                  15

Leu Pro Ala Cys Arg
            20

<210> SEQ ID NO 6
<211> LENGTH: 486
<212> TYPE: DNA
<213> ORGANISM: Barley

<400> SEQUENCE: 6
aagctttaac aacccacaca ttgattgcaa cttagtccta cacaagtttt ccattcttgt      60
ttcaggctaa caacctatac aaggttccaa atcatgcaa aagtgatgct aggttgataa     120
tgtgtgacat gtaaagtgaa taaggtgagt catgcatacc aaacctcggg atttctatac     180
tttgtgtatg atcatatgca caactaaaag gcaactttga ttatcaattg aaaagtaccg     240
cttgtagctt gtgcaaccta acacaatgtc caaaaatcca tttgcaaaag catccaaaca     300
caattgttaa agctgttcaa acaaacaaag aagagatgaa gcctggctac tataaatagg     360
caggtagtat agagatctac acaagcacaa gcatcaaaac caagaaacac tagttaacac     420
caatccacta tgaagacctt cctcatcttt gcactcctcg ccattgcggc aacaagtacg     480
attgca                                                                486

<210> SEQ ID NO 7
<211> LENGTH: 497
<212> TYPE: DNA
<213> ORGANISM: Barley

<400> SEQUENCE: 7
cttcgagtgc ccgccgattt gccagcaatg gctaacagac acatattctg ccaaaacccc      60
agaacaataa tcacttctcg tagatgaaga aacagacca agatacaaac gtccacgctt     120
cagcaaacag taccccagaa ctaggattaa gccgattacg cggctttagc agaccgtcca     180
aaaaaactgt tttgcaaagc tccaattcct ccttgcttat ccaatttctt ttgtgttggc     240
aaactgcact tgtccaaccg attttgttct tcccgtgttt cttcttaggc taactaacac     300
agccgtgcac atagccatgg tccggaatct tcacctcgtc cctataaaag cccagccaat     360
ctccacaatc tcatcatcac cgagaacacc gagaaccaca aaactagaga tcaattcatt     420
gacagtccac cgagatggct aagcggctgg tcctctttgt ggcggtaatc gtcgccctcg     480
tggctctcac caccgct                                                    497

<210> SEQ ID NO 8
<211> LENGTH: 369
<212> TYPE: DNA
<213> ORGANISM: Barley
<220> FEATURE:
<221> NAME/KEY: CDS
<222> LOCATION: (1)...(369)

<400> SEQUENCE: 8 atg gcg gcg tcg gca acg gcg gcg gca gtg gcg gcg gag gtg atc tcg      48

```
Met Ala Ser Ala Thr Ala Ala Val Ala Ala Glu Val Ile Ser
1               5                   10                  15 gtc cac agc ctg gag cag tgg acc atg cag atc gag gag gcc aac acc      96
Val His Ser Leu Glu Gln Trp Thr Met Gln Ile Glu Glu Ala Asn Thr
                20                  25                  30 gcc aag aag ctg gtg gtg att gac ttc act gca tca tgg tgc gga cca     144
Ala Lys Lys Leu Val Val Ile Asp Phe Thr Ala Ser Trp Cys Gly Pro
        35                  40                  45 tgc cgc atc atg gct cca gtt ttc gct gat ctc gcc aag aag ttc cca     192
Cys Arg Ile Met Ala Pro Val Phe Ala Asp Leu Ala Lys Lys Phe Pro
    50                  55                  60 aat gct gtt ttc ctc aag gtc gac gtg gat gaa ctg aag ccc att gct     240
Asn Ala Val Phe Leu Lys Val Asp Val Asp Glu Leu Lys Pro Ile Ala
65                  70                  75                  80 gag caa ttc agt gtc gag gcc atg cca acg ttc ctg ttc atg aag gaa     288
Glu Gln Phe Ser Val Glu Ala Met Pro Thr Phe Leu Phe Met Lys Glu
                85                  90                  95 gga gac gtc aag gac agg gtt gtc gga gct atc aag gag gaa ctg acc     336
Gly Asp Val Lys Asp Arg Val Val Gly Ala Ile Lys Glu Glu Leu Thr
            100                 105                 110 gcc aag gtt ggg ctt cac gcg gcg gcc cag taa                         369
Ala Lys Val Gly Leu His Ala Ala Ala Gln *
        115                 120
```

<210> SEQ ID NO 9
<211> LENGTH: 122
<212> TYPE: PRT
<213> ORGANISM: Barley

<400> SEQUENCE: 9

```
Met Ala Ser Ala Thr Ala Ala Val Ala Ala Glu Val Ile Ser
1               5                   10                  15

Val His Ser Leu Glu Gln Trp Thr Met Gln Ile Glu Glu Ala Asn Thr
                20                  25                  30

Ala Lys Lys Leu Val Val Ile Asp Phe Thr Ala Ser Trp Cys Gly Pro
        35                  40                  45

Cys Arg Ile Met Ala Pro Val Phe Ala Asp Leu Ala Lys Lys Phe Pro
    50                  55                  60

Asn Ala Val Phe Leu Lys Val Asp Val Asp Glu Leu Lys Pro Ile Ala
65                  70                  75                  80

Glu Gln Phe Ser Val Glu Ala Met Pro Thr Phe Leu Phe Met Lys Glu
                85                  90                  95

Gly Asp Val Lys Asp Arg Val Val Gly Ala Ile Lys Glu Glu Leu Thr
            100                 105                 110

Ala Lys Val Gly Leu His Ala Ala Ala Gln
        115                 120
```

<210> SEQ ID NO 10
<211> LENGTH: 331
<212> TYPE: PRT
<213> ORGANISM: Barley

<400> SEQUENCE: 10

```
Met Glu Gly Ser Ala Ala Ala Pro Leu Arg Thr Arg Val Cys Ile Ile
1               5                   10                  15

Gly Ser Gly Pro Ala Ala His Thr Ala Ala Ile Tyr Ala Ala Arg Ala
                20                  25                  30

Glu Leu Lys Pro Val Leu Phe Glu Gly Trp Met Ala Asn Asp Ile Ala
        35                  40                  45
```

```
Ala Gly Gly Gln Leu Thr Thr Thr Asp Val Glu Asn Phe Pro Gly
         50                  55                  60

Phe Pro Thr Gly Ile Met Gly Ile Asp Leu Met Asp Asn Cys Arg Ala
 65              70                  75                  80

Gln Ser Val Arg Phe Gly Thr Asn Ile Leu Ser Glu Thr Val Thr Glu
                 85                  90                  95

Val Asp Phe Ser Ala Arg Pro Phe Arg Val Thr Ser Asp Ser Thr Thr
            100                 105                 110

Val Leu Ala Asp Thr Val Val Ala Thr Gly Ala Val Ala Arg Arg
            115                 120                 125

Leu His Phe Ser Gly Ser Asp Thr Tyr Trp Asn Arg Gly Ile Ser Ala
        130                 135                 140

Cys Ala Val Cys Asp Gly Ala Ala Pro Ile Phe Arg Asn Lys Pro Ile
145                 150                 155                 160

Ala Val Ile Gly Gly Asp Ser Ala Met Glu Glu Gly Asn Phe Leu
                165                 170                 175

Thr Lys Tyr Gly Ser Gln Val Tyr Ile Ile His Arg Arg Asn Thr Phe
            180                 185                 190

Arg Ala Ser Lys Ile Met Gln Ala Arg Ala Leu Ser Asn Pro Lys Ile
        195                 200                 205

Gln Val Val Trp Asp Ser Glu Val Glu Ala Tyr Gly Gly Ala Gly
        210                 215                 220

Gly Gly Pro Leu Ala Gly Val Lys Val Lys Asn Leu Val Thr Gly Glu
225                 230                 235                 240

Val Ser Asp Leu Gln Val Ser Gly Leu Phe Phe Ala Ile Gly His Glu
                245                 250                 255

Pro Ala Thr Lys Phe Leu Asn Gly Gln Leu Glu Leu His Ala Asp Gly
            260                 265                 270

Tyr Val Ala Thr Lys Pro Gly Ser Thr His Thr Ser Val Glu Gly Val
        275                 280                 285

Phe Ala Ala Gly Asp Val Gln Asp Lys Lys Tyr Arg Gln Ala Ile Thr
290                 295                 300

Ala Ala Gly Ser Gly Cys Met Ala Ala Leu Asp Ala Glu His Tyr Leu
305                 310                 315                 320

Gln Glu Val Gly Ala Gln Val Gly Lys Ser Asp
                325                 330

<210> SEQ ID NO 11
<211> LENGTH: 331
<212> TYPE: PRT
<213> ORGANISM: Wheat

<400> SEQUENCE: 11

Met Glu Glu Ala Ala Ala Gly Pro Leu His Thr Arg Val Cys Ile Ile
 1               5                  10                  15

Gly Ser Gly Pro Ala Ala His Thr Ala Ala Val Tyr Ala Ala Arg Ala
                 20                  25                  30

Glu Leu Lys Pro Val Leu Phe Glu Gly Trp Leu Ala Asn Asp Ile Ala
             35                  40                  45

Ala Gly Gly Gln Leu Thr Thr Thr Asp Val Glu Asn Phe Pro Gly
         50                  55                  60

Phe Pro Asp Gly Ile Leu Gly Ile Asp Leu Met Asp Arg Cys Arg Ala
 65              70                  75                  80

Gln Ser Val Arg Phe Gly Thr Lys Ile Phe Ser Glu Thr Val Thr Ser
```

```
                 85                  90                  95
Val Asp Phe Ser Ser Arg Pro Phe Arg Val Ser Ser Asp Asp Thr Val
            100                 105                 110
Val His Ala Asp Ser Val Val Ala Thr Gly Ala Val Ala Arg Arg
            115                 120                 125
Leu His Phe Ala Gly Ser Asp Ala Phe Trp Asn Arg Gly Ile Thr Ala
            130                 135                 140
Cys Ala Val Cys Asp Gly Ala Ala Pro Ile Phe Arg Asn Lys Pro Ile
145                 150                 155                 160
Ala Val Val Gly Gly Asp Ser Ala Met Glu Glu Ala Asn Phe Leu
                165                 170                 175
Thr Lys Tyr Gly Ser Arg Val Tyr Ile Ile His Arg Arg Asp Ala Phe
            180                 185                 190
Arg Ala Ser Lys Ile Met Gln Ala Arg Ala Leu Ser Asn Pro Lys Ile
            195                 200                 205
Gln Val Val Trp Asp Ser Glu Val Val Glu Ala Tyr Gly Gly Ser Asp
            210                 215                 220
Gly Gly Pro Leu Gly Gly Val Lys Val Lys Asn Leu Val Thr Gly Glu
225                 230                 235                 240
Val Ser Asp Phe Arg Val Ala Gly Leu Phe Phe Ala Ile Gly His Glu
                245                 250                 255
Pro Ala Thr Lys Phe Leu Ala Gly Gln Leu Glu Leu Asp Ser Glu Gly
            260                 265                 270
Tyr Val Ala Thr Lys Pro Gly Ser Thr His Thr Ser Val Lys Gly Val
            275                 280                 285
Phe Ala Ala Gly Asp Val Gln Asp Lys Lys Tyr Arg Gln Ala Ile Thr
            290                 295                 300
Ala Ala Gly Ser Gly Cys Met Ala Ala Leu Asp Ala Glu His Tyr Leu
305                 310                 315                 320
Gln Glu Val Gly Ala Gln Glu Gly Lys Thr Asp
                325                 330

<210> SEQ ID NO 12
<211> LENGTH: 333
<212> TYPE: PRT
<213> ORGANISM: Arabidopsis

<400> SEQUENCE: 12

Met Asn Gly Leu Glu Thr His Asn Thr Arg Leu Cys Ile Val Gly Ser
1               5                   10                  15
Gly Pro Ala Ala His Thr Ala Ala Ile Tyr Ala Ala Arg Ala Glu Leu
            20                  25                  30
Lys Pro Leu Leu Phe Glu Gly Trp Met Ala Asn Asp Ile Ala Pro Gly
            35                  40                  45
Gly Gln Leu Thr Thr Thr Thr Asp Val Glu Asn Phe Pro Gly Phe Pro
        50                  55                  60
Glu Gly Ile Leu Gly Val Glu Leu Thr Asp Lys Phe Arg Lys Gln Ser
65                  70                  75                  80
Glu Arg Phe Gly Thr Thr Ile Phe Thr Glu Thr Val Thr Lys Val Asp
                85                  90                  95
Phe Ser Ser Lys Pro Phe Lys Leu Phe Thr Asp Ser Lys Ala Ile Leu
            100                 105                 110
Ala Asp Ala Val Ile Leu Ala Thr Gly Ala Val Ala Lys Arg Leu Ser
            115                 120                 125
```

-continued

```
Phe Val Gly Ser Gly Glu Ala Ser Gly Gly Phe Trp Asn Arg Gly Ile
    130                 135                 140

Ser Ala Cys Ala Val Cys Asp Gly Ala Ala Pro Ile Phe Arg Asn Lys
145                 150                 155                 160

Pro Leu Ala Val Ile Gly Gly Asp Ser Ala Met Glu Glu Ala Asn
                165                 170                 175

Phe Leu Thr Lys Tyr Gly Ser Lys Val Tyr Ile Ile His Arg Arg Asp
            180                 185                 190

Ala Phe Arg Ala Ser Lys Ile Met Gln Gln Arg Ala Leu Ser Asn Pro
        195                 200                 205

Lys Ile Asp Val Ile Trp Asn Ser Ser Val Val Glu Ala Tyr Gly Asp
    210                 215                 220

Gly Glu Arg Asp Val Leu Gly Leu Lys Val Lys Asn Val Val Thr
225                 230                 235                 240

Gly Asp Val Ser Asp Leu Lys Val Ser Gly Leu Phe Phe Ala Ile Gly
                245                 250                 255

His Glu Pro Ala Thr Lys Phe Leu Asp Gly Gly Val Glu Leu Asp Ser
            260                 265                 270

Asp Gly Tyr Val Val Thr Lys Pro Gly Thr Thr Gln Thr Ser Val Pro
        275                 280                 285

Gly Val Phe Ala Ala Gly Asp Val Gln Asp Lys Lys Tyr Arg Gln Ala
    290                 295                 300

Ile Thr Ala Ala Gly Thr Gly Cys Met Ala Ala Leu Asp Ala Glu His
305                 310                 315                 320

Tyr Leu Gln Glu Ile Gly Ser Gln Gln Gly Lys Ser Asp
                325                 330
```

<210> SEQ ID NO 13
<211> LENGTH: 321
<212> TYPE: PRT
<213> ORGANISM: E. coli

<400> SEQUENCE: 13

```
Met Gly Thr Thr Lys His Ser Lys Leu Leu Ile Leu Gly Ser Gly Pro
1               5                   10                  15

Ala Gly Tyr Thr Ala Ala Val Tyr Ala Ala Arg Ala Asn Leu Gln Pro
            20                  25                  30

Val Leu Ile Thr Gly Met Glu Lys Gly Gly Gln Leu Thr Thr Thr Thr
        35                  40                  45

Glu Val Glu Asn Trp Pro Gly Asp Pro Asn Asp Leu Thr Gly Pro Leu
    50                  55                  60

Leu Met Glu Arg Met His Glu His Ala Thr Lys Phe Glu Thr Glu Ile
65                  70                  75                  80

Ile Phe Asp His Ile Asn Lys Val Asp Leu Gln Asn Arg Pro Phe Arg
                85                  90                  95

Leu Asn Gly Asp Asn Gly Glu Tyr Thr Cys Asp Ala Leu Ile Ile Ala
            100                 105                 110

Thr Gly Ala Ser Ala Arg Tyr Leu Gly Leu Pro Ser Glu Glu Ala Phe
        115                 120                 125

Lys Gly Arg Gly Val Ser Ala Cys Ala Thr Cys Asp Gly Phe Phe Tyr
    130                 135                 140

Arg Asn Gln Lys Val Ala Val Ile Gly Gly Asn Thr Ala Val Glu
145                 150                 155                 160

Glu Ala Leu Tyr Leu Ser Asn Ile Ala Ser Glu Val His Leu Ile His
                165                 170                 175
```

-continued

```
Arg Arg Asp Gly Phe Arg Ala Glu Lys Ile Leu Ile Lys Arg Leu Met
            180                 185                 190

Asp Lys Val Glu Asn Gly Asn Ile Ile Leu His Thr Asn Arg Thr Leu
            195                 200                 205

Glu Glu Val Thr Gly Asp Gln Met Gly Val Thr Gly Val Arg Leu Arg
            210                 215                 220

Asp Thr Gln Asn Ser Asp Asn Ile Glu Ser Leu Asp Val Ala Gly Leu
225                 230                 235                 240

Phe Val Ala Ile Gly His Ser Pro Asn Thr Ala Ile Phe Glu Gly Gln
            245                 250                 255

Leu Glu Leu Glu Asn Gly Tyr Ile Lys Val Gln Ser Gly Ile His Gly
            260                 265                 270

Asn Ala Thr Gln Thr Ser Ile Pro Gly Val Phe Ala Ala Gly Asp Val
            275                 280                 285

Met Asp His Ile Tyr Arg Gln Ala Ile Thr Ser Ala Gly Thr Gly Cys
            290                 295                 300

Met Ala Ala Leu Asp Ala Glu Arg Tyr Leu Asp Gly Leu Ala Asp Ala
305                 310                 315                 320

Lys

<210> SEQ ID NO 14
<211> LENGTH: 509
<212> TYPE: PRT
<213> ORGANISM: Barley
<220> FEATURE:
<221> NAME/KEY: VARIANT
<222> LOCATION: 507
<223> OTHER INFORMATION: Xaa = Any Amino Acid

<400> SEQUENCE: 14

Met Ala Gly Thr Asp Ser Ser Ala Ser Ser Arg Gln Ser Ser Phe Asn
1               5                   10                  15

Ser Leu Ala Lys Asp Leu Glu Leu Pro Leu Glu Gln Gly Cys Leu Thr
            20                  25                  30

Ile Val Val Leu Gly Ala Ser Gly Ala Leu Pro Arg Arg Lys Arg Ser
            35                  40                  45

Arg His Phe Tyr His Leu Phe Glu Gln Gly Phe Leu Gln Ser Gly Glu
        50                  55                  60

Val His Ile Val Gly Tyr Ala Arg Thr Asn Leu Ser Asp Asp Gly Leu
65                  70                  75                  80

Arg Gly Arg Ile Arg Ala Tyr Leu Lys Gly Ala Ser Glu Glu His Val
            85                  90                  95

Ser Glu Phe Leu Gln Leu Ile Lys Tyr Val Ser Gly Ser Tyr Asp Ser
            100                 105                 110

Gly Glu Gly Phe Glu Lys Leu Asn Lys Glu Ile Ser Asp Tyr Glu Met
            115                 120                 125

Ser Asn Asn Ser Gly Ser Ser Arg Arg Leu Phe Tyr Leu Ala Leu Pro
130                 135                 140

Pro Ser Val Tyr Pro Ser Val Cys Lys Met Ile Arg Thr Tyr Cys Met
145                 150                 155                 160

Ser Pro Thr Ser Arg Thr Gly Trp Thr Arg Val Ile Val Glu Lys Pro
            165                 170                 175

Phe Gly Arg Asp Leu Asp Ser Ala Glu Glu Leu Ser Ser Gln Leu Gly
            180                 185                 190

Glu Leu Phe Gln Glu Asp Gln Leu Tyr Arg Ile Asp His Tyr Leu Gly
```

```
            195                 200                 205
Lys Glu Leu Val Gln Asn Leu Leu Val Leu Arg Phe Ala Asn Arg Leu
    210                 215                 220

Phe Leu Pro Leu Trp Asn Arg Asp Asn Val Asp Asn Ile Gln Ile Val
225                 230                 235                 240

Phe Arg Glu Asp Phe Gly Thr Asp Gly Arg Gly Gly Tyr Phe Asp Gln
                245                 250                 255

Tyr Gly Ile Ile Arg Asp Ile Ile Gln Asn His Leu Leu Gln Val Phe
            260                 265                 270

Cys Leu Val Ala Met Glu Lys Pro Val Ser Leu Lys Pro Glu His Ile
        275                 280                 285

Arg Asp Glu Lys Val Lys Val Leu Gln Ser Val Asn Pro Ile Lys Asp
    290                 295                 300

Glu Glu Val Val Leu Gly Gln Tyr Gln Gly Tyr Lys Asp Asp Pro Thr
305                 310                 315                 320

Val Pro Asp Asp Ser Asn Thr Pro Thr Phe Ala Ser Ile Val Leu Arg
                325                 330                 335

Val His Asn Glu Arg Trp Glu Gly Val Pro Phe Ile Leu Lys Ala Gly
            340                 345                 350

Lys Ala Leu Asn Ser Arg Lys Ala Glu Ile Arg Val Gln Phe Lys Asp
        355                 360                 365

Val Pro Gly Asp Ile Phe Lys Cys Lys Lys Gln Gly Arg Asn Glu Phe
    370                 375                 380

Val Ile Arg Leu Gln Pro Ser Glu Ala Met Tyr Met Lys Leu Thr Val
385                 390                 395                 400

Lys Lys Pro Gly Leu Glu Met Ala Thr Glu Gln Ser Glu Leu Asp Leu
                405                 410                 415

Ser Tyr Gly Met Arg Tyr Gln Asp Val Lys Ile Pro Glu Ala Tyr Glu
            420                 425                 430

Arg Leu Ile Leu Asp Thr Ile Arg Gly Asp Gln Gln His Phe Val Arg
        435                 440                 445

Arg Asp Glu Leu Lys Ala Ala Trp Gln Ile Phe Thr Pro Leu Leu His
    450                 455                 460

Asn Ile Asp Ala Gly Lys Leu Lys Ala Val Ser Tyr Lys Pro Gly Ser
465                 470                 475                 480

Arg Gly Pro Lys Glu Ala Asp Glu Leu Ser Glu Lys Val Gly Tyr Met
                485                 490                 495

Gln Thr His Gly Tyr Ile Trp Ile Pro Pro Xaa Leu Ala
            500                 505

<210> SEQ ID NO 15
<211> LENGTH: 509
<212> TYPE: PRT
<213> ORGANISM: Wheat

<400> SEQUENCE: 15

Met Ala Gly Thr Asp Ser Ser Ala Ser Ser Arg Gln Ser Ser Phe Asn
1               5                   10                  15

Ser Leu Ala Lys Asp Leu Glu Leu Pro Leu Glu Lys Gly Cys Leu Thr
                20                  25                  30

Ile Val Val Leu Gly Ala Ser Gly Asp Leu Ala Lys Lys Lys Thr Phe
            35                  40                  45

Pro Ala Leu Tyr His Leu Phe Glu Gln Gly Phe Leu Gln Ser Gly Glu
        50                  55                  60
```

| | | | | | | | | | | | | | | |
|---|---|---|---|---|---|---|---|---|---|---|---|---|---|---|

Val His Ile Val Gly Tyr Ala Arg Thr Asn Leu Ser Asp Asp Gly Leu
 65                  70                  75                  80

Arg Gly Arg Ile Arg Ala Tyr Leu Lys Gly Ala Ser Glu Glu His Val
                 85                  90                  95

Ser Glu Phe Leu Gln Leu Ile Lys Tyr Val Ser Gly Ser Tyr Asp Ser
            100                 105                 110

Gly Glu Gly Phe Glu Lys Leu Asn Lys Glu Ile Ser Asp Tyr Glu Met
            115                 120                 125

Ser Asn Asn Ser Gly Ser Ser Arg Arg Leu Phe Tyr Leu Ala Leu Pro
130                 135                 140

Pro Ser Val Tyr Pro Ser Val Cys Lys Met Ile Arg Thr Tyr Cys Met
145                 150                 155                 160

Ser Pro Thr Ser Arg Ala Gly Trp Thr Arg Val Ile Val Glu Lys Pro
                165                 170                 175

Phe Gly Arg Gly Leu Asp Ser Ala Glu Glu Leu Ser Ser Gln Leu Gly
            180                 185                 190

Glu Leu Phe Glu Glu Asp Gln Leu Tyr Arg Ile Asp His Tyr Leu Gly
            195                 200                 205

Lys Glu Leu Val Gln Asn Leu Leu Val Leu Arg Phe Ala Asn Arg Leu
            210                 215                 220

Phe Leu Pro Leu Trp Asn Arg Asp Asn Val Asp Asn Ile Gln Ile Val
225                 230                 235                 240

Phe Arg Glu Asp Phe Gly Thr Asp Gly Arg Gly Gly Tyr Phe Asp Gln
                245                 250                 255

Tyr Gly Ile Ile Arg Gly Ile Ile Gln Asn His Leu Leu Gln Val Phe
            260                 265                 270

Cys Leu Val Ala Met Glu Lys Pro Val Ser Leu Lys Pro Glu His Ile
            275                 280                 285

Arg Asp Glu Lys Val Lys Val Leu Gln Ser Val Asn Pro Ile Lys Asp
290                 295                 300

Glu Glu Val Val Leu Gly Gln Tyr Gln Gly Tyr Lys Glu Asp Pro Thr
305                 310                 315                 320

Val Pro Asp Asp Ser Asn Thr Pro Thr Phe Ala Ser Ile Val Leu Arg
                325                 330                 335

Val His Asn Glu Arg Trp Glu Gly Val Pro Phe Ile Leu Lys Ala Gly
            340                 345                 350

Lys Ala Leu Asn Ser Arg Lys Ala Glu Ile Arg Val Gln Phe Lys Asp
            355                 360                 365

Val Pro Gly Asp Ile Phe Lys Cys Lys Lys Gln Gly Arg Asn Glu Phe
370                 375                 380

Val Ile Arg Leu Gln Pro Ser Glu Ala Met Tyr Met Lys Leu Thr Val
385                 390                 395                 400

Lys Lys Pro Gly Leu Glu Met Ala Thr Glu Gln Ser Glu Leu Asp Leu
                405                 410                 415

Ser Tyr Gly Met Arg Tyr Gln Asp Val Lys Ile Pro Glu Ala Tyr Glu
            420                 425                 430

Arg Leu Ile Leu Asp Thr Ile Arg Gly Asp Gln Gln His Phe Val Arg
            435                 440                 445

Arg Asp Glu Leu Lys Ala Ala Trp Gln Ile Phe Thr Pro Leu Leu His
450                 455                 460

Asp Ile Asp Ala Gly Lys Leu Lys Ala Val Ser Tyr Lys Pro Gly Ser
465                 470                 475                 480

Arg Gly Pro Lys Glu Ala Asp Glu Leu Ser Glu Lys Val Gly Tyr Met

```
                485                 490                 495
Gln Thr His Gly Tyr Ile Trp Ile Pro Pro Thr Leu Ala
            500                 505

<210> SEQ ID NO 16
<211> LENGTH: 505
<212> TYPE: PRT
<213> ORGANISM: Rice

<400> SEQUENCE: 16

Met Ser Gly Gly Ser Pro Arg Ser Arg Ser Ser Phe Asn Ser
 1               5                  10                  15

Leu Ser Arg Asp Leu Glu Leu Pro Ser Glu Gln Gly Cys Leu Ser Val
            20                  25                  30

Ile Val Leu Gly Ala Ser Gly Asp Leu Ala Lys Lys Thr Phe Pro
            35                  40                  45

Ala Leu Phe His Leu Phe Ala Gln Gly Phe Ile Gln Ser Gly Glu Val
 50                  55                  60

His Ile Phe Gly Tyr Ala Arg Ser Asn Leu Ser Asp Asp Gly Leu Arg
 65                  70                  75                  80

Glu Arg Ile Arg Gly Tyr Leu Lys Gly Ala Ser Glu Glu His Leu Ser
                 85                  90                  95

Asp Phe Leu Gln His Ile Lys Tyr Val Ser Gly Ser Tyr Asp Ser Gly
            100                 105                 110

Glu Gly Phe Glu Lys Leu Asn Lys Glu Ile Ser Glu Tyr Glu Lys Ser
        115                 120                 125

Asn Lys Ser Glu Ser Pro Arg Arg Leu Phe Tyr Leu Ala Leu Pro Pro
    130                 135                 140

Ser Val Tyr Pro Ser Val Cys Lys Met Ile Arg Thr Tyr Cys Met Asn
145                 150                 155                 160

Pro Ser Gly Trp Thr Arg Val Ile Val Glu Lys Pro Phe Gly Lys Asp
                165                 170                 175

Leu Asp Ser Ser Glu Glu Leu Ser Ala Gln Leu Gly Glu Leu Phe Asp
            180                 185                 190

Glu Asn Gln Leu Tyr Arg Ile Asp His Tyr Leu Gly Lys Glu Leu Val
        195                 200                 205

Gln Asn Leu Leu Val Leu Arg Phe Ala Asn Arg Leu Phe Leu Pro Leu
    210                 215                 220

Trp Asn Arg Asp Asn Ile Asp Asn Ile Gln Ile Val Phe Arg Glu Asp
225                 230                 235                 240

Phe Gly Thr Asp Gly Arg Gly Gly Tyr Phe Asp Gln Tyr Gly Ile Ile
                245                 250                 255

Arg Asp Ile Ile Gln Asn His Leu Leu Gln Val Phe Cys Leu Val Ala
            260                 265                 270

Met Glu Lys Pro Val Ser Leu Lys Pro Glu His Ile Arg Asp Glu Lys
        275                 280                 285

Val Lys Val Leu Gln Ser Val Asn Pro Ile Lys His Asp Glu Val Val
    290                 295                 300

Leu Gly Gln Tyr Glu Gly Tyr Lys Asp Asp Pro Thr Val Pro Asp Asp
305                 310                 315                 320

Ser Asn Thr Pro Thr Phe Ala Ser Val Val Phe Arg Val His Asn Glu
                325                 330                 335

Arg Trp Glu Gly Val Pro Phe Ile Leu Lys Ala Gly Lys Ala Leu Ser
            340                 345                 350
```

```
Ser Arg Lys Ala Glu Val Arg Val Gln Phe Lys Asp Val Pro Gly Asp
        355                 360                 365

Ile Phe Lys Cys Lys Arg Gln Gly Arg Asn Glu Phe Val Ile Arg Leu
        370                 375                 380

Gln Pro Ser Glu Ala Met Tyr Met Lys Leu Thr Val Lys Lys Pro Gly
385                 390                 395                 400

Leu Glu Met Ala Thr Glu Gln Ser Glu Leu Asp Leu Ser Tyr Gly Met
                405                 410                 415

Arg Tyr Gln Asn Val Lys Ile Pro Glu Ala Cys Glu Arg Leu Ile Leu
                420                 425                 430

Asp Thr Ile Arg Gly Asp Gln His Phe Val Arg Arg Asp Glu Leu
                435                 440                 445

Lys Ala Ala Trp Gln Ile Phe Thr Pro Leu Leu His Asp Ile Asp Glu
        450                 455                 460

Gly Lys Val Lys Ser Ile Pro Tyr Gln Pro Gly Ser Arg Gly Pro Lys
465                 470                 475                 480

Glu Ala Asp Glu Leu Ser Glu Arg Val Gly Tyr Met Gln Thr His Gly
                485                 490                 495

Tyr Ile Trp Ile Pro Pro Thr Leu Ala
        500                 505

<210> SEQ ID NO 17
<211> LENGTH: 511
<212> TYPE: PRT
<213> ORGANISM: Tobacco

<400> SEQUENCE: 17

Met Ala Ala Ser Trp Cys Ile Glu Lys Arg Gly Ser Ile Arg Leu Asp
1               5                   10                  15

Ser Phe Arg Asp Asn Asp Asn Ile Pro Glu Thr Gly Cys Leu Ser Ile
            20                  25                  30

Ile Val Leu Gly Ala Ser Gly Asp Leu Ala Lys Lys Lys Thr Phe Pro
        35                  40                  45

Ala Leu Phe Asn Leu Tyr Arg Gln Gly Phe Leu Gln Ser Asn Glu Val
    50                  55                  60

His Ile Phe Gly Tyr Ala Arg Thr Lys Ile Ser Asp Asp Leu Arg
65              70                  75                  80

Gly Arg Ile Arg Gly Tyr Leu Ser Gln Gly Lys Glu Asn Glu Glu Glu
                85                  90                  95

Val Ser Glu Phe Leu Gln Leu Ile Lys Tyr Val Ser Gly Ser Tyr Asp
            100                 105                 110

Ser Gly Glu Gly Phe Ser Leu Leu Asp Lys Ala Ile Ala Glu His Glu
        115                 120                 125

Ile Ala Lys Asn Ser Thr Glu Gly Ser Ser Arg Arg Leu Phe Tyr Phe
    130                 135                 140

Ala Leu Pro Pro Ser Val Tyr Pro Ser Val Cys Arg Met Ile Lys Asn
145                 150                 155                 160

Tyr Cys Met Asn Lys Ser Asp Leu Gly Gly Trp Thr Arg Ile Val Val
                165                 170                 175

Glu Lys Pro Phe Gly Lys Asp Leu Ala Ser Ala Glu Gln Leu Ser Ser
            180                 185                 190

Gln Ile Gly Glu Leu Phe Asp Glu Pro Gln Ile Tyr Arg Ile Asp His
        195                 200                 205

Tyr Leu Gly Lys Glu Leu Val Gln Asn Leu Leu Val Leu Arg Phe Ala
    210                 215                 220
```

```
Asn Arg Phe Phe Leu Pro Leu Trp Asn Arg Asp Asn Ile Asp Asn Ile
225                 230                 235                 240

Gln Ile Val Phe Arg Glu Asp Phe Gly Thr Glu Gly Arg Cys Gly Tyr
            245                 250                 255

Phe Asp Glu Tyr Gly Ile Ile Arg Asp Ile Ile Gln Asn Gln Leu Leu
            260                 265                 270

Gln Val Leu Cys Leu Val Ala Met Glu Lys Pro Val Ser Gln Lys Pro
            275                 280                 285

Glu His Ile Arg Asp Glu Lys Val Lys Val Leu Gln Ser Met Leu Pro
        290                 295                 300

Ile Lys Asp Glu Val Val Leu Gly Gln Tyr Glu Gly Tyr Lys Asp
305                 310                 315                 320

Asp Pro Thr Val Pro Asp Asn Ser Asn Thr Pro Thr Phe Ala Thr Met
                325                 330                 335

Val Leu Arg Ile His Asn Glu Arg Trp Glu Gly Val Pro Phe Ile Met
            340                 345                 350

Lys Ala Gly Lys Ala Leu Asn Ser Arg Lys Ala Glu Ile Arg Val Gln
            355                 360                 365

Phe Lys Asp Val Pro Gly Asp Ile Phe Arg Cys Lys Lys Gln Gly Arg
    370                 375                 380

Asn Glu Phe Val Ile Arg Leu Gln Pro Ser Glu Ala Met Tyr Met Lys
385                 390                 395                 400

Leu Thr Val Lys Lys Pro Gly Leu Glu Met Ser Thr Val Gln Ser Glu
                405                 410                 415

Leu Asp Leu Ser Tyr Arg Gln Arg Tyr Gln Gly Val Val Ile Pro Glu
            420                 425                 430

Ala Tyr Glu Arg Leu Ile Leu Asp Thr Ile Arg Gly Asp Gln Gln His
        435                 440                 445

Phe Val Arg Arg Asp Glu Leu Lys Ala Ala Trp Glu Ile Phe Thr Pro
    450                 455                 460

Leu Leu His Arg Ile Asp Asp Gly Glu Val Lys Pro Ile Pro Tyr Lys
465                 470                 475                 480

Pro Gly Ser Arg Gly Pro Ala Glu Ala Asp Glu Leu Leu Gln Asn Val
                485                 490                 495

Gly Tyr Val Gln Thr His Gly Tyr Ile Cys Ile Pro Pro Thr Leu
            500                 505                 510

<210> SEQ ID NO 18
<211> LENGTH: 515
<212> TYPE: PRT
<213> ORGANISM: Arabidopsis

<400> SEQUENCE: 18

Met Gly Ser Gly Gln Trp His Val Glu Lys Arg Ser Thr Phe Arg Asn
1               5                   10                  15

Asp Ser Phe Val Arg Glu Tyr Gly Ile Val Pro Glu Thr Gly Cys Leu
            20                  25                  30

Ser Ile Ile Val Leu Gly Ala Ser Gly Asp Leu Ala Lys Lys Lys Thr
        35                  40                  45

Phe Pro Ala Leu Phe Asn Leu Tyr Arg Gln Gly Phe Leu Asn Pro Asp
    50                  55                  60

Glu Val His Ile Phe Gly Tyr Ala Arg Thr Lys Ile Ser Asp Glu Glu
65                  70                  75                  80

Leu Arg Asp Arg Ile Arg Gly Tyr Leu Val Asp Glu Lys Asn Ala Glu
```

```
                        85                  90                  95
Gln Ala Glu Ala Leu Ser Lys Phe Leu Gln Leu Ile Lys Tyr Val Ser
                100                 105                 110

Gly Pro Tyr Asp Ala Glu Glu Gly Phe Gln Arg Leu Asp Lys Ala Ile
            115                 120                 125

Ser Glu His Glu Ile Ser Lys Asn Ser Thr Glu Gly Ser Ser Arg Arg
        130                 135                 140

Leu Phe Tyr Leu Ala Leu Pro Pro Ser Val Tyr Pro Ser Val Cys Lys
145                 150                 155                 160

Met Ile Lys Thr Cys Cys Met Asn Lys Ser Asp Leu Gly Gly Trp Thr
                165                 170                 175

Arg Ile Val Val Glu Lys Pro Phe Gly Lys Asp Leu Glu Ser Ala Glu
            180                 185                 190

Gln Leu Ser Ser Gln Ile Gly Glu Leu Phe Asp Glu Ser Gln Ile Tyr
        195                 200                 205

Arg Ile Asp His Tyr Leu Gly Lys Glu Leu Val Gln Asn Met Leu Val
    210                 215                 220

Leu Arg Phe Ala Asn Arg Phe Leu Pro Leu Trp Asn Arg Asp Asn
225                 230                 235                 240

Ile Glu Asn Val Gln Ile Val Phe Arg Glu Asp Phe Gly Thr Glu Gly
                245                 250                 255

Arg Gly Gly Tyr Phe Asp Glu Tyr Gly Ile Ile Arg Asp Ile Ile Gln
            260                 265                 270

Asn His Leu Leu Gln Val Leu Cys Leu Val Ala Met Glu Lys Pro Ile
        275                 280                 285

Ser Leu Lys Pro Glu His Ile Arg Asp Glu Lys Val Lys Val Leu Gln
    290                 295                 300

Ser Val Val Pro Ile Ser Asp Asp Glu Val Val Leu Gly Gln Tyr Glu
305                 310                 315                 320

Gly Tyr Arg Asp Asp Asp Thr Val Pro Asn Asp Ser Asn Thr Pro Thr
                325                 330                 335

Phe Ala Thr Thr Ile Leu Arg Ile His Asn Glu Arg Trp Glu Gly Val
            340                 345                 350

Pro Phe Ile Leu Lys Ala Gly Lys Ala Leu Asn Ser Arg Lys Ala Glu
        355                 360                 365

Ile Arg Ile Gln Phe Lys Asp Val Pro Gly Asp Ile Phe Arg Cys Gln
    370                 375                 380

Lys Gln Gly Arg Asn Glu Phe Val Ile Arg Leu Gln Pro Ser Glu Ala
385                 390                 395                 400

Met Tyr Met Lys Leu Thr Val Lys Gln Pro Gly Leu Asp Met Asn Thr
                405                 410                 415

Val Gln Ser Glu Leu Asp Leu Ser Tyr Gly Gln Arg Tyr Gln Gly Val
            420                 425                 430

Ala Ile Pro Glu Ala Tyr Glu Arg Leu Ile Leu Asp Thr Ile Lys Gly
        435                 440                 445

Asp Gln Gln His Phe Val Arg Arg Asp Glu Leu Lys Val Ala Trp Glu
    450                 455                 460

Ile Phe Thr Pro Leu Leu His Arg Ile Asp Lys Gly Glu Val Lys Ser
465                 470                 475                 480

Ile Pro Tyr Lys Pro Gly Ser Arg Gly Pro Lys Glu Ala Asp Gln Leu
                485                 490                 495

Leu Glu Lys Ala Gly Tyr Leu Gln Thr His Gly Tyr Ile Trp Ile Pro
            500                 505                 510
```

Pro Thr Leu
    515

<210> SEQ ID NO 19
<211> LENGTH: 122
<212> TYPE: PRT
<213> ORGANISM: Barley

<400> SEQUENCE: 19

Met Ala Ser Ala Thr Ala Ala Val Ala Ala Glu Val Ile Ser
 1               5                  10                  15

Val His Ser Leu Glu Gln Trp Thr Met Gln Ile Glu Ala Asn Thr
                20                  25                  30

Ala Lys Lys Leu Val Val Ile Asp Phe Thr Ala Ser Trp Cys Gly Pro
            35                  40                  45

Cys Arg Ile Met Ala Pro Val Phe Ala Asp Leu Ala Lys Lys Phe Pro
        50                  55                  60

Asn Ala Val Phe Leu Lys Val Asp Val Asp Glu Leu Lys Pro Ile Ala
 65                  70                  75                  80

Glu Gln Phe Ser Val Glu Ala Met Pro Thr Phe Leu Phe Met Lys Glu
                85                  90                  95

Gly Asp Val Lys Asp Arg Val Val Gly Ala Ile Lys Glu Glu Leu Thr
            100                 105                 110

Ala Lys Val Gly Leu His Ala Ala Ala Gln
        115                 120

<210> SEQ ID NO 20
<211> LENGTH: 125
<212> TYPE: PRT
<213> ORGANISM: Wheat

<400> SEQUENCE: 20

Met Ala Ala Ser Ala Ala Thr Ala Thr Ala Ala Val Gly Ala Gly
 1               5                  10                  15

Glu Val Ile Ser Val His Ser Leu Glu Gln Trp Thr Met Gln Ile Glu
                20                  25                  30

Glu Ala Asn Ala Ala Lys Lys Leu Val Val Ile Asp Phe Thr Ala Ser
            35                  40                  45

Trp Cys Gly Pro Cys Arg Ile Met Ala Pro Ile Phe Ala Asp Leu Ala
        50                  55                  60

Lys Lys Phe Pro Ala Ala Val Phe Leu Lys Val Asp Val Asp Glu Leu
 65                  70                  75                  80

Lys Ser Ile Ala Glu Gln Phe Ser Val Glu Ala Met Pro Thr Phe Leu
                85                  90                  95

Phe Met Lys Glu Gly Asp Val Lys Asp Arg Val Val Gly Ala Ile Lys
            100                 105                 110

Glu Glu Leu Thr Asn Lys Val Gly Leu His Ala Ala Gln
        115                 120                 125

<210> SEQ ID NO 21
<211> LENGTH: 122
<212> TYPE: PRT
<213> ORGANISM: Rice

<400> SEQUENCE: 21

Met Ala Ala Glu Glu Gly Val Val Ile Ala Cys His Asn Lys Asp Glu
 1               5                  10                  15

```
Phe Asp Ala Gln Met Thr Lys Ala Lys Glu Ala Gly Lys Val Val Ile
             20                  25                  30

Ile Asp Phe Thr Ala Ser Trp Cys Gly Pro Cys Arg Phe Ile Ala Pro
         35                  40                  45

Val Phe Ala Glu Tyr Ala Lys Lys Phe Pro Gly Ala Val Phe Leu Lys
 50                  55                  60

Val Asp Val Asp Glu Leu Lys Glu Val Ala Glu Lys Tyr Asn Val Glu
 65                  70                  75                  80

Ala Met Pro Thr Phe Leu Phe Ile Lys Asp Gly Ala Glu Ala Asp Lys
                 85                  90                  95

Val Val Gly Ala Arg Lys Asp Asp Leu Gln Asn Thr Ile Val Lys His
             100                 105                 110

Val Gly Ala Thr Ala Ala Ser Ala Ser Ala
             115                 120
```

<210> SEQ ID NO 22
<211> LENGTH: 126
<212> TYPE: PRT
<213> ORGANISM: Tobacco

<400> SEQUENCE: 22

```
Met Ala Ala Asn Asp Ala Thr Ser Ser Glu Glu Gly Gln Val Phe Gly
 1               5                  10                  15

Cys His Lys Val Glu Glu Trp Asn Glu Tyr Phe Lys Lys Gly Val Glu
                 20                  25                  30

Thr Lys Lys Leu Val Val Val Asp Phe Thr Ala Ser Trp Cys Gly Pro
             35                  40                  45

Cys Arg Phe Ile Ala Pro Ile Leu Ala Asp Ile Ala Lys Lys Met Pro
 50                  55                  60

His Val Ile Phe Leu Lys Val Asp Val Asp Glu Leu Lys Thr Val Ser
 65                  70                  75                  80

Ala Glu Trp Ser Val Glu Ala Met Pro Thr Phe Val Phe Ile Lys Asp
                 85                  90                  95

Gly Lys Glu Val Asp Arg Val Val Gly Ala Lys Lys Glu Glu Leu Gln
             100                 105                 110

Gln Thr Ile Val Lys His Ala Ala Pro Ala Thr Val Thr Ala
             115                 120                 125
```

<210> SEQ ID NO 23
<211> LENGTH: 114
<212> TYPE: PRT
<213> ORGANISM: Arabidopsis

<400> SEQUENCE: 23

```
Met Ala Ser Glu Glu Gly Gln Val Ile Ala Cys His Thr Val Glu Thr
 1               5                  10                  15

Trp Asn Glu Gln Leu Gln Lys Ala Asn Glu Ser Lys Thr Leu Val Val
                 20                  25                  30

Val Asp Phe Thr Ala Ser Trp Cys Gly Pro Cys Arg Phe Ile Ala Pro
             35                  40                  45

Phe Phe Ala Asp Leu Ala Lys Lys Leu Pro Asn Val Leu Phe Leu Lys
 50                  55                  60

Val Asp Thr Asp Glu Leu Lys Ser Val Ala Ser Asp Trp Ala Ile Gln
 65                  70                  75                  80

Ala Met Pro Thr Phe Met Phe Leu Lys Glu Gly Lys Ile Leu Asp Lys
                 85                  90                  95
```

Val Val Gly Ala Lys Lys Asp Glu Leu Gln Ser Thr Ile Ala Lys His
            100                 105                 110

Leu Ala

<210> SEQ ID NO 24
<211> LENGTH: 109
<212> TYPE: PRT
<213> ORGANISM: E. coli

<400> SEQUENCE: 24

Met Ser Asp Lys Ile Ile His Leu Thr Asp Asp Ser Phe Asp Thr Asp
  1               5                  10                  15

Val Leu Lys Ala Asp Gly Ala Ile Leu Val Asp Phe Trp Ala Glu Trp
             20                  25                  30

Cys Gly Pro Cys Lys Met Ile Ala Pro Ile Leu Asp Glu Ile Ala Asp
         35                  40                  45

Glu Tyr Gln Gly Lys Leu Thr Val Ala Lys Leu Asn Ile Asp Gln Asn
     50                  55                  60

Pro Gly Thr Ala Pro Lys Tyr Gly Ile Arg Gly Ile Pro Thr Leu Leu
 65                  70                  75                  80

Leu Phe Lys Asn Gly Glu Val Ala Ala Thr Lys Val Gly Ala Leu Ser
                 85                  90                  95

Lys Gly Gln Leu Lys Glu Phe Leu Asp Ala Asn Leu Ala
            100                 105

<210> SEQ ID NO 25
<211> LENGTH: 28
<212> TYPE: DNA
<213> ORGANISM: Artificial Sequence
<220> FEATURE:
<223> OTHER INFORMATION: Primer

<400> SEQUENCE: 25
atatctagaa tggcggcgtc ggcggcga                                    28

<210> SEQ ID NO 26
<211> LENGTH: 27
<212> TYPE: DNA
<213> ORGANISM: Artificial Sequence
<220> FEATURE:
<223> OTHER INFORMATION: Primer

<400> SEQUENCE: 26
atagagctct tactgggccg cgtgtag                                     27

<210> SEQ ID NO 27
<211> LENGTH: 36
<212> TYPE: DNA
<213> ORGANISM: Artificial Sequence
<220> FEATURE:
<223> OTHER INFORMATION: Primer

<400> SEQUENCE: 27
ggcgcatgcg aattcgaatt cgatatcgat cttcga                           36

<210> SEQ ID NO 28
<211> LENGTH: 27
<212> TYPE: DNA
<213> ORGANISM: Artificial Sequence
<220> FEATURE:
<223> OTHER INFORMATION: Primer

<400> SEQUENCE: 28

```
aactctagac tcggtggact gtcaatg                                              27

<210> SEQ ID NO 29
<211> LENGTH: 26
<212> TYPE: DNA
<213> ORGANISM: Artificial Sequence
<220> FEATURE:
<223> OTHER INFORMATION: Primer

<400> SEQUENCE: 29
gtaaagcttt aacaacccac acattg                                               26

<210> SEQ ID NO 30
<211> LENGTH: 34
<212> TYPE: DNA
<213> ORGANISM: Artificial Sequence
<220> FEATURE:
<223> OTHER INFORMATION: Primer

<400> SEQUENCE: 30
ccgacgccgc tgcaatcgta cttgttgccg caat                                      34

<210> SEQ ID NO 31
<211> LENGTH: 19
<212> TYPE: DNA
<213> ORGANISM: Artificial Sequence
<220> FEATURE:
<223> OTHER INFORMATION: Primer

<400> SEQUENCE: 31
ccaagaagtt cccagctgc                                                       19

<210> SEQ ID NO 32
<211> LENGTH: 23
<212> TYPE: DNA
<213> ORGANISM: Artificial Sequence
<220> FEATURE:
<223> OTHER INFORMATION: Primer

<400> SEQUENCE: 32
atagctgcga caaccctgtc ctt                                                  23

<210> SEQ ID NO 33
<211> LENGTH: 25
<212> TYPE: DNA
<213> ORGANISM: Artificial Sequence
<220> FEATURE:
<223> OTHER INFORMATION: Primer

<400> SEQUENCE: 33
catcgagaca agcacggtca acttc                                                25

<210> SEQ ID NO 34
<211> LENGTH: 24
<212> TYPE: DNA
<213> ORGANISM: Artificial Sequence
<220> FEATURE:
<223> OTHER INFORMATION: Primer

<400> SEQUENCE: 34
atatccgagc gcctcgtgca tgcg                                                 24

<210> SEQ ID NO 35
<211> LENGTH: 33
<212> TYPE: DNA
```

<213> ORGANISM: Artificial Sequence
<220> FEATURE:
<223> OTHER INFORMATION: Primer

<400> SEQUENCE: 35
agaaagcttg gtaccctccg agtgcccgcc gat                    33

<210> SEQ ID NO 36
<211> LENGTH: 48
<212> TYPE: DNA
<213> ORGANISM: Artificial Sequence
<220> FEATURE:
<223> OTHER INFORMATION: Primer

<400> SEQUENCE: 36
gaacagctcc tcgcccttgc tcacagcggt ggtgagagcc acgagggc    48

<210> SEQ ID NO 37
<211> LENGTH: 29
<212> TYPE: DNA
<213> ORGANISM: Artificial Sequence
<220> FEATURE:
<223> OTHER INFORMATION: Primer

<400> SEQUENCE: 37
cggaattcga tctagtaaca tagatgaca                        29

<210> SEQ ID NO 38
<211> LENGTH: 28
<212> TYPE: DNA
<213> ORGANISM: Artificial Sequence
<220> FEATURE:
<223> OTHER INFORMATION: Primer

<400> SEQUENCE: 38
atatctagaa tggcggcgtc ggcggcga                         28

<210> SEQ ID NO 39
<211> LENGTH: 27
<212> TYPE: DNA
<213> ORGANISM: Artificial Sequence
<220> FEATURE:
<223> OTHER INFORMATION: Primer

<400> SEQUENCE: 39
atagagctct tactgggccg cgtgtag                          27

<210> SEQ ID NO 40
<211> LENGTH: 26
<212> TYPE: DNA
<213> ORGANISM: Artificial Sequence
<220> FEATURE:
<223> OTHER INFORMATION: Primer

<400> SEQUENCE: 40
ggtctagaat ggaaactcac aaaacc                           26

<210> SEQ ID NO 41
<211> LENGTH: 26
<212> TYPE: DNA
<213> ORGANISM: Artificial Sequence
<220> FEATURE:
<223> OTHER INFORMATION: Primer

<400> SEQUENCE: 41
gggagctctc aatcactctt accctc                           26

<210> SEQ ID NO 42
<211> LENGTH: 21
<212> TYPE: DNA
<213> ORGANISM: Artificial Sequence
<220> FEATURE:
<223> OTHER INFORMATION: Primer

<400> SEQUENCE: 42
aagcctgaac tcaccgcgac g                                              21

<210> SEQ ID NO 43
<211> LENGTH: 22
<212> TYPE: DNA
<213> ORGANISM: Artificial Sequence
<220> FEATURE:
<223> OTHER INFORMATION: Primer

<400> SEQUENCE: 43
aagaccaatg cggagcatat ac                                             22

<210> SEQ ID NO 44
<211> LENGTH: 24
<212> TYPE: DNA
<213> ORGANISM: Artificial Sequence
<220> FEATURE:
<223> OTHER INFORMATION: Primer

<400> SEQUENCE: 44
caagatggat tgcacgcagg ttct                                           24

<210> SEQ ID NO 45
<211> LENGTH: 23
<212> TYPE: DNA
<213> ORGANISM: Artificial Sequence
<220> FEATURE:
<223> OTHER INFORMATION: Primer

<400> SEQUENCE: 45
atagaaggcg atgcgctgcg aat                                            23

<210> SEQ ID NO 46
<211> LENGTH: 21
<212> TYPE: PRT
<213> ORGANISM: Wheat

<400> SEQUENCE: 46

Ser Gly Pro Trp Met Cys Tyr Pro Gly Gln Ala Phe Gln Val Pro Ala
1               5                   10                  15

Leu Pro Ala Cys Arg
            20

<210> SEQ ID NO 47
<211> LENGTH: 17
<212> TYPE: PRT
<213> ORGANISM: Oat

<400> SEQUENCE: 47

Asp Ala Leu Leu Gln Gln Cys Ser Pro Val Ala Asp Met Ser Phe Leu
1               5                   10                  15

Arg

<210> SEQ ID NO 48
<211> LENGTH: 15

```
<212> TYPE: PRT
<213> ORGANISM: Wheat

<400> SEQUENCE: 48

Glu Tyr Val Ala Gln Gln Thr Cys Gly Val Gly Ile Val Gly Ser
1               5                   10                  15

<210> SEQ ID NO 49
<211> LENGTH: 14
<212> TYPE: PRT
<213> ORGANISM: Wheat

<400> SEQUENCE: 49

Asp Cys Cys Gln Gln Leu Ala Asp Ile Ser Glu Trp Cys Arg
1               5                   10

<210> SEQ ID NO 50
<211> LENGTH: 9
<212> TYPE: PRT
<213> ORGANISM: Wheat

<400> SEQUENCE: 50

Lys Phe Pro Ala Ala Val Phe Leu Lys
1               5

<210> SEQ ID NO 51
<211> LENGTH: 11
<212> TYPE: PRT
<213> ORGANISM: Wheat

<400> SEQUENCE: 51

Ile Met Ala Pro Ile Phe Ala Asp Leu Ala Lys
1               5                   10

<210> SEQ ID NO 52
<211> LENGTH: 22
<212> TYPE: DNA
<213> ORGANISM: Primer

<400> SEQUENCE: 52
tacttggaaa agagttggtc ca                                           22

<210> SEQ ID NO 53
<211> LENGTH: 24
<212> TYPE: DNA
<213> ORGANISM: Artificial Sequence
<220> FEATURE:
<223> OTHER INFORMATION: Primer

<400> SEQUENCE: 53
gattccatat tgatcaaaat atcc                                         24

<210> SEQ ID NO 54
<211> LENGTH: 24
<212> TYPE: DNA
<213> ORGANISM: Artificial Sequence
<220> FEATURE:
<223> OTHER INFORMATION: Primer

<400> SEQUENCE: 54
agtggtaaga acaaacggtt cgca                                         24

<210> SEQ ID NO 55
<211> LENGTH: 22
<212> TYPE: DNA
```

-continued

```
<213> ORGANISM: Artificial Sequence
<220> FEATURE:
<223> OTHER INFORMATION: Primer

<400> SEQUENCE: 55
cagattgtat tcagggagga ct                                              22
```

TRANSGENIC PLANTS WITH ELEVATED THIOREDOXIN LEVELS

RELATED APPLICATIONS

This application claims priority to U.S. Provisional Patent Application No. 60/307,006 filed Jul. 19, 2001 and is a continuation-in-part application of U.S. Application Ser. No. 09/538,864 filed Mar. 29, 2000, now U.S. Pat. No. 6,784,346, which claims priority to U.S. Provisional Patent application No. 60/126,736 filed Mar. 29, 1999 all of which are hereby incorporated by reference in their entirety.

FIELD OF THE INVENTION

This invention is in the field of molecular biology. In particular, this invention relates to transgenic plants that over-express thioredoxin.

BACKGROUND OF THE INVENTION

Seed germination is a critical process in establishing strong growth and, ultimately, high yields in crop plants. As such, it is important to be able to produce seeds with improved germination rates.

Some plants are utilized to produce flour. Some flours are allergenic. For example, wheat flour and food products are known to cause allergic reactions in sensitive individuals, especially children. For example, inhalation of wheat flour often causes Baker's asthma, a typical occupational allergic disease that has been known since ancient Roman times. Baker's asthma is mainly a type-I allergy in which patients have a specific IgE for the allergen protein families, which include inhibitors of heterologous alpha-amylase and trypsin. In addition to being allergenic, in some individuals food products are often difficult to digest.

There is thus a tremendous need to reduce the allergenicity of plant flour and food products. In addition, there is a need to increase the digestibility of wheat food products.

SUMMARY OF THE INVENTION

In order to meet these needs, the present invention is directed to a transgenic plant wherein at least a part of the plant includes a recombinant nucleic acid which includes a promoter active in the part of the plant and the promoter is operably linked to a nucleic acid encoding a thioredoxin polypeptide. In one format, the promoter is a seed or grain maturation-specific promoter. In the invention, the thioredoxin polypeptide includes the amino acid sequence WCGPC or WCPPC (SEQ ID NO: 1).

In one format of the invention, the part of the plant is a grain or a seed.

In another format, the promoter may be selected from rice glutelins, rice oryzins, rice prolamines, rice globulins, barley hordeins, wheat gliadins, wheat glutenins, maize zeins, maize glutelins, oat glutelins, sorghum kafirins, millet pennisetins, rye secalins, and maize embryo-specific globulin promoters.

In one particular format, the barley hordein promoter is selected from $B_1$-hordein and D-hordein promoters.

The transgenic plant may be a monocot or a dicot. Monocot plant include but are not limited to rice, barley, maize, wheat, oat, rye, sorghum, millet, triticale, turfgrass and forage grass.

In another format, the thioredoxin may be thioredoxin h.

In the transgenic plants of the invention, the recombinant nucleic acid may further include a nucleic acid encoding a signal peptide operably linked to the promoter.

The signal peptide can target expression of the thioredoxin polypeptide to an intracellular body. Representative but non-limiting signal peptides include $B_1$-hordein and D-hordein signal peptides.

The present invention is further directed to a transgenic plant wherein at least a part of the plant includes a recombinant nucleic acid which includes a promoter active in the part of the plant and the promoter is operably linked to a nucleic acid encoding a thioredoxin, glucose-6-phosphate dehydrogenase or an NADP-thioredoxin reductase (NTR) polypeptide or any combination thereof. In one format, the promoter is a seed or grain maturation-specific promoter.

The invention is further directed to a transgenic plant produced from a non-transgenic parent plant or plant cell wherein the transgenic plant includes a recombinant thioredoxin protein having the amino acid sequence WCGPC (SEQ ID NO: 1). The recombinant thioredoxin increases the in vivo reduction of thiol groups on proteins in the transgenic plant by at least 5% compared to the in vivo reduction of proteins in the non-transgenic parent plant or plant cell.

The proteins that are reduced may be selected from members of the alpha-amylase inhibitor, the alpha-amylase/trypsin inhibitor and the sulfur-rich gliadin families of proteins.

The transgenic plant of claim may be a monocot or a dicot.

The monocots may be selected from maize, rice, wheat, sorghum and barley and other moncots.

The present invention is further directed to transgenic wheat plants and products produced therefrom wherein the wheat plants overexpress thioredoxin in seed thereby effecting a significant increase in the reduction of proteins of the albumin fraction (SH as compared to S—S) of the seed. In particular, this invention is directed to transgenic wheat plants that overexpress thioredoxin wherein the overexpression of thioredoxin effects a significant increase in the reduction of members of the alpha-amylase inhibitor, the alpha-amylase/trypsin inhibitor and/or the sulfur-rich gliadin families of the seed. As a result, the wheat products of the invention are less allergenic than non-transgenic counterpart wheat products. As such, the invention is further directed to hypoallergenic wheat products produced from the transgenic wheat of the invention.

Wheat products produced from the transgenic wheat of the invention comprising reduced alpha-amylase/trypsin inhibitors exhibit a decreased ability to inhibit trypsin and an increased susceptibility to heat and digestion by trypsin. As a result, the wheat products of the invention are more digestible than non-transgenic counterpart wheat products. As such, the invention is directed to hyperdigestible wheat products produced from the transgenic wheat of the invention.

The invention is further directed to transgenic wheat grain harvested from the transgenic wheat plants of the invention. The invention is further directed to transgenic wheat flour produced from the transgenic wheat grain of the invention. The transgenic wheat flour exhibits reduced Baker's asthma inducing qualities. Furthermore, the invention is directed to wheat food products produced from the transgenic wheat flour of the invention. The wheat food products produced from the transgenic wheat flour of the invention are less allergenic and more digestible than non-transgenic counterparts.

The invention is further directed to a method of producing transgenic wheat flour with reduced baker's asthma-inducing qualities, comprising (a) transforming a wheat cell to contain a heterologous DNA segment encoding thioredoxin h wherein the thioredoxin h is operably linked to a promoter for expression of the thioredoxin h in the wheat cell; (b) growing and maintaining the wheat cell under conditions whereby a transgenic wheat plant is regenerated therefrom; (c) growing the transgenic plant under conditions whereby the DNA is expressed and the total amount of thioredoxin h in the plant is increased; (d) harvesting the wheat and (e) preparing wheat flour from the harvested wheat wherein the wheat has reduced Baker's asthma-inducing qualities.

The invention is further directed to a method of producing transgenic wheat products with reduced wheat allergy inducing qualities, comprising (a) transforming a wheat cell to contain a heterologous DNA segment encoding thioredoxin h wherein the thioredoxin h is operably linked to a promoter for expression of the thioredoxin h in the wheat cell; (b) growing and maintaining the wheat cell under conditions whereby a transgenic wheat plant is regenerated therefrom; (c) growing the transgenic plant under conditions whereby the DNA is expressed and the total amount of thioredoxin h in the plant is increased; (d) harvesting the wheat and (e) preparing wheat products from the harvested wheat wherein the wheat products have reduced wheat allergy inducing qualities.

The invention is further directed to a method of producing transgenic wheat products with an increased ease of gastrointestinal processing for sufferers of coeliac disease, comprising (a) transforming a wheat cell to contain a heterologous DNA segment encoding thioredoxin h wherein the thioredoxin h is operably linked to a promoter for expression of the thioredoxin h in the wheat cell; (b) growing and maintaining the wheat cell under conditions whereby a transgenic wheat plant is regenerated therefrom; (c) growing the transgenic plant under conditions whereby the DNA is expressed and the total amount of thioredoxin h in the plant is increased; (d) harvesting the wheat and (e) preparing wheat products from the harvested wheat wherein the wheat products have increased ease of gastrointestinal processing for sufferers of coeliac disease.

In the methods of the invention, the wheat flour comprises proteins in the albumin fraction wherein the proteins exhibit a significant increase (about 11%) in the reduction of proteins in the albumin protein fraction as compared to non-transgenic wheat.

The invention is further directed to a method of producing wheat grain from a transgenic wheat plant with a significant increase in the reduction of proteins in the albumin protein fraction of the wheat grain, comprising (a) transforming a wheat cell to contain a heterologous DNA segment encoding thioredoxin h wherein the thioredoxin h is operably linked to a promoter for expression of the thioredoxin h in the wheat cell; (b) growing and maintaining the wheat cell under conditions whereby a transgenic wheat plant is regenerated therefrom; (c) growing the transgenic plant under conditions whereby the DNA is expressed and the total amount of thioredoxin h in the plant is increased; (d) harvesting the wheat wherein the wheat grain has a significant increase in the reduction of proteins in the albumin protein fraction of the wheat grain as compared to a non-transgenic wheat plant.

The invention is further directed to a method of producing wheat grain from a transgenic wheat plant with a decrease (10–20% or more) in the abundance of members of the alpha-amylase inhibitor, the alpha-amylase/trypsin inhibitor and/or the sulfur-rich gliadin protein families comprising (a) transforming a wheat cell to contain a heterologous DNA segment encoding thioredoxin h wherein the thioredoxin h is operably linked to a promoter for expression of the thioredoxin h in the wheat cell; (b) growing and maintaining the wheat cell under conditions whereby a transgenic wheat plant is regenerated therefrom; (c) growing the transgenic plant under conditions whereby the DNA is expressed and the total amount of thioredoxin h in the plant is increased; (d) harvesting the wheat; wherein the wheat grain has a decrease (10–20% or more) in the abundance of members of alpha-amylase inhibitor, the alpha-amylase/trypsin inhibitor and/or the sulfur-rich gliadin families as compared to a nontransgenic wheat plant.

The invention is further directed to a method of producing wheat grain from a transgenic wheat plant with an altered protein distribution pattern in the albumin fraction, comprising (a) transforming a wheat cell to contain a heterologous DNA segment encoding thioredoxin h wherein the thioredoxin h is operably linked to a promoter for expression of the thioredoxin h in the wheat cell; (b) growing and maintaining the wheat cell under conditions whereby a transgenic wheat plant is regenerated therefrom; (c) growing the transgenic plant under conditions whereby the DNA is expressed and the total amount of thioredoxin h in the plant is increased; (d) harvesting the wheat wherein the wheat grain has an altered protein distribution pattern in the albumin fraction compared to a nontransgenic wheat plant. Illustrative but not limiting of the differences in protein pattern are the differences shown in FIGS. 26, 28 and 29.

The invention is further directed to a transgenic wheat plant comprising overexpressed thioredoxin h wherein the thioredoxin h is overexpressed in the wheat endosperm resulting in a change in the distribution of proteins in the albumin fraction such that the level of those in the 3.5 to 16 kDa region, including the alpha-amylase and alpha-amylase/trypsin inhibitors is decreased by 10–20% or more in the homozygote vs. the null segregant.

The invention is further directed toward transgenic wheat comprising one or more of the following peptides DCCQQLADISEWCR (SEQ ID NO: 2); EYVAQQTCGV-GIVGS (SEQ ID NO: 3); DALLQQCSPVADMSFLR (SEQ ID NO: 4) and SGPWMCYPGQAFQVPALPACR (SEQ ID NO: 5) wherein these peptides are more reduced in the transgenic wheat (SH as compared to S—S) when examined by two dimensional IEF/SDS-PAGE as compared to non-transgenic wheat plants.

BRIEF DESCRIPTION OF THE DRAWINGS

FIG. 2 shows the thioredoxin activity profile of various barley grains transformed with wheat thioredoxin gene (wtrxh).

FIG. 6 shows the nucleic acid sequence (SEQ ID NO: 6) of the $B_1$-hordein promoter and the 57 base pair $B_1$-hordein signal sequence (underlined).

FIG. 7 shows the nucleic acid sequence (SEQ ID NO: 7) of the D-hordein promoter and the 63 base pair D-hordein signal sequence (underlined).

FIG. 20 shows the barley thioredoxin h nucleotide and amino acid sequence (SEQ ID NO: 8, SEQ ID NO: 9, respectively).

FIG. 30 shows an alignment of NADP-thioredoxin reductases (NTRs) from different sources. Conserved regions in the sequences of the three plants are highlighted. a: Barley (SEQ ID NO: 10) b: Wheat (SEQ ID NO: 11) c: *Arabidopsis* (SEQ ID NO: 12) d: *E coli* (SEQ ID NO: 13).

FIG. 31 shows an alignment of G6PDHs from different sources. Conserved regions in the sequences of the five plants are highlighted. a: Barley (SEQ ID NO: 14); b: Wheat (SEQ ID NO: 15); c: Rice (SEQ ID NO: 16); d: Tobacco (SEQ ID NO: 17) and e: *Arabidopsis* (SEQ ID NO: 18).

FIG. 32 shows an alignment of H-type thioredoxins from different sources. Conserved regions in the sequences of the five plants are highlighted. a: Barley (SEQ ID NO: 19); b: Wheat (SEQ ID NO: 20); c: Rice (SEQ ID NO: 21); d: Tobacco (SEQ ID NO: 22); e: *Arabidopsis* (SEQ ID NO: 23); f: *E. coli* (SEQ ID NO: 24).

DETAILED DESCRIPTION OF THE INVENTION

Figure 1:
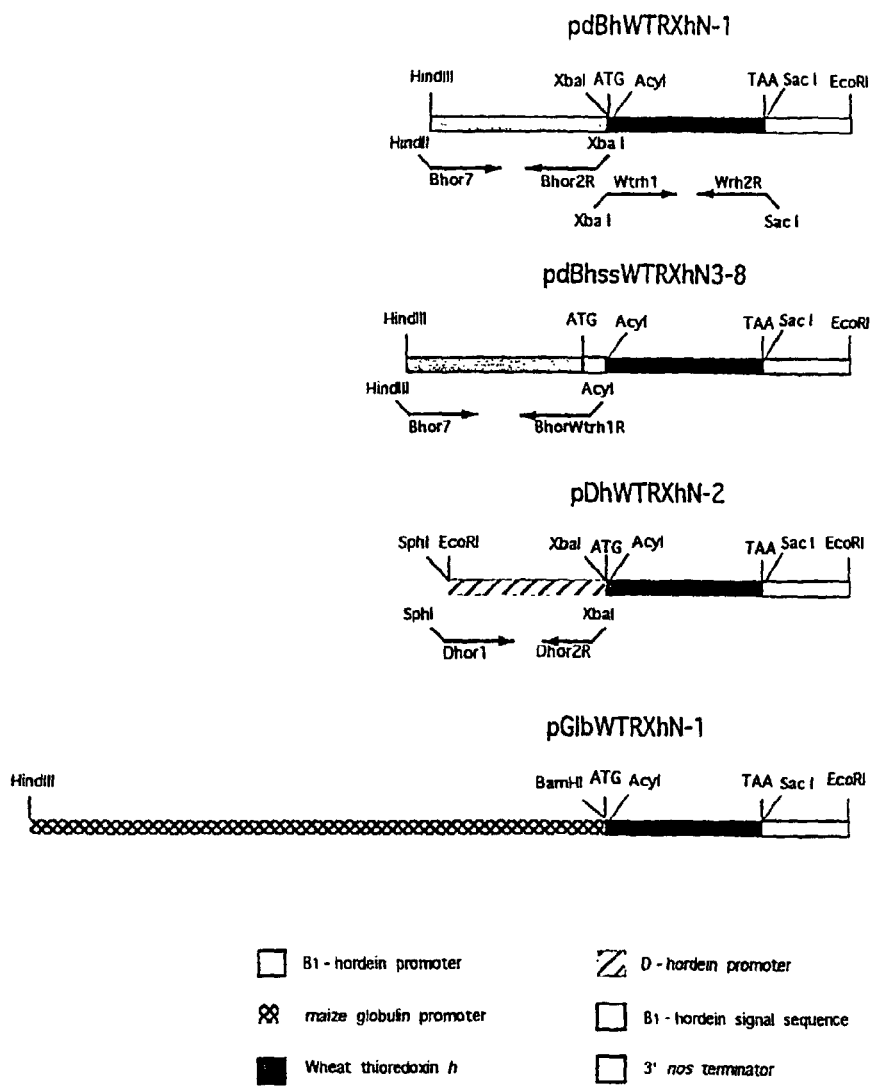
FIG. 1 shows the thioredoxin h constructs used for transformation.

Before explaining at least one embodiment of the invention in detail, it is to be understood that the invention is not limited in its application to the details of construction and the arrangement of the components set forth in the following description. The invention is capable of other embodiments or of being practiced or carried out in various ways. Also, it is to be understood that the phraseology and terminology employed herein is for the purpose of description and should not be regarded as limiting.

Throughout this disclosure, various publications, website u.r.l.s, patents and published patent specifications are referenced. The disclosures of these publications, patents and published patent specifications are hereby incorporated by reference into the present disclosure to more fully describe the state of the art to which this invention pertains.

DEFINITIONS

The practice of the present invention will employ, unless otherwise indicated, conventional techniques of immunology, molecular biology, microbiology, cell biology and recombinant DNA, which are within the skill of the art. See, e.g., Sambrook, Fritsch and Maniatis, MOLECULAR CLONING: A LABORATORY MANUAL, 2nd edition (1989); CURRENT PROTOCOLS IN MOLECULAR BIOLOGY [(F. M. Ausubel, et al. eds., (1987)]; Coligan, Dunn, Ploegh, Speicher and Wingfeld, eds. (1995) CURRENT PROTOCOLS IN PROTEIN SCIENCE (John Wiley & Sons, Inc.); the series METHODS IN ENZYMOLOGY (Academic Press, Inc.): PCR 2: A PRACTICAL APPROACH (M. J. MacPherson, B. D. Hames and G. R. Taylor eds. (1995)], Harlow and Lane, eds. (1988) ANTIBODIES, A LABORATORY MANUAL, and ANIMAL CELL CULTURE [R. I. Freshney, ed. (1987)].

Unless otherwise noted, technical terms are used according to conventional usage. Definitions of common terms in molecular biology may be found in Lewin, Genes V, published by Oxford University Press, 1994 (SBN 0-19-854287-9); Kendrew et al. (eds.), The Encyclopedia of Molecular Biology, published by Blackwell Science Ltd., 1994 (SBN 0-632-02182-9); and Robert A. Meyers (ed.), Molecular Biology and Biotechnology, a Comprehensive Desk Reference, published by VCH Publishers, Inc., 1995 (ISBN 1-56081-569-8); Ausubel et al (1987) Current Protocols in Molecular Biology, Green Publishing; Sambrook et al. (1989) Molecular Cloning: A Laboratory Manual, Cold Spring Harbor, N.Y.

In order to facilitate review of the various embodiments of the invention, the following definitions are provided:

Thioredoxin protein or Thioredoxin polypeptide: A thioredoxin protein or thioredoxin polypeptide is a protein containing the amino acid sequence WCGPC or WCPPC (SEQ ID NO: 1) that acts as a general protein disulfide reductase (reduces S—S to SH).

The present invention may be practiced using nucleic acid sequences that encode full length thioredoxin proteins such as thioredoxin h, as well as thioredoxin h derived proteins that retain thioredoxin h activity. Thioredoxin h derived proteins which retain thioredoxin biological activity include fragments of thioredoxin h, generated either by chemical (e.g. enzymatic) digestion or genetic engineering means; chemically functionalized protein molecules obtained starting with the exemplified protein or nucleic acid sequences, and protein sequence variants, for example allelic variants and mutational variants, such as those produced by in vitro mutagenesis techniques, such as gene shuffling (Stemmer et al., 1994a, 1994b). Thus, the term "thioredoxin h protein" encompasses full-length thioredoxin h proteins, as well as such thioredoxin h derived proteins that retain thioredoxin h activity all of which contain the amino acid sequence WCGPC or WCPPC (SEQ ID NO: 1).

Thioredoxin protein may be quantified in biological samples (such as seeds) either in terms of protein level, or in terms of thioredoxin activity. Thioredoxin protein level may be determined using a western blot analysis followed by quantitative scanning of the image as described elsewhere (Lozano et al., 1996). Thioredoxin activity may be quantified using a number of different methods known in the art. Preferred methods of measuring thioredoxin biological activity attributable to thioredoxin h in plant extracts include NADP/malate dehydrogenase activation (Johnson et al., 1987a, b) and reduction of 2',5'-dithiobis (2-nitrobenzoic acid) (DTNB) via NADP-thioredoxin reductase (Florencio et al., 1988; U.S. Pat. No. 5,792,506). Due to the potential for interference from non-thioredoxin h enzymes that use NADPH, accurate determination of thioredoxin h activity should preferably be made using partially purified plant extracts. Standard protein purification methods, e.g., $(NH_4)_2SO_4$ extraction or heat) can be used to accomplish this partial purification. The activity of thioredoxin h may also be expressed in terms of specific activity, i.e., thioredoxin activity per unit of protein present, as described in more detail below.

In another embodiment, thioredoxin may be expressed in terms of thioredoxin content, such as, mass/mass tissue (i.e., microgram/gram tissue) or mass/mass soluble protein (i.e., microgram/mg soluble protein).

NTR: The term "NTR" refers to proteins capable of catalyzing the reduction of thioredoxin coupled to NADPH oxidation. NTR belongs to the pyridine nucleotide-disulfide oxidoreductase family which includes glutathione reductase, lipoamide reductase, etc., which catalyze the transfer of electrons from a pyridine nucleotide via a flavin carrier to, in most cases, disulfide-containing substrates. NTRs include those sequences described in FIG. 30 and homologues thereof.

The present invention may be practiced using nucleic acid sequences that encode full length NTR proteins, as well as NTR derived proteins that retain NTR activity. NTR derived proteins which retain NTR biological activity include fragments of NTR, generated either by chemical (e.g. enzymatic) digestion or genetic engineering means; chemically functionalized protein molecules obtained starting with the exemplified protein or nucleic acid sequences, and protein sequence variants, for example allelic variants and mutational variants, such as those produced by in vitro mutagenesis techniques, such as gene shuffling (Stemmer et al., 1994a, 1994b). Thus, the term "NTR protein" encompasses full-length NTR proteins, as well as such NTR derived proteins that retain NTR activity.

Glucose-6-phosphate dehydrogenase: The term glucose-6-phosphate dehydrogenase, (G6PDH) refers to an enzyme that catalyzes the first step of the oxidative pentose phosphate pathway (OPPP), namely the conversion of glucose-6-phosphate to 6-phosphogluconolactone. Concomitantly, NADPH is generated. The main function of G6PDH is to generate NADPH for anabolic metabolism, including fatty acid, amino acid and ribose synthesis. G6PDH includes those sequences described in FIG. 31 and homologues thereof.

The present invention may be practiced using nucleic acid sequences that encode full length G6PDH proteins, as well as G6PDH derived proteins that retain G6PDH activity. G6PDH derived proteins which retain G6PDH biological activity include fragments of G6PDH, generated either by chemical (e.g. enzymatic) digestion or genetic engineering means; chemically functionalized protein molecules obtained starting with the exemplified protein or nucleic acid sequences, and protein sequence variants, for example allelic variants and mutational variants, such as those produced by in vitro mutagenesis techniques, such as gene shuffling (Stemmer et al., 1994a, 1994b). Thus, the term "G6PDH protein" encompasses full-length G6PDH proteins, as well as such G6PDH derived proteins that retain G6PDH activity.

Promoter: A regulatory nucleic acid sequence, typically located upstream (5') of a gene that, in conjunction with various cellular proteins, is responsible for regulating the expression of the gene. Promoters may regulate gene expression in a number of ways. For example, the expression may be tissue-specific, meaning that the gene is expressed at enhanced levels in certain tissues, or developmentally regulated, such that the gene is expressed at enhanced levels at certain times during development, or both.

The expression of a transgene in seeds or grains according to the present invention is preferably accomplished by operably linking a seed-specific or grain-specific promoter to the nucleic acid molecule encoding the transgene protein. In this context, "seed-specific" indicates that the promoter has enhanced activity in seeds compared to other plant tissues; it does not require that the promoter is solely active in the seeds. Accordingly, "grain-specific" indicates that the promoter has enhanced activity in grains compared to other plant tissues; it does not require that the promoter is solely active in the grain. Preferably, the seed- or grain-specific promoter selected will, at the time when the promoter is most active in seeds, produce expression of a protein in the seed of a plant that is at least about two-fold greater than expression of the protein produced by that same promoter in the leaves or roots of the plant. However, given the nature of the thioredoxin protein, it may be advantageous to select a seed- or grain-specific promoter that causes little or no protein expression in tissues other than seed or grain. In a preferred embodiment, a promoter is specific for seed and grain expression, such that, expression in the seed and grain is enhanced as compared to other plant tissues but does not require that the promoter be solely active in the grain and seed. In a preferred embodiment, the promoter is "specific" for a structure or element of a seed or grain, such as an embryo-specific promoter. In accordance with the definitions provided above, an embryo-specific promoter has enhanced activity in an embryo as compared to other parts of a seed or grain or a plant and does not require its activity to be limited to an embryo. In a preferred embodiment, the promoter is "maturation-specific" and accordingly has enhanced activity developmentally during the maturation of a part of a plant as compared to other parts of a plant and does not require its activity to be limited to the development of a part of a plant.

A seed- or grain-specific promoter may produce expression in various tissues of the seed, including the endosperm, embryo, and aleurone or grain. Any seed- or grain-specific promoter may be used for this purpose, although it will be advantageous to select a seed- or grain-specific promoter that produces high level expression of the protein in the plant seed or grain. Known seed- or grain-specific promoters include those associated with genes that encode plant seed storage proteins such as genes encoding: barley hordeins, rice glutelins, oryzins, prolamines, or globulins; wheat gliadins or glutenins; maize zeins or glutelins; maize embryo-specific promoter; oat glutelins; sorghum kafirins; millet pennisetins; or rye secalins.

In certain embodiments, the seed- or grain-specific promoter that is selected is a maturation-specific promoter. The use of promoters that confer enhanced expression during seed or grain maturation (such as the barley hordein promoters) may result in even higher levels of thioredoxin expression in the seed.

By "seed or grain-maturation" herein refers to the period starting with fertilization in which metabolizable food reserves (e.g., proteins, lipids, starch, etc.) are deposited in the developing seed, particularly in storage organs of the seed, including the endosperm, testa, aleurone layer, embryo, and scutellar epithelium, resulting in enlargement and filling of the seed and ending with seed desiccation.

Members of the grass family, which include the cereal grains, produce dry, one-seeded fruits. This type of fruit is, strictly speaking, a caryopsis but is commonly called a kernel or grain. The caryopsis of a fruit coat or pericarp surrounds the seed and adheres tightly to a seed coat. The seed consists of an embryo or germ and an endosperm enclosed by a nucellar epidermis and a seed coat. Accordingly the grain comprises the seed and its coat or pericarp. The seed comprises the embryo and the endosperm. (R. Carl Hoseney in "Principles of Cereal Science and Technology" expressly incorporated by reference in its entirety).

Allergen: An antigenic substance that induces an allergic reaction in a susceptible host. Accordingly, a susceptible host has an immune status (hypersensitivity) that results in an abnormal or harmful immune reaction upon exposure to an allergen. In a preferred embodiment, the transgenic grains of the invention have reduced allergenicity in comparison to nontransgenic grains. The immune reaction can be immediate or delayed; cell mediated or antibody mediated; or a combination thereof. In a preferred embodiment, the allergic reaction is immediate type hypersensitivity.

Sequence Identity: The similarity between two nucleic acid sequences, or two amino acid sequences is expressed in terms of sequence identity (or, for proteins, also in terms of sequence similarity). Sequence identity is frequently measured in terms of percentage identity; the higher the percentage, the more similar the two sequences are. As described above, homologs and variants of the thioredoxin nucleic acid molecules, hordein promoters and hordein signal peptides may be used in the present invention. Homologs and variants of these nucleic acid molecules will possess a relatively high degree of sequence identity when aligned using standard methods.

Methods of alignment of sequences for comparison are well known in the art. Various programs and alignment algorithms are described in: Smith and Waterman (1981); Needleman and Wunsch (1970); Pearson and Lipman (1988); Higgins and Sharp (1988); Higgins and Sharp (1989); Corpet et al. (1988); Huang et al. (1992); and Pearson et al. (1994). Altschul et al. (1994) presents a detailed consideration of sequence alignment methods and homology calculations.

The NCBI Basic Local Alignment Search Tool (BLAST) (Altschul et al., 1990) is available from several sources, including the National Center for Biotechnology Information (NCBI, Bethesda, Md.) and on the Internet, for use in connection with the sequence analysis programs blastp, blastn, blastx, tblastn and tblastx. It can be accessed at the NCBI Website. A description of how to determine sequence identity using this program is available at the NCBI website.

Homologs of the disclosed protein sequences are typically characterized by possession of at least 40% sequence identity counted over the full length alignment with the amino acid sequence of the disclosed sequence using the NCBI Blast 2.0, gapped blastp set to default parameters. The adjustable parameters are preferably set with the following values: overlap span 1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity. Proteins with even greater similarity to the reference sequences will show increasing percentage identities when assessed by this method, such as at least about 50%, at least about 60%, at least about 70%, at least about 75%, at least about 80%, at least about 90% or at least about 95% sequence identity.

Homologs of the disclosed nucleic acid sequences are typically characterized by possession of at least 40% sequence identity counted over the full length alignment with the amino acid sequence of the disclosed sequence using the NCBI Blast 2.0, gapped blastn set to default parameters. A preferred method utilizes the BLASTN module of WU-BLAST-2 (Altschul et al., 1996); set to the default parameters, with overlap span and overlap fraction set to 1 and 0.125, respectively. Nucleic acid sequences with even greater similarity to the reference sequences will show increasing percentage identities when assessed by this method, such as at least about 50%, at least about 60%, at least about 70%, at least about 75%, at least about 80%, at least about 90% or at least about 95% sequence identity.

The alignment may include the introduction of gaps in the sequences to be aligned. In addition, for sequences which contain either more or fewer amino acids than the protein encoded by the sequences in the figures, it is understood that in one embodiment, the percentage of sequence identity will be determined based on the number of identical amino acids in relation to the total number of amino acids. Thus, for example, sequence identity of sequences shorter than that shown in the figures as discussed below, will be determined using the number of amino acids in the longer sequence, in one embodiment. In percent identity calculations relative weight is not assigned to various manifestations of sequence variation, such as, insertions, deletions, substitutions, etc.

In one embodiment, only identities are scored positively (+1) and all forms of sequence variation including gaps are assigned a value of "0", which obviates the need for a weighted scale or parameters as described herein for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

As will be appreciated by those skilled in the art, the sequences of the present invention may contain sequencing errors. That is, there may be incorrect nucleotides, frameshifts, unknown nucleotides, or other types of sequencing errors in any of the sequences; however, the correct sequences will fall within the homology and stringency definitions herein.

Vector: A nucleic acid molecule as introduced into a host cell, thereby producing a transformed host cell. A vector may include one or more nucleic acid sequences that permit it to replicate in one or more host cells, such as origin(s) of replication. A vector may also include one or more selectable marker genes and other genetic elements known in the art.

Transformed: A transformed cell is a cell into which has been introduced a nucleic acid molecule by molecular biology techniques. As used herein, the term transformation encompasses all techniques by which a nucleic acid molecule might be introduced into such a cell, plant or animal cell, including transfection with viral vectors, transformation by *Agrobacterium*, with plasmid vectors, and introduction of naked DNA by electroporation, lipofection, and particle gun acceleration and includes transient as well as stable transformants.

Isolated: An "isolated" biological component (such as a nucleic acid or protein or organelle) has been substantially separated or purified away from other biological components in the cell or the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term embraces nucleic acids including chemically synthesized nucleic acids and also embraces proteins prepared by recombinant expression in vitro or in a host cell and recombinant nucleic acids as defined below.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary, join two protein-coding regions in the same reading frame. With respect to polypeptides, two polypeptide sequences may be operably linked by covalent linkage, such as through peptide bonds or disulfide bonds.

Recombinant: By "recombinant nucleic acid" herein is meant a nucleic acid that has a sequence that is not naturally occurring or has a sequence that is made by an artificial combination of two otherwise separated segments of sequence. This artificial combination is often accomplished by chemical synthesis or, more commonly, by the artificial manipulation of nucleic acids, e.g., by genetic engineering techniques, such as by the manipulation of at least one nucleic acid by a restriction enzyme, ligase, recombinase, and/or a polymerase. Once introduced into a host cell, a recombinant nucleic acid is replicated by the host cell, however, the recombinant nucleic acid once replicated in the cell remains a recombinant nucleic acid for purposes of this invention. By "recombinant protein" herein is meant a protein produced by a method employing a recombinant nucleic acid. As outlined above "recombinant nucleic acids" and "recombinant proteins" also are "isolated" as described above.

Complementary DNA (cDNA): A piece of DNA that is synthesized in the laboratory by reversed transcription of an RNA, preferably an RNA extracted from cells. cDNA produced from mRNA typically lacks internal, non-coding segments (introns) and regulatory sequences that determine transcription.

Open reading frame (ORF): A series of nucleotide triplets (codons) coding for amino acids without any internal termination codons. These sequences are usually translatable into a peptide.

Reduced: As described herein, a reduced protein is one in which the disulfide (S—S) group(s) resulting from oxidized cysteine (cystine) residues is converted to the sulfhydryl (2 SH) state by the enzymatic transfer of reducing equivalents from a cofactor (NADPH) or a protein (reduced ferredoxin) in the presence of an enzyme. Such a protein can also be reduced nonenzymatically by a chemical agent such as dithiothreitol.

Transgenic plant: As used herein, this term refers to a plant that contains recombinant genetic material not normally found in plants of this type and which has been introduced into the plant in question (or into progenitors of the plant) by human manipulation. Thus, a plant that is grown from a plant cell into which recombinant DNA is introduced by transformation is a transgenic plant, as are all offspring of that plant that contain the introduced transgene (whether produced sexually or asexually). It is understood that the term transgenic plant encompasses the entire plant and parts of said plant, for instance grains, seeds, flowers, leaves, roots, fruit, pollen, stems etc.

Purified: The term purified does not require absolute purity: rather, it is intended as a relative term. Thus, for example, a purified barley thioredoxin h protein preparation is one in which the barley thioredoxin h protein is more enriched or more biochemically active or more easily detected than the protein is in its natural environment within a cell or plant tissue. Accordingly, "purified" embraces or includes the removal or inactivation of an inhibitor of a molecule of interest. In a preferred embodiment, a preparation of barley thioredoxin h protein is purified such that the barley thioredoxin h represents at least 5–10% of the total protein content of the preparation. For particular applications, higher protein purity may be desired, such that preparations in which barley thioredoxin h represents at least 50% or at least 75% or at least 90% of the total protein content may be employed.

Ortholog: Two nucleotide or amino acid sequences are orthologs of each other if they share a common ancestral sequence and diverged when a species carrying that ancestral sequence split into two species, sub-species, or cultivars. Orthologous sequences are also homologous sequences. The term "polynucleotide", "oligonucleotide", or "nucleic acid" refers to a polymeric form of nucleotides of any length, either deoxyribonucleotides or ribonucleotides, or analogs thereof. The terms "polynucleotide" and "nucleotide" as used herein are used interchangeably. Polynucleotides may have any three-dimensional structure, and may perform any function, known or unknown. The following are non-limiting examples of polynucleotides: a gene or gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. A "fragment" or "segment" of a nucleic acid is a small piece of that nucleic acid.

Gene: A "gene" refers to a polynucleotide containing at least one open reading frame that is capable of encoding a particular protein after being transcribed and translated.

Primer: The terms "primer" and "nucleic acid primer" are used interchangeably herein. A "primer" refers to a short polyonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a polymerase and at a suitable temperature and pH. The primer may be either single-stranded or double-stranded and must be sufficiently long to prime the synthesis of the desired extension product. The exact length of the primer will depend upon many factors, including temperature, source of primer and use of the method.

Polymerase chain reaction: A "polymerase chain reaction" ("PCR") is a reaction in which replicate copies are made of a target polynucleotide using a "primer pair" or a "set of primers" consisting of an "forward" and a "reverse" primer, and a catalyst of polymerization, such as a DNA polymerase, and particularly a thermally stable polymerase enzyme. Methods for PCR are taught in U.S. Pat. Nos. 4,683,195 (Mullis) and U.S. Pat. No. 4,683,202 (Mullis et al.). All processes of producing replicate copies of the same polynucleotide, such as PCR or gene cloning, are collectively referred to herein as "amplification" or "replication".

Production of Plants with Elevated Seed Thioredoxin

Standard molecular biology methods and plant transformation techniques can be used to produce transgenic plants that produce seeds having an elevated level of thioredoxin protein. The following sections provide general guidance as to the selection of particular constructs and transformation procedures.

Constructs

The present invention utilizes recombinant constructs that are suitable for obtaining elevated expression of thioredoxin in plant seeds relative to non-transformed plant seeds. In their most basic form, these constructs may be represented as P-T, wherein P is a seed-specific promoter and T is a nucleic acid sequence encoding thioredoxin. In another embodiment, a peptide signal sequence that targets expression of the thioredoxin polypeptide to an intracellular body may be employed. Such constructs may be represented as P-SS-T, wherein SS is the signal peptide. Nucleic acid molecules that may be used as the source of each of these components are described in the Definitions section above.

Each component is operably linked to the next. For example, where the construct comprises the hordein D-promoter (P), the hordein D-signal sequence (SS) encoding the hordein signal peptide, and an open reading frame encoding, preferably, the wheat thioredoxin h protein (T), the hordein promoter is linked to the 5' end of the sequence encoding the hordein signal sequence, and the hordein signal sequence is operably linked to the 5' end of the thioredoxin open reading frame, such that C terminus of the signal peptide is joined to the N-terminus of the encoded protein.

The construct will also typically include a transcriptional termination region following the end of the encoded protein ORF. Illustrative transcriptional termination regions include the nos terminator from *Agrobacterium* Ti plasmid and the rice alpha-amylase terminator.

Standard molecular biology methods, such as the polymerase chain reaction, restriction enzyme digestion, and/or ligation may be employed to produce these constructs comprising any nucleic acid molecule or sequence encoding a thioredoxin protein or polypeptide.

General Principles of Plant Transformation

Introduction of the selected construct into plants is typically achieved using standard transformation techniques. The basic approach is to: (a) clone the construct into a transformation vector, which (b) is then introduced into plant cells by one of a number of techniques (e.g., electroporation, microparticle bombardment, *Agrobacterium* infection); (c) identify the transformed plant cells; (d) regenerate whole plants from the identified plant cells, and (d) select progeny plants containing the introduced construct.

Preferably all or part of the transformation vector will stably integrate into the genome of the plant cell. That part of the transformation vector which integrates into the plant cell and which contains the introduced P-T or P-SS-T sequence (the introduced "thioredoxin transgene") may be referred to as the recombinant expression cassette.

Selection of progeny plants containing the introduced transgene may be made based upon the detection of thioredoxin or NTR over-expression in seeds, or upon enhanced resistance to a chemical agent (such as an antibiotic) as a result of the inclusion of a dominant selectable marker gene incorporated into the transformation vector.

Successful examples of the modification of plant characteristics by transformation with cloned nucleic acid sequences are replete in the technical and scientific literature. Selected examples, which serve to illustrate the knowledge in this field of technology include:

U.S. Pat. No. 5,571,706 ("Plant Virus Resistance Gene and Methods");
U.S. Pat. No. 5,677,175 ("Plant Pathogen Induced Proteins");
U.S. Pat. No. 5,510,471 ("Chimeric Gene for the Transformation of Plants");
U.S. Pat. No. 5,750,386 ("Pathogen-Resistant Transgenic Plants");
U.S. Pat. No. 5,597,945 ("Plants Genetically Enhanced for Disease Resistance");
U.S. Pat. No. 5,589,615 ("Process for the Production of Transgenic Plants with Increased Nutritional Value Via the Expression of Modified 2S Storage Albumins");
U.S. Pat. No. 5,750,871 ("Transformation and Foreign Gene Expression in Brassica Species");
U.S. Pat. No. 5,268,526 ("Overexpression of Phytochrome in Transgenic Plants");
U.S. Pat. No. 5,780,708 ("Fertile Transgenic Corn Plants");
U.S. Pat. No. 5,538,880 ("Method for Preparing Fertile Transgenic Corn Plants");
U.S. Pat. No. 5,773,269 ("Fertile Transgenic Oat Plants");
U.S. Pat. No. 5,736,369 ("Method for Producing Transgenic Cereal Plants");
U.S. Pat. No. 5,610,049 ("Methods for Stable Transformation of Wheat");
U.S. Pat. No. 6,235,529 ("Compositions and Methods for Plant Transformation and Regeneration").

These examples include descriptions of transformation vector selection, transformation techniques and the construction of constructs designed to express an introduced transgene.

Plant Types

The transgene-expressing constructs of the present invention may be usefully expressed in a wide range of higher plants to obtain seed- or grain-specific expression of selected polypeptides. The invention is expected to be particularly applicable to monocotyledonous cereal plants including barley, wheat, rice, rye, maize, triticale, millet, sorghum, oat, forage, and turf grasses. In particular, the transformation methods described herein will enable the invention to be used with genotypes of barley including Morex, Harrington, Crystal, Stander, Moravian III, Galena, Golden Promise, Steptoe, Klages and Baronesse, and commercially important wheat genotypes including Yecora Rojo, Bobwhite, Karl and Anza.

The invention may also be applied to dicotyledenous plants, including, but not limited to, soybean, sugar beet, cotton, beans, rape/canola, alfalfa, flax, sunflower, safflower, brassica, cotton, flax, peanut, clover; vegetables such as lettuce, tomato, cucurbits, cassava, potato, carrot, radish, pea, lentils, cabbage, cauliflower, broccoli, Brussels sprouts, peppers; and tree fruits such as citrus, apples, pears, peaches, apricots, and walnuts.

Vector Construction

A number of recombinant vectors suitable for stable transformation of plant cells or for the establishment of transgenic plants have been described including those described in Weissbach and Weissbach (1989), and Gelvin et al. (1990). Typically, plant transformation vectors include one or more ORFs under the transcriptional control of 5' and 3' regulatory sequences and a dominant selectable marker with 5' and 3' regulatory sequences. The selection of suitable 5' and 3' regulatory sequences for constructs of the present invention is discussed above. Dominant selectable marker genes that allow for the ready selection of transformants include those encoding antibiotic resistance genes (e.g., resistance to hygromycin, kanamycin, bleomycin, G418, streptomycin or spectinomycin) and herbicide resistance genes (e.g, phosphinothricin acetyltransferase).

Transformation and Regeneration Techniques

Methods for the transformation and regeneration of both monocotyledonous and dicotyledonous plant cells are known, and the appropriate transformation technique will be determined by the practitioner. The choice of method will vary with the type of plant to be transformed; those skilled in the art will recognize the suitability of particular methods for given plant types. Suitable methods may include, but are not limited to: electroporation of plant protoplasts; liposome-mediated transformation; polyethylene glycol (PEG-mediated transformation); transformation using viruses; micro-injection of plant cells; micro-projectile bombardment of plant cells; vacuum infiltration; and *Agrobacterium*-mediated transformation. Typical procedures for transforming and regenerating plants are described in the patent documents listed at the beginning of this section.

Selection of Transformed Plants

Following transformation, transformants are preferably selected using a dominant selectable marker. Typically, such a marker will confer antibiotic or herbicide resistance on the seedlings of transformed plants, and selection of transformants can be accomplished by exposing the seedlings to appropriate concentrations of the antibiotic or herbicide. After transformed plants are selected and grown to maturity to allow seed set, the seeds can be harvested and assayed for over-expression of thioredoxin.

USE OF PLANTS, SEEDS OR GRAINS EXPRESSING ELEVATED LEVELS OF THIOREDOXIN

In one embodiment, the transgene protein, for example thioredoxin expressed in plants, especially seeds or grains, using the methods described herein, is used in the production and synthesis of thioredoxin. The thioredoxin transgene expressed by the recombinant nucleic acid of the invention may be harvested at any point after expression of the protein has commenced. When harvesting from the seed or grain or other part of a plant for example, it is not necessary for the seed or grain or other part of the plant to have undergone maturation prior to harvesting. For example, transgene expression may occur prior to seed or grain maturation or may reach optimal levels prior to seed or grain maturation. The transgene protein may be isolated from the seeds or grain, if desired, by conventional protein purification methods. For example, the seed or grain can be milled, then extracted with an aqueous or organic extraction medium, followed by purification of the extracted thioredoxin protein. Alternatively, depending on the nature of the intended use, the transgene protein may be partially purified, or the seed or grain may be used directly without purification of the transgene protein for food processing or other purposes.

For example, the addition of thioredoxin promotes the formation of a protein network that produces flour with enhanced baking quality. Kobrehel et al., (1994) have shown that the addition of thioredoxin to flour of non-glutenous cereal such as rice, maize, and sorghum promotes the formation of a dough-like product. Accordingly, the addition of thioredoxin expressed in seeds using the methods described herein find use in the production of flour with improved baking quality such as increased strength and/or volume.

The enhanced expression of thioredoxin also produces a seed having an altered biochemical composition. For example, enhanced thioredoxin expression produces seed with increased enzymatic activity, such as, increased pullulanase, alpha-amylase A, and beta-amylase. Enhanced thioredoxin expression also produces seed with early alpha-amylase B activation. Pullulanase ("debranching enzyme") is an enzyme that breaks down branched starch of the endosperm of cereal seeds by hydrolytically cleaving alpha-1,6 bonds. Alpha-amylases break down 1–4 linkages randomly throughout the starch molecules. These enzymes are often referred to as endo-amylases. Beta-amylase, on the other hand, leaves 1–4 linkages only at the nonreducing end of starch molecules. Beta-amylase is called an exo-amylase. Pullulanase and the alpha- and beta-amylases are enzymes fundamental to the brewing and baking industries. Pullulanase and amylases are required to break down starch in malting and in certain baking procedures carried out in the absence of added sugars or other carbohydrates. Obtaining adequate activity of these enzymes is problematic especially in the malting industry. It has been known for some time that dithiothreitol (DTT, a chemical reductant that reduces and sometimes replaces thioredoxin) activates pullulanase of cereal preparations (e.g., barley, oat, and rice flours). A method of adequately increasing the activity of pullulanase, beta-amylase and alpha-amylase A and shortening the activation time of alpha-amylase B with a physiologically acceptable system, leads to more rapid malting methods and, owing to increased sugar availability, to alcoholic beverages such as beers with reduced carbohydrate content.

Accordingly, seeds or grains with enhanced thioredoxin expression provide advantages in the production of malt and beverages produced by a fermentation process. Enhanced pullulanase and alpha-amylase A and earlier induction of alpha-amylase B in grain increases the speed and efficiency of germination, important in malting, where malt is produced having increased enzymatic activity resulting in enhanced hydrolysis of starch to fermentable carbohydrates, thereby, improving the efficiency of fermentation in the production of alcoholic beverages, for example, beer and scotch whiskey. Early alpha-amylase B activation would reduce the total time for malting by about 20%. Enhanced fermentation processes also find use in the production of alcohols that are not intended for human consumption, i.e., industrial alcohols.

In another embodiment, seed or grains with enhanced thioredoxin expression provide advantages in enhancing the onset and efficiency of germination.

The overexpression of thioredoxin in seed or grains results in an increase in the total protein. It also promotes the redistribution of proteins to the most soluble albumin/globulin fraction and the production of flour and other food products, feed, and beverages with improved digestibility in comparison to edible products made from non-transformed grains. Such edible products find use in amelioration and treatment of food malabsorptive syndromes, for example, sprue or catarrhal dysentery. Sprue is a malabsorptive syndrome affecting both children and adults, precipitated by the ingestion of gluten-containing foods. Edible products that are more readily digested and readily absorbed avoid or ameliorate the disease symptoms. Edible products with improved digestibility also ameliorate or reduce symptoms associated with celiac disease in which storage proteins that are not readily digested in afficated individuals result in inflammation of the GI tract.

The expression of thioredoxin in seed grains results in the productibn of foods and other edible products with reduced aflergenicity in comparison to edible products made from non-transfonned grains. Food allergies are a significant health and nutrition problem (Lehrer et al., 1996). Up to 2% of adults and 8% of children have a food allergy causing serious symptoms including death. Wheat protein is one of the principal allergens. Food allergies are defined by the American Academy of Allergy and Immunology Committee on Adverse Reactions to Food as "an immunological reaction resulting from the ingestion of a food or a food additive" (Fenema, 1996; Lasztity, 1996). Most true allergic responses to food proteins appear to be caused by a type-I immimoglobulin E (IgE)-mediated hypersensitivity reaction (Sicherer, 1999). These responses may occur within minutes or a few hours alter eating the offending food. When the offending food is ingested by allergy-sensitive individuals the body releases histamines and other biochemloals, resulting in itchy eyes, rash or hives; runny nose; swelling of the lips, tongue, and face; itching or tightness of the throat abdominal pain; nausea; diarrhea; and shortness of breath. Some individuals have sever, anaphylactic reactions, resulting in approximately 135 deaths per year in the United States. In the U.S. over 2,500 emergency rooms visits per year are allergy-related. There is no cure for food allergies, only avoidance of the food will prevent symptoms. For example, patients with wheat allergy must avoid wheat- or gluten-containing foods; wheat gluten is a very common ingredient in many processed foods (Marx et al., 1999)."

A feature common to many allergens is the presence of one or more disulfide bonds that contribute to the resistance of allergens to digestion (Astwood et al., 1996), allowing them to be mostly intact when they react with the small intestine where they are presented to mucosal cells that mount an IgE immune response. The major allergens were found to be insoluble storage proteins, gliadins and glutenins. The soluble storage proteins, albumins and globulins were considerably weaker (Buchanan et al., 1997). Allergenicity of these proteins is substantially decreased after thioredoxin treatment and disulfide bond reduction.

Edible products, for example, bread, cookies, dough, thickeners, beverages, malt, pasta, food additives, including animal feeds, made using the transgenic plants or parts of a transgenic plant of the invention have decreased allergenicity and accordingly can be used to in the treatment of an allergic response. By "treatment" or "alleviating" symptoms herein is meant prevention or decreasing the probability of symptoms.

Increased digestibility of seeds or grains also provides wider consumption of grains by man and animals who otherwise can not consume such grains. For example, sorghum is the world's fifth leading grain in terms of metric tons after wheat, rice, maize, and barley and third in production in the Untied States after maize and wheat. The use of sorghum is constrained in part because of the difficulty associated with the digestibility of its protein and starch compared to other grains. This difficulty with the digestibility of sorghum protein and starch has to do with the structure of the seed and the manner in which the proteins are associated with the starch. The digestibility of the starch flour from sorghum cultivars is 15–25% lower in digestibility than, for example, maize. Perhaps more notable is the fact that, unlike other grains, the indigestibility of unprocessed sorghum flour increases dramatically after boiling in water, a common practice in Africa. A study with human subjects showed that protein digestibility in cooked sorghum porridge can be as low as 46%, whereas the percent digestibility for cooked wheat, maize, and rice was 81%, 73%, and 66% respectively (Mertz et al. 1984; MacLean et al., 1981). Exogenous addition of reducing agents increases the digestibility of the starch (Hamaker et al., 1987). However, the efficacy of manipulating the thioredoxin system in vivo in the seed by expressing increased amounts of thioredoxin in a manner which does not adversely affect plant development or morphology had not previously been demonstrated. Accordingly, the transgenic plants of the invention provide wider use of seeds or grains as food sources by increasing the digestibility of the starch and/or protein component. The transgenic seeds or grains of the present invention also provide the advantage of increasing the digestibility of food products for human and feed for animals made of these grains without the addition of exogenous reducing agents. In addition, the increased digestibility results in greater utilization of the food or feed, i.e., a human or animal consuming an edible product comprising a transgenic seed or grain of the invention or an extract thereof more efficiently absorbs nutrients and therefore requires to consume less in comparison to a non-transgenic food product. In another embodiment the transgenic seed, grain or extracts thereof of the present invention and extracts or food products thereof are used as a food or feed additives. For example, an extract or flour or malt produced from a transgenic seed or grain of the invention is added to a non-transgenic food or feed product to improve the digestibility or decrease the allergenicity of the nontransgenic food product or to improve the quality of the total food product, such as, by increasing the strength and/or volume of the food product.

This invention will be better understood by reference to the following non-limiting examples.

EXAMPLES

Example 1

Expression of Wheat Thioredoxin h (WTRXh) in Transgenic Barley

Four different DNA constructs were produced, each containing a 384-bp wtrxh fragment encoding the 13.5-KDa WTRXh protein. The four constructs are illustrated in FIG. 1 and described below. Each construct comprised the 384-bp wtrxh fragment operably linked to a seed-specific promoter (either the barley endosperm-specific D-hordein or $B_1$-hordein promoters or the maize embryo-specific globulin promoter). An additional construct comprised the 384-bp wtrxh fragment operably linked to the $B_1$-hordein promoter and the $B_1$-hordein signal sequence (FIG. 6). The transformation vector used included the bar gene, conferring resistance to bialaphos. Twenty-eight independent regenerable barley lines were obtained after bialaphos selection and all were PCR-positive for the bargene. The presence of the wtrxh gene was confirmed in the genome of the 28 independent lines by PCR and DNA hybridization analyses. The expression of the WTRXh protein was assessed by western blot analysis, using purified wheat thioredoxin as a control. The WTRXh expressed in transgenic barley had a molecular mass that differed from native barley TRXh but was identical to WTRXh. The WTRXh was found to be highly expressed in developing and mature seed of transgenic barley plants although levels of expression varied among the transgenic events. On average, higher expression levels were observed in lines transformed with the DNA construct containing the $B_1$-hordein promoter plus the signal peptide sequence than the same promoter without the signal peptide sequence. The WTRXh purified from transgenic barley seed was confirmed to be biochemically active.

Materials and Methods

Plant Materials for Transformation

A two-rowed spring cultivar of barley, Golden Promise, was grown in growth chambers as described previously (Wan and Lemaux, 1994; Lemaux et al., 1996).

Construction of Wheat Thioredoxin h Expression Vectors and DNA Sequencing

Expression vectors were constructed containing the wheat thioredoxin h gene (wtrxh) driven by the barley endosperm-specific $B_1$- or D-hordein promoter or the maize embryo-specific globulin promoter. The plasmids were constructed as follows.

(1) pDhWTRXN-2: A 384-bp wtrxh coding region was amplified by PCR from pTaM13.38 (Gautier et al, 1998). This plasmid contained a cDNA of wtrxh, which was used as a template, creating XbaI and SacI sites with the following primers WTRXh1 (5'-atatctaga<u>ATGGCGGCGTCGGCGGCGA</u>) (SEQ ID NO: 25) and WTRXh2R (5'-atagagctc<u>TTACTGGGCCGCGTGTAG</u>) (SEQ ID NO: 26), respectively (FIG. 1). Small letters in the primer denote a restriction enzyme site for subcloning of the DNA fragment containing the wtrxh gene; underlined letters denote wtrxh sequences. The ATG initiation codon for wtrxh expression was included in the WTRXh1 primer. PCR reactions were performed on a thermocycler (M J Research Inc., Watertown, Mass.) using recombinant Taq DNA polymerase (Promega, Madison, Wis.) in a 100-µl reaction volume. The reaction buffer contained 10 mM Tris-HCl (pH 9.0), 50 mM KCl, 1.5 mM $MgCl_2$, 0.1% Triton-X-100, and 50 µM of each deoxyribonucleoside triphosphate. PCR conditions utilized 25 cycles of 94° C. for 1 min, 55° C. for 1 min and 72° C. for 2 min, with a final extension step at 72° C. for 7 min. The wtrxh fragment, which was amplified with the primers WTRXh1 and WTRXh2R, was purified from a 0.7% agarose gel using a QIAquick® gel extraction kit (Qiagen Inc., Chatsworth, Calif.), digested with XbaI and SacI and ligated into XbaI/SacI-digested pUC19 to generate the pWTRXh-1 plasmid. Nucleotide sequences of the PCR-amplified wtrxh coding region fragment were determined by the dideoxynucleotide chain termination method using Sequenase according to manufacturer's instructions (United States Biochemical, Cleveland, Ohio) with double-stranded plasmid templates and regularly spaced primers.

pDhWTRXN-2 was made by replacing the uidA gene in pDhGN-2 (containing barley endosperm-specific D-hordein promoter (FIG. 7) and nos 3' terminator) with the XbaI/SacI fragment containing the wtrxh coding sequence from pWTRXh-I, which contains the PCR-amplified wtrxh coding sequence in pUC19. To construct pDhGN-2, a 0.4-kb D-hordein promoter was amplified by PCR from pDll-Hor3 (Sørenson et al., 1996; Cho et al., 1999a). This plasmid contained the D-hordein promoter sequence, which was used as a template, creating SphI and XbaI sites with the following primers: Dhor1 (5'-ggcgcatgcgaattc GAATTCGATATCGATCTTCGA-3') (SEQ ID NO: 27) and Dhor2 (5'-aactctagaCTCGGTGGACTGTCAAG-3') (SEQ ID NO: 28), respectively. Small letters in the primers contain restriction enzyme sites for subcloning of the DNA fragment containing the D-hordein promoter; underlined letters denote D-hordein promoter sequences. The PCR amplified D-hordein promoter fragment was digested with SphI and XbaI and replaced with the cauliflower mosaic 35S (CaMV 35S) promoter in p35SGN-3 to generate the pDhGN-2 plasmid, p35SGN-3 was made by ligating the 3.0-kb SphI-EcoRI fragment containing the CaMV 35S promoter, uidA (beta-glucuronidase, gus) gene and nos into the SphI/EcoRI-digested pUC18.

(2) pdBhWTRXN-1: The construction of pdBh-WTRXN-1 started by using pBhWTRXN-1, pBhWTRXN-1 was made by replacing the uidA gene in pBhGN-1, which contains uidA driven by the barley endosperm-specific $B_1$-hordein promoter and terminated by the nos3' terminator, with the XbaI/SacI fragment from pWTRXh-1, which contains the wtrxh coding sequence. The 120-bp HindIII-5' $B_1$-hordein flanking region was deleted from the pBh-WTRXN-1 and religated to make the pdBhWTRXN-1 construct.

(3) pdBhssWTRXN3-8: Primers Bhor7 (5'-GTAAAGCTTTAACAACCCACACATTG) (SEQ ID NO: 29) and BhorWTRXhIR (5'-CCGACGCCGCTGCAATCGTACTTGTTGCCGCAAT) (SEQ ID NO: 30) containing HindIII and AcyI sites, respectively, were used for amplification of a 0.49-kb $B_1$-hordein 5'-region, which included the $B_1$-hordein signal peptide sequence (FIG. 6). A λ2-4/HindIII plasmid containing a genomic clone of $B_1$-hordein (Brandt et al., 1985; Cho and Lemaux, 1997) was used as a template for the amplification. The primer BhorWTRXhI R is an overlapping primer, which contains the wtrxh coding sequence (underlined) and a partial signal peptide sequence from the $B_1$-hordein promoter, but lacks the ATG initiation codon for wtrxh. pdBh-ssWTRXN3-8 was made by replacing the D-hordein promoter (FIG. 7) in pDhWTRXN-2 with the 0.49-kb PCR-amplified HindIII/AcyI fragment, which contains the $B_1$-hordein promoter, its signal peptide sequence and the junction region from the 5' TRXh gene. Thus, construct pdBhssWTRXN3-8 contains the barley endosperm-specific BI-hordein promoter with its signal peptide sequence (FIG. 6), wtrxh and nos (FIG. 1). The signal peptide sequence containing the ATG initiation codon was directly combined with the sequence of wtrxh, with no extra amino acid sequences being introduced between the two. This ensures that the WTRXh protein has a precise cleavage site in the lumen of the endoplasmic reticulum (ER). The authenticity of a PCR-amplified fragment from the chimeric product was confirmed by DNA sequencing.

(4) pGlblWTRXN-1: The 1.42-kb HindIII/BamHI fragment containing the maize embryo-specific globulin promoter from the ppGIblGUS plasmid (Liu and Kriz, 1996) was ligated into pBluescript II KS(+) to create HindIII and XbaI sites. pGIbWTRXN-1 was made by restricting pDh-WTRXN-2 with HindIII and XbaI in order to remove the 0.49-kb HindIII/XbaI barley D-hordein promoter from the pDhWTRXN-2. In place of the 0.49-kb HindIII/XbaI D-hordein promoter fragment (FIG. 7), the 1.42-kb HindIII/XbaI maize globulin promoter was ligated into the HindIII/XbaI digested pDhWTRXN-2 to form the pGIbWTRXN-1 plasmid.

Stable Barley Transformation

Stable transgenic lines of barley expressing WTRXh driven by the $B_1$-hordein promoter with and without the signal peptide sequence (FIG. 6), by the D-hordein promoter (FIG. 7) and by the maize globulin promoter were obtained following modifications of published protocols (Wan and Lemaux 1994; Lemaux et al., 1996; Cho et al., 1998a–c). Whole immature embryos (IEs) (1.0–2.5 mm) were aseptically removed, placed scutellum-side down on DC callus-induction medium containing 2.5 mg/L 2,4-D and 5 μM $CuSO_4$ (Cho et al., 1998a–c). One day after incubation at $24\pm1°C$. in the dark, the IEs were transferred -scutellum-side up to DC medium containing equimolar amounts of mannitol and sorbitol to give a final concentration of 0.4 M. Four hours after treatment with the osmoticum, the IEs were used for bombardment. Gold particles (1.0 um) were coated with 25 μg of a 1:1 molar ratio of pAHC20 (Christensen and Quail, 1996) and one of the following plasmids, pdBh-WTRXN-1, pdBhssWTRXN3-8, pDhWTRXN-2 and pGl-bWTRXN-1. The microprojectiles were bombarded using a PDS-1000 He biolistic device (Bio-Rad, Hercules, Calif.) at 1100 psi. Bombarded IEs were selected on DC medium with 5 mg/L bialaphos for 2 to 3 months. Bialaphos-resistant callus was transferred onto an intermediate culturing medium (DBC2; Cho et al, 1998a–c), containing 2.5 mg/L 2,4-D, 0.1 mg/L BAP and 5.0 μM $CuSO_4$, between the selection (DC) medium plus bialaphos (Meiji Seika Kaisha, Ltd., Yokohama, Japan) and regeneration (FHG medium; Hunter, 1988) steps. The culturing after callus induction and selection on DC medium were carried out under dim light conditions (approximately 10 to 30 uE, 16 h-light) (Cho et al., 1998a–c). Regenerated shoots were transferred to Magenta boxes containing rooting medium (callus-induction medium without phytohormones) containing 3 mg/L bialaphos. When shoots reached the top of the box, plantlets were transferred to soil in the greenhouse.

Cytological Analysis

For cytological analysis of transgenic barley plants, healthy root meristems were collected from young plants grown in the greenhouse. After pretreatment at 4° C. in saturated 1-bromonaphthalene solution overnight, root meristems were fixed in 1:3 glacial acetic acid:ethanol and stored at 4° C. Root meristems were hydrolyzed in 1 M HCl at 60°C. for 5–7 min, stained in Feulgen solution and squashed on a glass slide in a drop of 1% aceto-carmine. Chromosomes were counted from at least five well-spread cells per plant.

Herbicide Application

To determine herbicide sensitivity of $T_o$ plants and their progeny, a section of leaf blade at the 4- to 5-leaf stage was painted using a cotton swab with 0.25% (v/v) Basta™ solution (starting concentration 200 g/L phophinothricin, Hoechst AG, Frankfurt, Germany) plus 0.1% Tween 20. Plants were scored 1 week after herbicide application.

Polymerase Chain Reaction (PCR) and DNA Blot Hybridization

Total genomic DNA from leaf tissues was purified as described by Dellaporta (1993). To test for the presence of wtrxh in genomic DNA of putatively transformed lines, 250 ng of genomic DNA was amplified by PCR using one of two primer sets:

```
Set 1:
WTRXh1
(5'-ATATCTAGAATGGCGGCGTCGGCGGCGA)    (SEQ ID NO:25)
and

WTRXh2R
(5'-ATAGAGCTCTTACTGGGCCGCGTGTAG); or (SEQ ID NO:26)

Set 2:
WTRXh4
(5'-CCAAGAAGTTCCCAGCTGC) and         (SEQ ID NO:31)

WTRXh5R
(5'-ATAGCTGCGACAACCCTGTCCTT).        (SEQ ID NO:32)
```

The presence of bar was determined using the primer set:
BAR5F (5'-CATCGAGACAAGCACGGTCAACTTC-3') (SEQ ID NO: 33) and
BAR1R (5'-ATATCCGAGCGCCTCGTGCATGCG) (SEQ ID NO: 34) (Lemaux et al., 1996). Amplifications were performed with Taq DNA polymerase (Promega, Madison, Wis.) in a 25-μl reaction (Cho et al., 1998a–c). Twenty-five microliters of the PCR product with loading dye were subjected to electrophoresis in a 1.0% agarose gel with ethidium bromide and photographed using exposure to UV light. Presence of 0.4- and 0.14-kb fragments was consistent with intact and truncated wtrxh fragments, respectively; an internal 0.34-kb fragment was produced from the bargene with bar primers. Homozygous lines for wtrxh were screened by PCR and western blot analysis in $T_2$ or $T_3$ plants.

For DNA hybridization analysis, 10 μg of total genomic DNA from leaf tissue of each line was digested with HindIII and SacI, separated on a 1.0% agarose gel, transferred to Zeta-Probe GT membrane (Bio-Rad, Hercules, Calif.) and hybridized with a radiolabeled wtrxh specific probe following the manufacturer's instructions. The wtrxh-containing 0.4 kb XbaI-SacI fragment from pDhWTRXN-9 was purified by QIAEX gel extraction kit (QIAGEN, Chatsworth, Calif.) and labeled with $^{32}$P-dCTP using random primers.

Western Blot Analysis

Western blot analysis was performed on seeds from selected transgenic lines as well as from control barley seeds from non-transgenic Golden Promise grown under the same conditions as the transgenic plants and from control wheat seeds of a durum wheat cultivar, cv. Monroe, or a bread wheat cultivar cv. Capitole. Whole seeds were ground to a fine powder with a mortar and pestle under liquid nitrogen. Ten to 20 seeds were used for each sample; the volume of extraction buffer (50 mM Tris HCl or phosphate buffer, pH 7.8, 0.5 mM phenylmethylsulfonyl fluoride [PMSF], 1 mM EDTA) varied from 2 to 4 ml depending on the number of seeds used and the viscosity of the extract. Grinding was continued for an additional minute after buffer addition; the mixture was then centrifuged at 14,000×g for 10 minutes and the supernatant solution was saved as the albumin-globulin fraction that contained the thioredoxin.

SDS-PAGE of the albumin-globulin fraction was performed in 12–17% polyacrylamide gradient gels at pH 8.5 (Laemmli, 1970). From each sample equal amounts of protein (~40 μg) quantitated according to Bradford (1976) were diluted 1:2 v/v in Laemmli sample buffer, boiled for 3 minutes, loaded onto gels and subjected to electrophoresis at a constant current of 15 mA Proteins were transferred to nitrocellulose at a constant voltage of 40 V for 4 hours at 4° C. using a Hoefer Transphor Transfer Unit (Alameda, CA). Nitrocellulose was blocked with 5% powdered milk in TBS for 2 hours at room temperature (RT), incubated in primary antibody for 4 hours at RT and in secondary antibody for 1 hour at RT. Primary antibody was wheat anti-thioredoxin h II Ab (Johnson et al., 1987b) diluted 1 to 500; secondary antibody was goat anti-rabbit alkaline phosphatase (Bio-Rad, Hercules Calif.) diluted 1:3000. Blots were developed in NBT/BCIP alkaline phosphatase color reagent (according to Bio-Rad instructions); gels were stained with Coomassie blue to assure transfer. Images were scanned using a Bio-Rad GelDoc 1000 (Hercules, Calif.) and analyzed using Bio-Rad Multi Analyst, version 1.0.2. All bands were scanned over the same area, using a rectangle of comparable density as background; results were expressed as % of volume scanned. The number shown represents the percent of the total volume (pixel density×area of scanned band).

WTRXh Activity Measurements

Preparation of Materials for Extraction.

Mature grains from various heterozygous and homozygous transgenic lines served as starting materials for the assay. Heterozygous lines with a D-hordein promoter were: GPDhBarWtrx-5, GPDhBarWtrx-9-1, and GPDhBarWtrx-9-2. Heterozygous lines with a B-hordein promoter and no signal sequence were: GPdBhBarWtrx-2, -5, -9, -19 and GPdBhBarWtrx-20. Heterozygous lines with a B-hordein promoter plus a signal sequence were: GPdBhssBarWtrx-2, -7, GPdBhssBarWtrx-29, GPdBhssBarWtrx-20, GPdBhssBarWtrx-14, GPdBhssBarWtrx-22. Homozygous lines with a signal sequence were: GPdBhssBarWtrx-2-17, GPdBhssBarWtrx-2-17-1, GPdBhssBarWtrx-29-3 and GPdBhssBarWtrx-29-3-2. Control materials included a non-transformed tissue culture derived line, 4-96, a transformed line containing only bar, GPBar-1, and null segregant lines, GPdBhssBarWtrx-29-11 and GPdBhssBarWtrx-29-11-10, derived from line GPdBhssBarWtrx-29.

Preparation of $(NH_4)_2SO_4$ Extracts for Gel Filtration

Approximately fifteen grams of barley grains were ground to powder in a coffee grinder and extracted with 80 ml (1:5 w/v) of buffer [(50 mM Tris-HCl buffer, pH 7.9, 1 mM EDTA, 0.5 mM PMSF], 2 mM ε-amino-n caproic acid, 2 mM benzamidine-HCl) by stirring for 3 hrs at 4° C. The slurry plus the rinse was subjected to centrifugation at 25,400×g for 20 min, the supernatant solution was decanted through glass wool, pellets were resuspended in a small volume of buffer and then clarified by centrifugation as before. The supernatant fractions were combined, an aliquot was removed and the remainder was subjected to acidification by adjusting the pH from 7.83 to 4.80 with 2 N formic acid; denatured proteins were removed by centrifugation as above prior to assay. The pH of the acidified supernatant solution was readjusted to 7.91 with 2 N $NH_4OH$ and an aliquot was removed for assay. Powdered $(NH_4)_2SO_4$ was added to a final concentration of 30% and the sample was stirred for 20 min at 4° C., followed by centrifugation as described above. The pellet was discarded. Additional $(NH_4)_2 SO_4$ was added to bring the decanted supernatant solution to 90% saturation; the sample was stirred for 16 hrs at 4° C., followed by centrifugation as described above. The supernatant solution was discarded, the 30–90% $(NH_4)_2SO_4$ pellets were re-suspended in 30 mM Tris-HCl, pH 7.9 buffer and then subjected to centrifugation at 40,000×g for 15 min to clarify. The resulting supernatant (30–90% $(NH_4)_2SO_4$ fraction) was added to dialysis tubing (6,000–8,000 MW cut-off) and exposed to solid sucrose at 4° C. to obtain a 10-fold reduction in volume. An aliquot (1 ml) of the clarified and concentrated 30–90% $(NH_4)_2SO_4$ sample was saved and the remaining sample was applied to a pre-equilibrated (30 mM Tris-HCl, pH 7.9, 200 mM NaCl) Sephadex G-50 superfine column (2.5×90 cm; ~400 mL bed volume) with a peristaltic pump at a flow rate of 0.5 mL/min. Protein was eluted with the same buffer at the same flow rate; one hundred fifty drop-fractions were collected. Selected fractions were used to measure absorbance at 280 nm using a Pharmacia Biotech Ultrospec 4000 and to assay for TRXh activity following the NADP-MDH activation protocol (see below). Active fractions were pooled, stored at 4° C., and then assayed for total NADP-MDH activation activity.

Preparation of Heat-Treated Extracts

Approximately 10 grams of barley grains were ground to powder for about 30 sec in a coffee grinder and extracted by shaking for 1 hr at room temperature in 50 mL buffer as above. The slurry plus the rinse was subjected to centrifugation at 27,000×g for 20 min and the supernatant solution decanted through glass wool. A 20 mL aliquot of each sample was heated at 65° C. until sample temperature reached 60±1° C. (~10 min). The sample was held at 60° C. for 10 additional min, followed by cooling in an ice-water bath. The cooled sample was centrifuged and the supernatant solution was concentrated by sucrose as above and stored at −20° C. Frozen samples were thawed and clarified by centrifugation at 14,000 rpm for 10 min at 4° C. Total TRXh activity was estimated on the concentrated, supernatant fractions.

NADP-Malate Dehydrogenase Activation Assay

Thioredoxin h activity was assayed as previously described (Florencio et al., 1988; Johnson et al., 1987a). Fifty to 120 µl of extract (depending on activity) was preincubated with DTT, and 0.16 to 0.32 µl of the pre-incubation mixture was used for the NADP-MDH assay. Control assays were conducted on identical fractions in the absence of NADP-MDH. Western blot analysis was conducted as described above except that 10 to 20% SDS-polyacrylamide gels were used for electrophoresis and transfer to nitrocellulose paper was for 4 hrs at 40 V.

Sequential Extraction of Multiple Protein Fractions

Ten grams of barley grain were sequentially extracted for albumin ($H_2O$-soluble), globulin (salt-soluble), hordeins (alcohol-soluble) and glutelins (Shewry et al., 1980). Barley powder was stirred with 0.5 M NaCl for 1 h at 25° C. to remove salt-soluble proteins. Two sequential hordein fractions were extracted from the residue with 50% propanol in the absence (hordein-I) and presence (hordein-II) of 2% (v/v) 2-mercaptoethanol. Glutelins were extracted from the residue with 0.05 M borate buffer, pH 10, containing 1% (v/v) 2-mercaptoethanol and 1% (v/v) sodium dodecylsulphate.

In vitro Monobromobimane (mBBr) Labeling of Proteins

Immature, mature, or germinating seeds from nontransformed and transgenic plants were ground in 100 mM Tris-HCl buffer, pH 7.9. Reactions were carried out following the protocol of Kobrehel et al, (1992). Seventy microliters of the buffer mixture containing a known amount of protein was either untreated or treated with DTT to a final concentration of 0.5 mM. After incubation for 20 min. 100 nmol of mBBr was added, and the reaction was continued for another 15 min. To stop the reaction and derivatize excess mBBr, 10 µl of 10% SDS and 100 µl of 100 mM 2-mercaptoethanol were added. The samples were applied to a 15% SDS-PAGE gel. Fluorescence of mBBr was visualized by placing gels on a light box fitted with a UV light source (365 nm). Protein determination was carried out by the Bradford dye binding method (Bradford 1976) using bovine serum albumin or gamma globulin as standards.

Assay of Pullulanase and its Inhibitor

To measure pullulanase activity, grain was germinated in a dark chamber and retained for up to 5 days at 25° C. as described (Kobrehel et al., 1992; Lozano et al., 1996). A set of plates from each line was removed for extract preparation each day. Cell-free endosperm extracts were prepared from lots of 10–20 germinated grains of equivalent root and coleoptile length within a given cohort. Endosperm was separated from the embryo and other tissues and added to Tris-HCl buffer (50 mM, pH 7.9) supplemented with 1 mM EDTA and 0.5 mM PMSF (1:3 to 1:6, wt/vol ratio of tissue to buffer depending on developmental stage). After grinding in a mortar on ice, the sample was clarified by centrifugation (10 min at 24,000×g); the supernatant fraction was recovered and stored in 0.5-ml aliquots −80° C. for pullulanase spectrophotometric or gel assays.

Pullulanase activity was determined spectrophotometrically at 534 nm by measuring dye released after 30 min at 37° C. using red pullulan (Megazyme, Bray, Ireland) as substrate in 50 mM citrate-phosphate buffer (pH 5.2) (Serre et al., 1990). Pullulanase also was assayed on native activity gels of 7.5% acrylamide, 1.5 mm thickness, containing 1% red pullulan (Furegon et al., 1994.). Gels were scanned using a Bio-Rad Gel Doc 1000 and analyzed using Bio-Rad MULTI ANALYST, version 1.0.2. Pullulanase inhibitor activity was determined on fractions heated to inactivate pullulanase (70° C. for 15 min) by measuring their ability to inhibit added purified barley malt pullulanase. Endogenous pullulanase activity was shown to be completely eliminated by this heat-treatment while the inhibitor activity was not affected (Macri et al., 1993; MacGregor et al., 1994).

Alpha-Amylase Activity in Barley Grain Overexpressing Thioredoxin h

Amylase activity from the null segregant and homozygous barley grains was analyzed during germination and early seedling growth by using gels containing starch. Native polyacrylamide electrophoresis gets [6% acrylamide, 1.5 mm thick] were prepared and developed according to the method of Laemmli (1970) except that SDS was omitted from all solutions. The separating gel contained 0.5% soluble starch (Lintner potato starch, Sigma Chemical Co., St. Louis, Mo.). Lyophilized samples were dissolved in distilled $H_2O$ and mixed 1:1 with a buffer consisting of 0.25 M Tris-HCl, pH 6.8, 50% glycerol, 0.04% bromophenol blue, and 3 mM $CaCl_2$. Fifty micrograms of sample protein were loaded in each lane. Electrophoresis was carried out at 80 milliamps per gel at 4° C. until the dye front was at the edge of the gel (usually 4 to 5 hours). After electrophoresis, the gels were incubated in 100 ml of 0.1 M succinate buffer, pH 6.0, for 1–2 hours at 37° C. The gels were then stained for 5 min in a solution containing 2.5 mM I2 and 0.5 M Kl. Gels were washed in distilled $H_2O$. Except for the white regions containing amylase activity, gels were stained dark blue.

Beta-Amylase Activity in Barley Grain Overexpressing Thioredoxin h

Extracts from dry, and germinated grain obtained as described above were used to assay beta-amylase activity using the Megazyme Beta-amylase test reagent according to the manufacturer's instruction (Megazyme, Bray, Ireland). The reagent employs high purity alpha-glucosidase and p-nitrophenyl-α-D-maltopentaose (PNPG5). On hydrolysis of p-nitrophenyl maltopentaoside to maltose and p-nitrophenyl maltotrioside by beta-amylase, the nitrophenyl trioside is immediately cleaved to glucose and free p-nitrophenol by the alpha-glucosidase present in the substrate mixture. Thus, the rate of release of p-nitrophenol relates directly to the rate of release of maltose by beta-amylase. The reaction is stopped by addition of Trizma base solution. The p-nitrophenyl maltotrioside released is followed by measuring absorbance at 410 nm.

Isoelectrofocusing (IEF)

For determination of alpha-amylase isozyme patterns, extracts from both dry and germinating grain of transformed and control (untransformed) barley were separated by electrophoresis at 4° C. [1.0 mm thick, pH 3–10 isoelectrofocusing polyacrylamide gels, using the X cell II system (NOVEX, San Diego, Calif.)]. Cathode buffer contained 20 mM arginine, and 20 mM lysine; anode buffer was 7 mM phosphoric acid. Samples were mixed 1:1 and 2×IEF sample buffer pH 3–10 (NOVEX). After sample application (20 μg/lane) gels were developed at constant voltage [100 V for 1 hr, 200 V for an additional 1 hr, and 500 V for 30 min]. IEF standards (Bio-Rad) were used to determine the pH gradient of the gels.

Multiple Antibody Probing of IEF Gels

Western blot analysis of alpha-amylase isozymes was performed using a Mini Trans-Blot Electrophoeesic Transfer Cell (Bio-Rad). Seed extracts from the null segregant and homozygous lines overexpressing wheat thioredoxin h were separated by IEF gels as described above. Proteins were transferred to nitrocellulose at a constant voltage of 100 V for 1 hr at 4° C. using 0.75% acetic acid as blotting buffer. Nitrocellulose was blocked with 5% powdered milk in Tris buffer solution (20 mM Tris-HCl, pH 7.5, supplemented with 0.15 M NaCl) for 1 hr at room temperature, incubated with primary antibody for 4 hours at room temperature and then with secondary antibody for 1 hour at room temperature. Primary antibody was anti-barley alpha-amylase B diluted 1:1000; secondary antibody was goat anti-rabbit alkaline phosphatase (Bio-Rad) diluted 1:3000. Blots were developed in NBT/BCIP alkaline phosphatase color reagent (according to Bio-Rad instructions) thereby rendering the cross-reacted alpha-amylase bluish-purple. To achieve full identity of isozyme pattern, blots were probed a second time with another primary antibody, anti-alpha-amylase A (diluted 1:1000) and the secondary antibody (as above). This time blots were developed in Naphthol Phosphate/Fast Red alkaline phosphatase color reagent (according to Bio-Rad instructions) which gave a pink stain to the alpha-amylase A. The blot shown was subject to this dual probing procedure.

Results and Discussion

Production of Transgenic Plants

One day after bombardment, the whole embryos were transferred onto DC medium with 5 mg/L bialaphos. At transfer to the second selection plate (5 mg/L bialaphos), all material from individual callusing embryos was broken into small pieces (2–4 mm) using forceps and maintained separately. During the subsequent two to five selection passages on 5 mg/L bialaphos (at 10–20 d intervals), callus pieces showing evidence of more vigorous growth were transferred to new selection plates. During the second round of selection, some pieces of callus were inhibited in growth and in some cases pieces turned brown. In general, transformed tissues were observed after three or more rounds of selection. The bialaphos-resistant tissues were transferred onto an intermediate medium, DBC2 or DBC3 (Cho et al., 1998a–c) with bialaphos (5 mg/L), and grown for 1 to 2 months before regeneration on FHG medium containing 3 mg/L bialaphos. Green plantlets were transferred into Magenta boxes containing 3 mg/L bialaphos. Twenty-eight independent putatively transformed, regenerable lines were produced after bialaphos selection (shown in Table 1).

TABLE 1

Transgenic Barley Lines Transformed with Wheat Thioredoxin h Gene.

| Plasmids for Bombardment | Transgenic Barley Line | DNA PCR ($T_0$ leaf) bar | wtrxh | TRXh Expression in $T_1$ seeds | Ploidy | Comments |
|---|---|---|---|---|---|---|
| pdBhWTRXN-1 + pAHC20 | GpdBhBarWTRX-1 | + | + | n.d. | Tetraploid | |
| | GpdBhBarWTRX-2 | + | + | + | Tetraploid | |
| | GpdBhBarWTRX-3 | + | + | + | Diploid | |
| | GpdBhBarWTRX-5 | + | + | + | Tetraploid | Sterile |
| | GpdBhBarWTRX-16 | + | − | n.d. | Tetraploid | |
| | GpdBhBarWTRX-17 | + | + | n.d. | Tetraploid | |
| | GpdBhBarWTRX-19 | + | + | + | Diploid | |
| | GpdBhBarWTRX-20 | + | + | + | Diploid | |
| | GpdBhBarWTRX-22 | + | + | + | Diploid | |
| | GpdBhBarWTRX-23 | + | + | + | Diploid | |
| pdBhssWTRXN3-8 + pAHC20 | GPdBhssBarWTRX-1 | + | − | − | Diploid | |
| | GPdBhssBarWTRX-2 | + | + | + | Diploid | Homozygous |
| | GPdBhssBarWTRX-3 | + | + | + | Diploid | |
| | GPdBhssBarWTRX-7 | + | + | + | Diploid | |
| | GPdBhssBarWTRX-9 | + | + | n.d. | Tetraploid | |
| | GPdBhssBarWTRX-11 | + | + | − | Diploid | |
| | GPdBhssBarWTRX-13 | + | + | + | Tetraploid | |
| | GPdBhssBarWTRX-14 | + | + | + | Diploid | |
| | GPdBhssBarWTRX-20 | + | + | + | Tetraploid | |
| | GPdBhssBarWTRX-21 | + | + | n.d. | Tetraploid | Sterile |
| | GPdBhssBarWTRX-22 | + | + | + | Tetraploid | |
| | GPdBhssBarWTRX-29 | + | + | + | Diploid | Homozygous |
| pDhWTRXN-2 + pAHC20 | GPDhBarWTRX-5 | + | + | + | Tetraploid | |
| | GPDhBarWTRX-7 | + | + | + | Diploid | |
| | GPDhBarWTRX-8 | + | + | + | Diploid | |

TABLE 1-continued

Transgenic Barley Lines Transformed with Wheat Thioredoxin h Gene.

| Plasmids for Bombardment | Transgenic Barley Line | DNA PCR ($T_0$ leaf) bar | wtrxh | TRXh Expression in $T_1$ seeds | Ploidy | Comments |
|---|---|---|---|---|---|---|
| | GPDBhBarWTRX-9 | + | + | + | Diploid | Homozygous |
| | GPDBhBarWTRX-22 | + | + | + | Diploid | Sterile |
| pGlbWTRXN-1 + pAHC20 | GPGlbBarWTRX-1 | + | + | + | Diploid | |

* nd.: not determined

Analysis of $T_o$ Plants and their Progeny

PCR analysis was performed using two sets of WTRXh primers and one set of BAR primers (see FIG. 1). PCR amplification resulted in 0.4-kb intact wtrxh or 0.14 kb truncated wtrxh and 0.34-kb internal bar fragments from transgenic lines. Of the 28 lines tested, 28 yielded bar fragments from $T_0$ leaf tissue and 26 produced PCR-amplified fragments for wtrxh, giving a 93% co-transformation frequency. Nine lines were transformed with pDBhWTRXN-1, eleven with pDBhssWTRXN-8, five with pDhWTRXN-2 and one with pG1bWTRXN-1 (see Table 1). Three lines (GPdBhBarWtrx-5, GPdBhssBarWtrx-21 and GPDhBarWtrx-22) were sterile. Seeds of $T_1$ plants and their progeny from selected wtrxh-positive lines were planted in order to screen for homozygous lines. Homozygous lines and null segregants were obtained from GPdBhssBarWtrx-2, -29 and GPDhBarWtrx-9 (see Table 1).

Cytological Analysis of Transgenic Plants

Chromosomes were counted in root meristem cells of independently transformed $T_0$ barley plants. Out of 28 independent transgenic lines examined. 17 lines had the normal diploid chromosome complement (2n=2x=14), while the remaining 11 lines were tetraploid (2n=4x=28) (see Table 1).

Characterization and Content of WTRXh Produced in Transgenic Seed

As discussed above, several stably transformed barley lines were obtained that express wheat thioredoxin h. As seen in FIG. 2, the stable introduction of the wtrxh linked to the $B_1$-hordein promoter with the signal peptide sequence resulted in greatly enhanced expression of active WTRXh in transgenic barley seed.

Analysis by western blot of soluble protein fractions of the three lines in which the thioredoxin gene was linked to a signal sequence (GPdBhssBarWtrx-22, GPdBhssBarWtrx-29 and GPdBhssBarWtrx-7) showed differences in the level of expression (shown in Table 2). Line GPdBhssBarWtrx-22, GPdBhssBarWtrx-29 and GPdBhssBarWtrx-7, respectively, showed 22 times, 10 times and 5.5 times more WTRXh protein than nontransformed control seeds. The analyses showed that the thioredoxin content of the null segregant (GPdBhssBarWtrx-29-11) was approximately half that of the corresponding control. The three lines generated from the construct in which the thioredoxin gene was not associated with a signal sequence were also compared to nontransformed control barley seed and they exhibited the following increases in TRXh levels as indicated by the western blot analyses: GPDhBarWtrx-9:12 times; GPDhBarWtrx-5: 6.3 times; GPdBhBarWtrx-2: 6.4 times. When probed on western blots, the transgenic lines show two bands while the control barley generally shows only one and in some cases a second minor band. Furthermore, the tissues from the transgenic lines were characterized by a band that did not correspond to either of the barley bands but did correspond to wheat thioredoxin h. These data indicate that the protein introduced by transformation is wheat thioredoxin h.

TABLE 2

Western Blot Analyses of Overexpression of Wheat Thioredoxin h in Barley.

| Barley Line | % Volume Scanned | Fold Increase (or Decrease) |
|---|---|---|
| Non-Transformed Control: | | |
| Golden Promise (GP 4-96) | 1.46 | 1.0 |
| Transformed with Signal Sequence: | | |
| GPdBhssBarWtrx-22 | 32.44 | 22 |
| GpdBhssBarWtrx-29 | 14.62 | 10 |
| GpdBhssBarWtrx-7 | 7.99 | 5.5 |
| Transformed without Signal Sequence: | | |
| GPDhBarWtrx-9 | 17.69 | 12 |
| GPDhBarWtrx-5 | 9.20 | 6.3 |
| GPdBhBarWtrx-2 | 9.29 | 6.4 |
| Null Segregant: | | |
| GPdBhssBarWtrx-29-11-10 | 0.93 | 0.64 |

The Wheat Thioredoxin h in Barley Grains is Biologically Active

Because of interference from other enzymes that oxidize NADPH, the activity of TRXh cannot be accurately assayed in crude extracts, thereby necessitating its partial purification. Partially purified extracts of the different transgenic and control lines were prepared from 15 grams of seed using ammonium sulfate fractionation and gel filtration chromatography. Activity was measured with an NADP-MDH activation assay. Profiles based on these assays show that the activity of TRXh in the transformed seed is much higher than in the nontransformed control (see FIG. 2). The activity results are summarized in Table 3.

Total WTRXh activity from the seeds of two lines transformed with the $B_1$-hordein promoter and the signal sequence (GPBhssBarWtrx-3; GPdBhssBarWtrx-29) is about 4- to 10-fold higher, respectively, than that of control, nontransformed seed. Total activity from a line transformed with the D-hordein promoter without the signal sequence (BGPDhBarWtrx-5) is only slightly higher (1.25-fold) than that of the nontransformed control (see Table 3). In the transgenics, the specific activity of thioredoxin is generally about 0.128 $A_{340\,nm}$/min/mg protein or about two fold over null segregants.

TABLE 3

Summary of Total Buffer-Extracted Protein and Total Thioredoxin Activity from Active Fraction after Gel Filtration.

| Barley Line | Total Protein, mg | Total Activity, $A_{340}$/min | Specific Activity, $A_{340}$/min/mg |
|---|---|---|---|
| Control (GP 4-96) | 102.6 (1.00)* | 7.4 (1.00)* | 0.064 (1.00)* |
| GPDhBarWtrx-5 | 171.2 (1.67) | 9.2 (1.2) | 0.054 (0.8) |
| GpdBhssBarWtrx-29 | 149.1 (1.45) | 72.0 (9.7) | 0.483 (7.5) |
| GpdBhssBarWtrx-3 | 231.3 (2.25) | 27.7 (3.7) | 0.794 (12.4) |

*Numbers in brackets are fold increase over that of the control.

The transformed barley grains analyzed so far appear to have more total buffer-extracted protein than control, non-transformed seed (Table 3).

The transformed grains have a thioredoxin content of at least about 10–15 μg thioredoxin/mg soluble protein (about 2–8 μg thioredoxin/mg tissue) or about two-fold higher than the null segregant.

Figure 3:
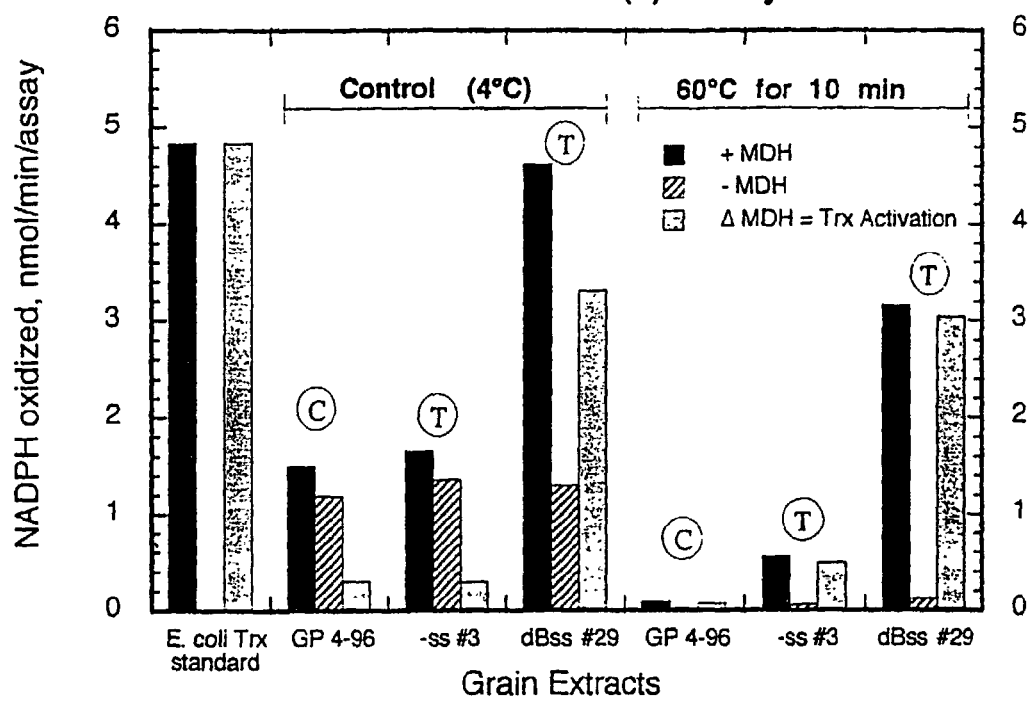
FIG. 3 shows the effects of heat treatment on thioredoxin activity of crude extracts from barley grains.

Because of the tediousness of the $(NH_4)_2SO_4$ procedure and the requirement for large quantities of seed, the original extraction procedure was modified to include a heat treatment step. This change was based on the fact that E. coli WTRXh is stable after treatment at 60° C. for 10 min (Mark and Richardson, 1976). Results on WTRXh from two different transgenic barley seeds (GPdBhBarWtrx-3, GPdBhssBarWtrx-29) showed no significant difference in activity between the heat treated and non-heat treated extracts (FIG. 3). In addition heat-treatment decreased the endogenous, nonspecific activity in this assay, thereby increasing the reliability of the measurements.

Ten different barley lines (transformed and nontransformed) were extracted using the heat-treatment step and assayed with the NADP-MDH assay; the results are summarized in Table 4. In general, total WTRXh activities in seeds from lines transformed with the B-hordein promoter and signal sequence linked to wtrxh are much higher (4- to 35-fold) than in seeds from lines transformed with the same promoter without signal sequence linked to wtrxh or in seeds from the nontransformed control (Table 4). At this point it is not known whether all expressed wheat WTRXh in barley seeds is heat stable.

TABLE 4

Relative Total Thioredoxin Activity in Different Transgenic Barley Lines.

| Line Designation | Total Protein (%) | Total Activity (%) | Specific Activity (%) |
|---|---|---|---|
| Non-transgenic control GP4-96 | 100 | 100 | 100 |
| Bar Gene Only GPBar-1 Without Signal Sequence | 92 | 120 | 131 |
| GPdBhBarWtrx-1 | 101 | 192 | 190 |
| GPdBhBarWtrx-22 | 113 | 151 | 133 |
| GpdBhBarWtrx-23 With Signal Sequence | 118 | 180 | 153 |
| GPdBhssBarWtrx-2 | 137 | 1650 | 1203 |
| GPdBhssBarWtrx-14 | 122 | 1723 | 1418 |
| GPdBhssBarWtrx-20 | 147 | 440 | 299 |
| GPdBhssBarWtrx-22 | 154 | 3470 | 2245 |
| GPdBhssBarWtrx-29 | 108 | 1316 | 1219 |

One hundred percent of (a) total protein, jg; (b) total activity, nmol/min; and (c) specific activity, nmol/min/mg protein of the non-transgenic control are: (a) 116.4; (b) 175.38; (c) 1.52, respectively.

One hundred percent of (a) total protein, mg; (b) total activity, nmol/min; and (c) specific activity, nmol/min/mg protein of the non-transgenic control are: (a) 116.4; (b) 157.38; (c) 1.52 respectively.

Of the stably transformed lines that expressed wheat thioredoxin h, on average, its level was found to be higher in transformants that had the signal peptide-containing constructs than to those that did not (Table 4). Western blot analysis of soluble protein fractions from heterozygous mixtures of seeds from three of the lines, GPdBhssBarWtrx-7, GPdBhssBarWtrx-29, and GPdBhssBarWtrx-22 showed 5.5 times, 10 times, and 22 times more thioredoxin h, respectively, than nontransformed control grain (Table 2). The thioredoxin content of the null segregant (GPdBhssBar-Wtrx-29-11-10) was about half that of the corresponding, nontransformed control.

Figure 4:
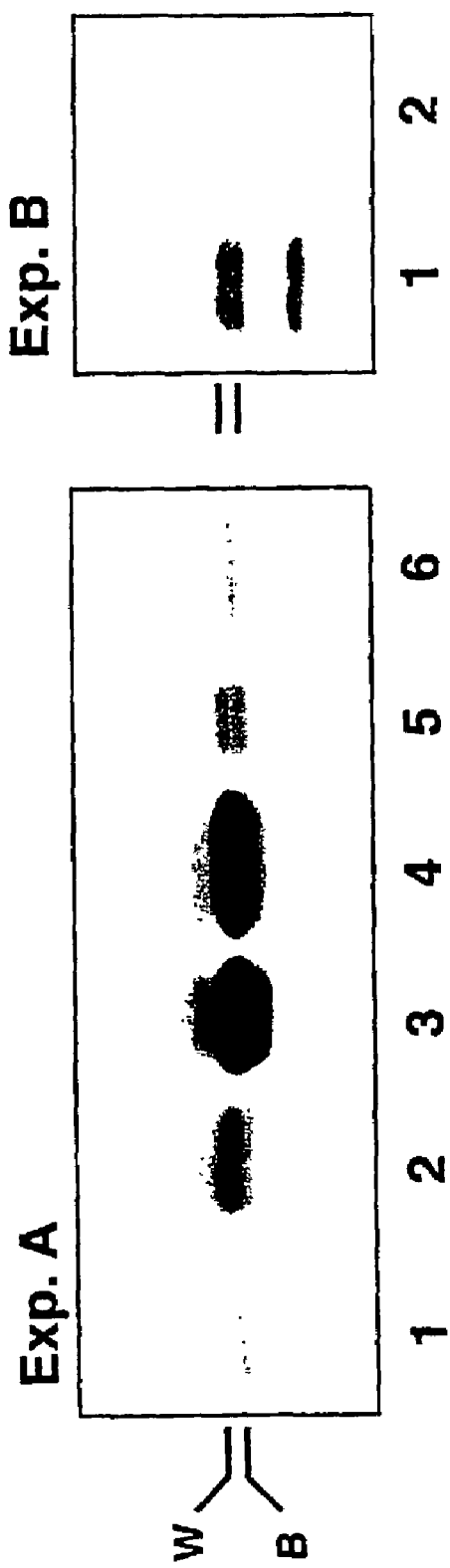
FIGS. 4A–B shows a western blot analysis of extract from segregating $T_1$ barley grain of stable transformants containing wtrxh. Panel A: lanes 1 and 6, control barley extract (cv. Golden Promise); lane 2, bread wheat extract (*Triticum aestivum*. cv. Capitole); lane 3, extract from GPdBhss BarWtrx 22; lane 4, extract from GPdBhssBarWtrx 29; lane 5, extract from GPdBhBarWtrx 2. Panel B: lane 1, GPdBh-BaarWtrx 2; lane 2 control barley extract. W, wheat; B, barley.

Extracts from barley typically showed one immunologically reactive band (identified by B in FIG. 4A, lanes 1 and 6) but in some transfers showed a second faint, faster moving band (FIG. 4B, lane 2). Tissues from transgenic lines overexpressing wtrxh were characterized by a band that did not correspond to either of the two counterparts in barley, but rather to thioredoxin h from wheat. The difference between the overexpressed 13.5-kDa wheat and the endogenous 13.1-kDa barley thioredoxin h is particularly pronounced in the barley line transformed with the nontargeted thioredoxin h gene (FIG. 4A, line 5 and FIG. 4B, lane 1). Repeated analyses of the various transgenic lines by SDS/PAGE led to the conclusion that the band identified in FIGS. 4A–B by W corresponds to the bread wheat wtrxh introduced by barley. Independent biochemical assays with 5,5'-dithiobis(2-nitrobenzoic acid) (DTNB) (Florencio et al., 1988.) confirmed the ability of barley NTR to reduce wheat thioredoxin h (data not shown).

Figure 5:
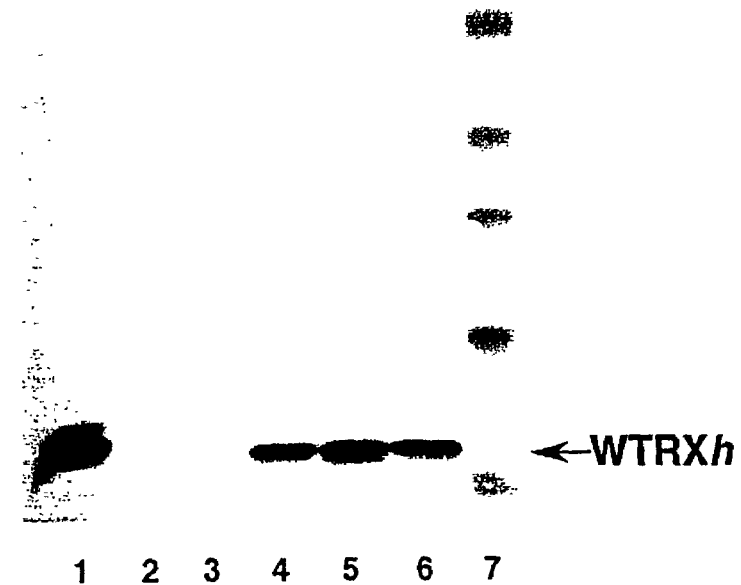
FIG. 5 shows western blot analysis of extracts of $T_1$, $T_2$ and $T_3$ barley grain transformed with wtrxh. Forty micrograms of soluble proteins extracted from 10–20 grains of each line were fractionated by SDS/PAGE. Lane 1, wheat germ thioredoxin h, lane 2, nontransgenic control of GP4-96; lane 3, null segregant $T_2$ grain of GPdBhssBarWtrx-29-11-10; lane 4, heterozygous $T_1$ grain of GPdBhssBarWtrx-29; lane 5, homozygous $T_2$ grain of GPdBhssBarWtrx-29-3; lane 6, homozygous $T_2$ grain of GPdBhssBarWtrx-29-3-2; lane 7, prestained standards (aprotinin, 9 kDa; lysozyme, 17.8 kDa; soybean trypsin inhibitor, 30.6 kDa; carbonic anhydrase, 41.8 kDa; BSA, 71 kDa).

Because of their value in assessing biochemical attributes of the grain, homozygous wtrxh lines were identified and analyzed by western blot. The two lines identified as homozygous showed both enhanced expression of thioredoxin h relative to that of their heterozygous parents and nontransformed controls. Analysis of GPdBhssBarWtrx-29-3 is shown in FIG. 5. It is noted that demonstration of the thioredoxin h present in the nontransgenic control and null segregant grains (not apparent in the exposure shown in FIG. 4) required conditions that led to overexposure of the enriched transgenic preparations. Thioredoxin in the parent heterozygous grain was shown to be biochemically active.

Pullulanase and Pullulanase Inhibitor Activity in Barley Grain Overexpressing Thioredoxin h Pullulanase is an amylolytic enzyme present in cereal grain, which has a disulfide inhibitor protein (Macri et al., 1993; MacGregor et al., 1994), the activity of which is linked to thioredoxin (Wong et al., 1995). Thioredoxin reduced by NADPH via NTR, reduces the disulfide bonds of the inhibitor, allowing the targeted pullulanase enzyme to be active. Because of this relationship, it was of interest to determine the activity of pullulanase in the thioredoxin h-overexpressing transformants.

Figure 8:
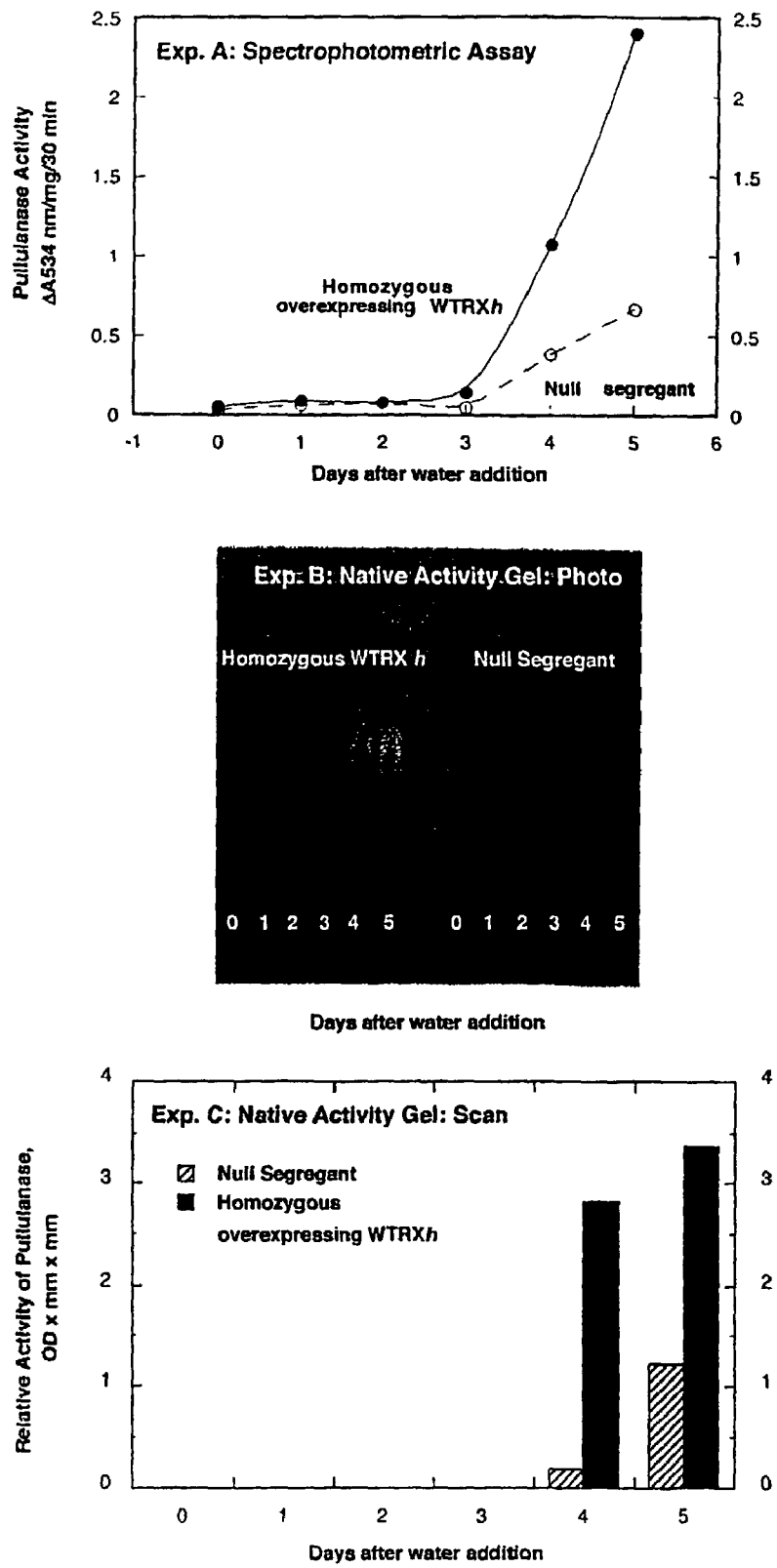
FIGS. 8A–C shows the effect of overexpressed thioredoxin h on pullulanase activity in transgenic barley grain during germination and seedling development. A homozygous line, GPdBhssBarWtrx-29-3, and a null segregant, GPdBhssBarWtrx-29-11-10, were used for the pullulanase assays. Panel A: Pullulanase was assayed spectrophotometrically be measuring the dye released from red pullulan substrate at 534 nm. Panel B: Pullulanase was separated on native 7.5% polyacrylamide gels containing the red pullulan substrate. Activity, identified by comparison with purified barley pullulanase, is seen as clear areas that developed on incubating the gel in 0.2M succinate buffer, pH 6.0, for 1 hr at 37° C. Panel C: The gel in Panel B was scanned and analyzed by integration of the activity bands.

Spectrophotometric assays (FIG. 8A) of extracts from transformed grain of a homozygous line (GPdBhssBarWtrx-29-3) overexpressing thioredoxin h showed a 3-to 4-fold increase in pullulanase activity on the fifth day after initiation of germination relative to its null segregant. Confirmatory results were obtained in a separate experiment with native activity gels. The increase in activity was apparent either when gels were viewed directly (FIG. 8B) or when the activity on the gels was assessed by scanning and integrating the clarified bands (FIG. 8C). A homozygous line isolated from a different, independent transformation event (GPdB-ssBarWtrx-2-1-15) showed a similar response (data not shown). The transgenic plants expressed a pullulanase activity of about 1–2 Absorbance units at 534 nm/30 min/mg protein, which is about two-fold higher than null segregants.

Pullulanase inhibitor activity was determined on fractions heated to inactivate pullulanase (70° C. for 15 min) by measuring the inhibition of the fractions on added purified barley malt pullulanase. The endogenous pullulanase activity was shown to be completely eliminated by this heat treatment whereas inhibitor activity was not affected (Macri et al., supra; MacGregor et al., supra). Analysis of comparable grain extracts revealed that the pullulanase inhibitor was inactive on the fourth and fifth days after water addition in both the transformant and null segregants. These results thus demonstrate that the increase in pullulanase activity observed after the third day is not caused by enhanced inactivation of the inhibitor in the transgenic grain. It is possible that thioredoxin acts either by increasing the de novo synthesis of pullulanase (Hardie et al., 1975) or by lowering the binding of the mature enzyme to the starchy endosperm. There is evidence that some of the pullulanase of the mature endosperm is present in bound form and can be solubilized by reducing conditions (Sissons et al., 1993; Sissons et al, 1994).

Alpha-Amylase Activity in Barley Grain Overexpressing Thioredoxin h

Alpha-amylase, also an amylolytic enzyme that, like pullulanase, is induced by gibberellic acid, has long been considered key to germination. The synthesis of the major (GA-dependent or B) and the minor (GA-independent or A) form of this enzyme is known to be triggered by the hormone, gibberellic acid (GA). In addition, alpha-amylase activity is increased in vitro by the reductive inactivation of its disulfide inhibitor protein by thioredoxin h (in the presence of NADPH and NTR). The present results with transformed barley seeds show that, like pullulanase, thioredoxin h expression alters alpha-amylase activity. In this case, the appearance of the enzyme during germination is accelerated and its abundance and activity are increased.

Figure 9:
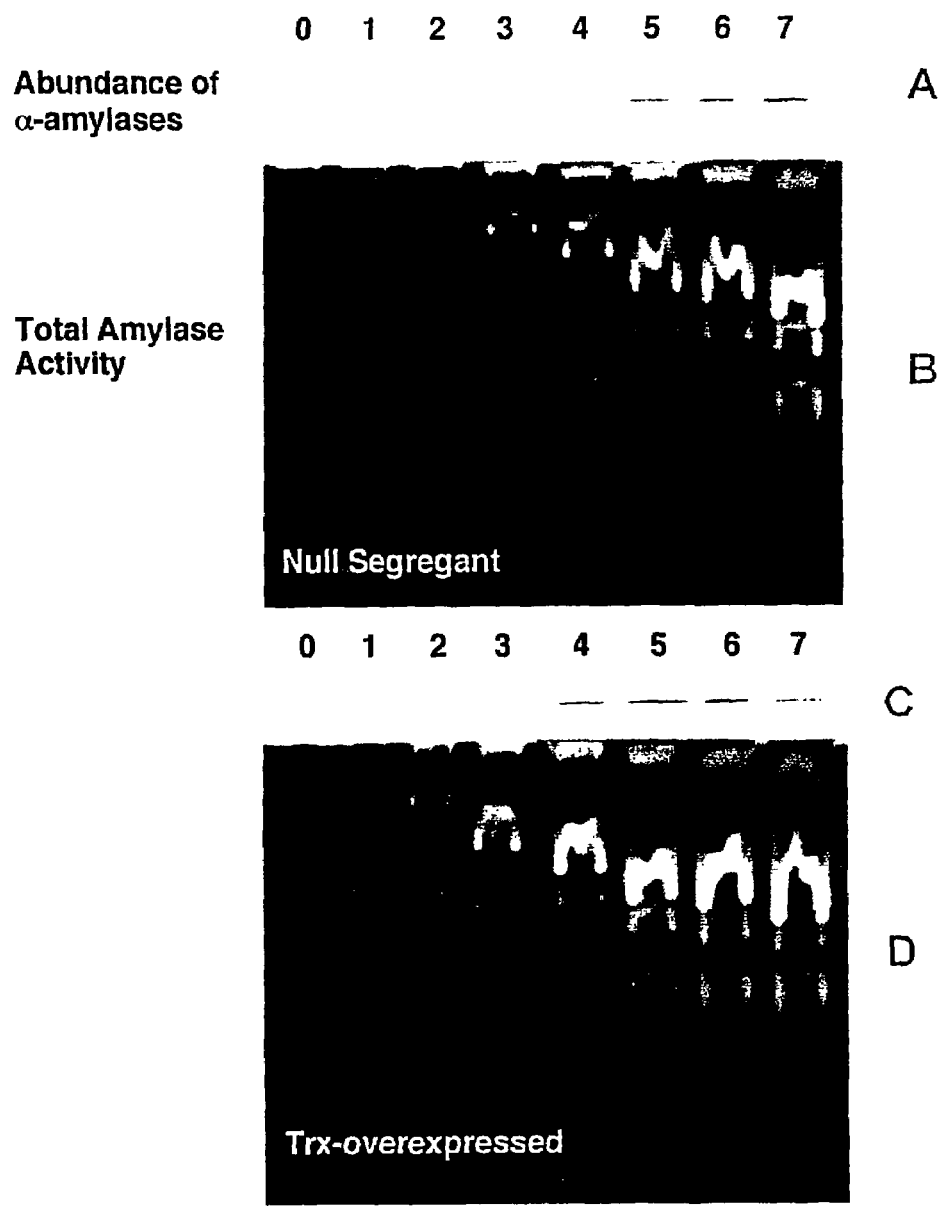
FIGS. 9A–D shows the change in the activity and abundance of amylases in transgenic and null segregant barley grains during germination and seedling development based on an activity gel. Panel A: abundance of alpha-amylases in null segregant based on western blot. Panel B: Total amylase activity in null segregant. Panel C: abundance of alpha-amylases in thioredoxin overexpressing grains. Panel D: total amylase activity in thioredoxin overexpressed grains.
Figure 10:
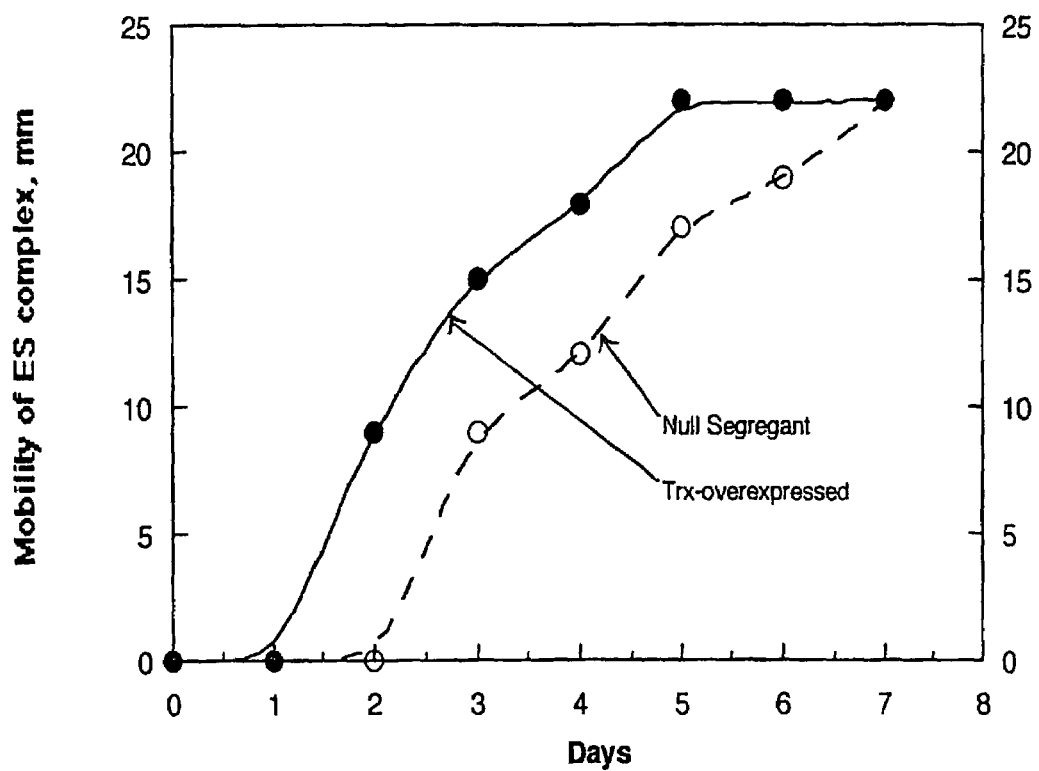
FIG. 10 shows the effect of overexpressed thioredoxin h on the activity of the major form of alpha-amylase during germination and seedling development. The size of the major alpha-amylase activity band in FIG. 9 was estimated by its rate of mobility during electrophoresis.
Figures 11A, 11B:
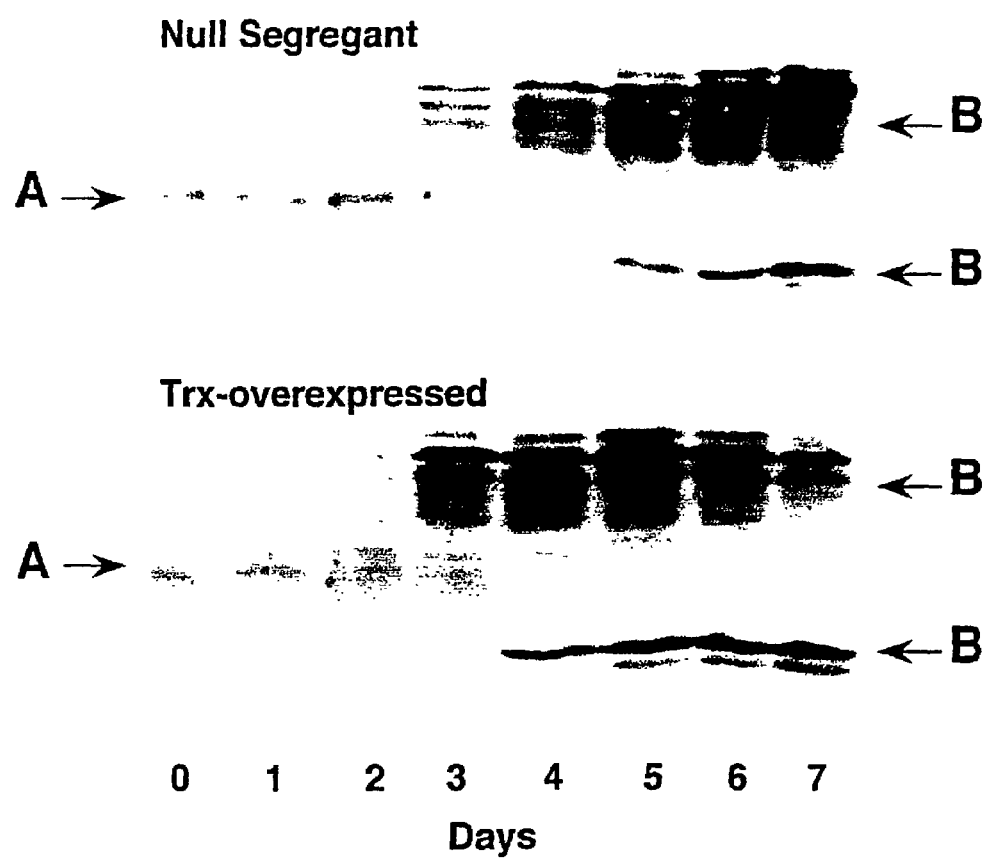
FIGS. 11A–B shows the effect of overexpressed thioredoxin h on the abundance of alpha-amylase A and B isozymes during germination and seedling development. The figure represents western blots of IEF gels developed for the null segregant and transgenic barley grains. Panel A: Null segregant. Panel B: Transgenic with thioredoxin overexpressed.

FIGS. 9A–D shows the early increase in both the abundance and activity of alpha-amylase (A+B forms) during germination and seedling development. Based on the antibody response in western blots, alpha-amylase was first detected 3 days after the onset of germination in the transgenic grain (FIG. 9C) whereas the enzyme did not appear until the fourth day in the null segregant (FIG. 9A). The onset of activity (based on the activity gel) followed a similar pattern (FIG. 9B and FIG. 9D). The mobility of the enzyme in the activity gel also reflected the early induction of activity in the transgenic grain (FIG. 10). That much of this increase in activity seen early on was due to the B (a GA-linked form) is supported by FIG. 11. Here, one can also see that the level of the minor A form of the enzyme (also GA-independent) was increased in grain overexpressing thioredoxin h. Again, the appearance of significant levels of the major (B form) alpha-amylase enzyme was advanced by 1 day.

Germination of Barley Grains Overexpressing Thioredoxin h

All operations were carried out at 25° C. (unless otherwise specified below) under conditions described by Kobrehel et al, 1992 and Lozano et al., 1996. Grains were surface sterilized by continuous stirring in 0.25% bleach for 30 min. Bleach was removed by extensive washing with sterilized distilled water. Thirty sterilized null segregant (GPdBhss-BarWtrx-29-11-10, in which the transgene was removed by crossing with a self-pollinated plant from the same line) and, thirty sterilized homozygous (GPdBhssBarWtrx-29-3) seeds were placed in each of a series of plastic Petri dishes (12.5 cm diameter) fitted with three layers of Whatman #1 filter paper moistened with 15 ml sterile distilled water. Plates were wrapped with aluminum foil and grain was germinated in a dark chamber at 20° C. for up to 7 days. One plate was read at each time point shown in FIG. 21. Percent germination, in the first day (from the start of incubation up to 24 hours), was determined by observing the emergence of the radicle. On the subsequent days, percent germination represents seedling growth as determined by measuring the length of coleoptile and roots of the germinated grains.

Figure 21:
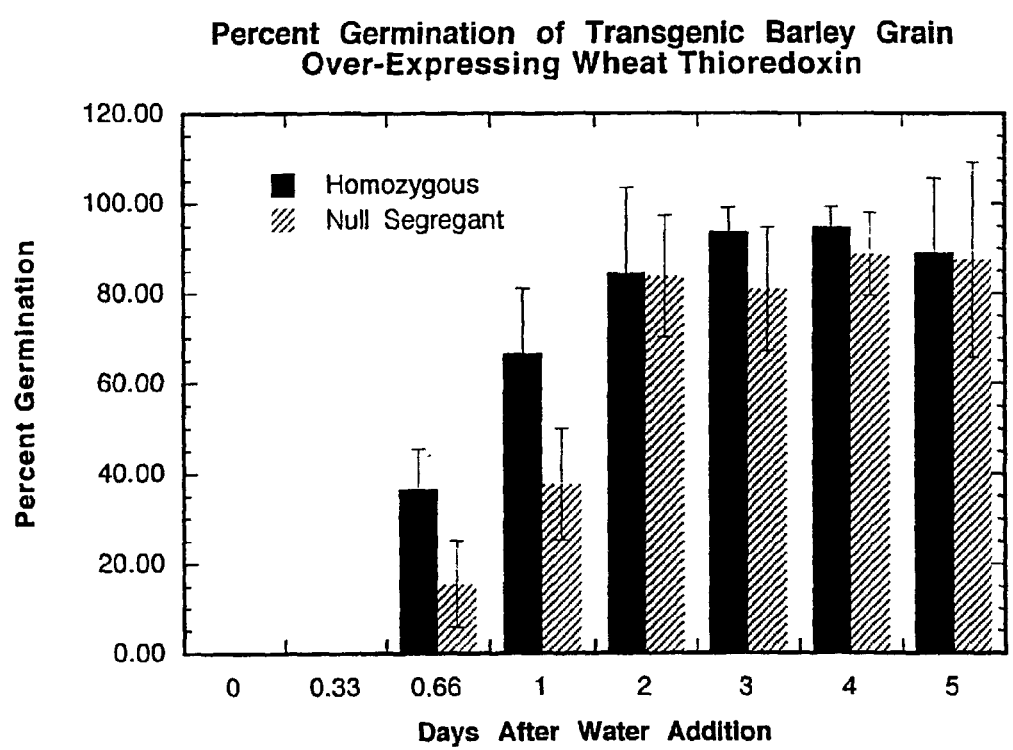
FIG. 21 shows the effect of overexpressed wheat thioredoxin h on the germination of null segregant and transgenic (homozygous) barley grains. Bars designate the standard deviation.

The results, shown in FIG. 21, indicate that 37% germination in transgenic barley overexpressing wheat thioredoxin h is detected about 16 hours after the onset of incubation. In contrast, only 16% germination in the null segregant was detected at 16 hours. Therefore, in the transgenic germination is advanced about 8 hours. However, on day 1 germination was detected in approximately 70% or about twice the number of transgenic grains in comparison to their null segregant counterparts. It is interesting to note that the onset of germination in the transgenics parallels the onset of the detection of alpha-amylase as shown in FIG. 10.

Sequential Extraction of Grain Proteins from Transgenic Barley Grains.

Isolated endosperm from 10 dry grains or seedlings (germinated as described above) were ground with mortar and pestle at 4° C. with 3 ml Tris-HCl buffer as indicated below. The separate mixtures of homozygous GPdBhssBar-Wtrx-29-3 and null segregant GPdBhssBarWtrx-29-11-10 grains were placed in a 5-ml screw-top centrifuge tube. Grains were mechanically shaken for 30 minutes and then centrifuged for 10 min at 24,000×g. The supernatant fraction (buffer-soluble) was decanted and saved for analysis and the residue was extracted sequentially with the following solvents for the indicated times: [1] 0.5 M NaCl (30 min); [2] water (30 min); [3] 2×50% propanol (2 hr); [4] 2×50% propanol+2% 2-mercaptoethanol (MET) (2 hr); and [5] 0.5 M borate buffer, pH 10, containing 1% SDS and 2% 2-mercaptoethanol (2 hr). Supernatant fractions of all extracts were determined for volume and protein content (by Coomassie dye binding method), then were stored at −20° C. until use. By convention, the fractions are designated: [1] albumin/globulin (buffer/salt/water); [2] hordein I (propanol); [3] hordein 11 (propanol+MET); and [4] glutelin (Borate/SDS/MET) (Shewry et al., 1980). These fractions were used to determine protein content, the distribution of proteins between the water soluble and insoluble fractions, the total extractable protein.

To determine the in vivo redox status of protein from transgenic barley grain during germination and seedling development, the extraction procedure was repeated except that 2 mM mBBr was included in the Tris grinding buffer and the grinding was under liquid nitrogen. The mBBr derivatized proteins were electrophoresed on SDS-polyacrylamide gels (1.5 mm thickness, 10–20% gels, pH 8.5 (Laemmli, 1970). Gels were developed for 16 hr at a constant current of 8 mA. Following electrophoresis, gels were placed in 12% (w/v) trichloroacetic acid and soaked for 4 to 6 hr with one change of solution to fix the proteins; gels were then transferred to a solution of 40% methanol/10% acetic acid for 8 to 10 hr with agitation to remove residual mBBr. The fluorescence of mBBr (both free and protein bound mBBr), was visualized by placing gels on a light box fitted with an ultraviolet light source (365 nm). Following removal of the excess (free) mBBr, images of gels were captured by Gel Doc 1000 (Bio-Rad).

To ascertain the equivalent protein amount of loaded extracts, SDS-gels were stained with Coomassie Brilliant Blue G-250 in 10% acetic acid for 30 min, and destained in 10% acetic acid for 30 min with the aid of a microwave oven. Protein stained gels were captured by Gel Doc 1000 as above.

The quantification of fluorescence (pixel×mm×mm) and protein (optical density×mm×mm) on gels were carried out by a software program for image analysis—Multi-Analyst, version 1.0 (Bio-Rad). Relative reduction was expressed as the ratio of fluorescence to protein.

The results of two experiments shown in Tables 5–7 demonstrate an increase in the total protein on a percent grain and a percent weight basis in the transgenic barley as compared to the null segregant. The transgenic have a thioredoxin content that is at least two-fold higher (10–15 µg/mg soluble protein; 2–8 ug/gram tissue) than the null segregant. The data indicate that this increase in total extractable protein is the result in redistribution of the protein to the most soluble albumin/globulin fraction. The redistribution of the protein to the soluble fraction increase in the transgenics is at least 5% higher than the controls.

TABLE 5

Protein Content of Various Fractions in Transgenic Barley Grain Overexpressing Wheat Thioredoxin h
Experiment I*

| Protein Fraction | Null Segregant | | Homozygous | |
|---|---|---|---|---|
| | mg/seed | mg/gram | mg/seed | mg/gram |
| Albumin/Globulin | 0.462 | 12.25 | 0.546 | 13.58 |
| Hordein I | 0.239 | 6.34 | 0.322 | 8.01 |
| Hordein II | 0.136 | 3.61 | 0.094 | 2.34 |
| Glutelin | 0.110 | 2.92 | 0.097 | 2.41 |
| Total Extractable Protein | 0.947 | 25.12 | 1.059 | 26.34 |

*Weight per 10 seeds is 0.377 g and 0.402 g for null segregant and homozygous line of transgenic barley.

TABLE 6

Protein Content of Various Fractions in Transgenic Barley Grain Overexpressing Wheat Thioredoxin h
Experiment II*

| Protein Fraction | Null Segregant | | Homozygous | |
|---|---|---|---|---|
| | mg/seed | mg/gram | mg/seed | mg/gram |
| Albumin/Globulin | 0.691 | 20.03 | 1.044 | 27.12 |
| Hordein I | 0.373 | 10.81 | 0.368 | 10.03 |
| Hordein II | 0.254 | 7.36 | 0.240 | 6.23 |
| Glutelin | 0.066 | 1.91 | 0.062 | 1.61 |
| Total Extractable Protein | 1.384 | 40.11 | 1.732 | 44.99 |

*Weight per 10 seeds is 0.345 and 0.385 for null segregant and homozygous line of transgenic barley

TABLE 7

Percent Increase of Extractable Protein in Homozygous Line

| | %/grain basis | %/mass basis |
|---|---|---|
| Experiment I | 12 | 4.9 |
| Experiment II | 25 | 12 |

Figure 22:
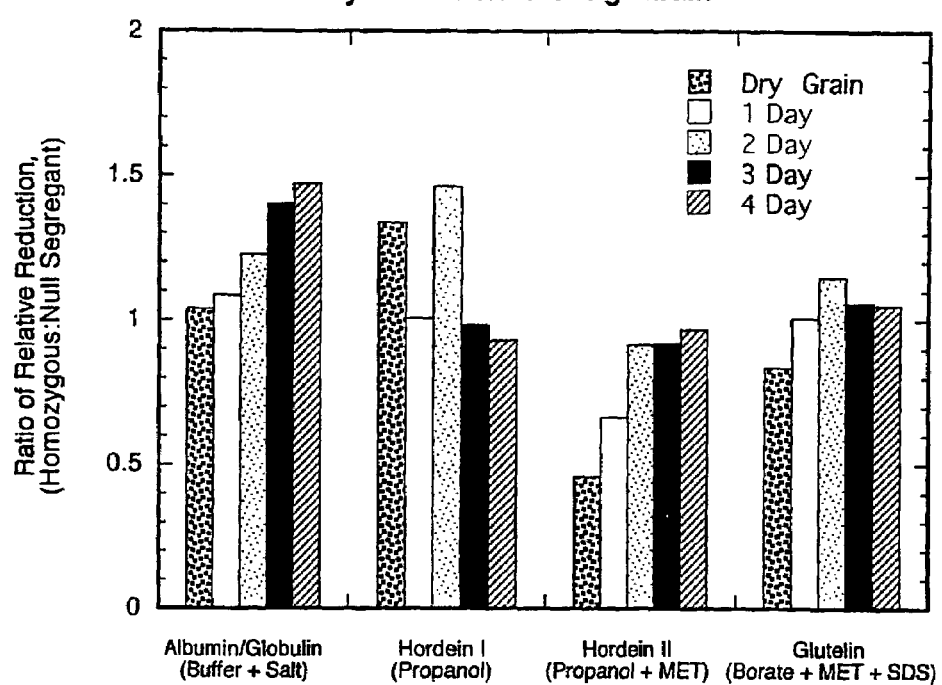
FIG. 22 shows the relative redox status of protein fractions in transgenic barley grain overexpressing wheat thioredoxin h in comparison to the null segregant in dry and germinated grain.

Analysis of the relative redox status (SH:SS) of protein fractions in transgenic and null segregant barley grains during germination and as dry grains are shown in FIG. 22. In dry transgenic grain, the greatest increase in reduction relative to the null segregant was observed in the hordein I fraction. This increase was paralleled by decreases in the relative redox status in the hordein II and glutelin fractions while the relative redox status of the albumin/globulin fraction was unchanged. The relative redox status of the transgenic in comparison to the null segregant is at least 5:1.

During germination, the albumin/globulin fraction progressively increases, reaching a relative redox ratio of about 1.5 on Day 4. The relative redox status of the hordein II and glutelin fractions also increased during germination but only reached parity with the null segregant. In contrast the relative redox status of the hordein I fraction was highly variable.

According to the above example, other types of plants, are transformed in a similar manner to produce transgenic plants overexpressing thioredoxin h, such as transgenic wheat, described below, rice, maize, oat, rye, sorghum (described below), millet, triticale, forage grass, turf grass, soybeans, lima beans, tomato, potato, soybean, cotton, tobacco etc. Further, it is understood that thioredoxins other than wheat thioredoxin h can be used in the context of the invention. Such examples include spinach h; chloroplast thioredoxin m and f, bacterial thioredoxins (e.g., *E. coli*) yeast, and animal and the like.

Example 2

Transgenic Wheat Grain Overexpressing Thioredoxin h and Arabidopsis NTR

Materials and Methods

Plant Materials

Spring cultivars of wheat, Bobwhite, Anza and Yecora Rojo, were grown in the greenhouse as described previously (Wan and Lemaux 1994; Lemaux et al. 1996). Ten- to 14-day-old germinating plants of a winter-wheat cultivar, Karl, were incubated at 4° C. for 45 to 60 days in the dark for vernalization treatment.

Wheat Expression Vectors

For wheat transformation, synthetic green fluorescent protein gene [sfgp(S65T)], wheat thioredoxin h (wtrxh) or Arabidopsis ntr expression vectors driven by barley endosperm-specific $B_1$- or D-hordein were constructed as follows:

(1) pDhSSsGFPN3-4: the chimeric DNA construct containing the D-hordein promoter-signal sequence-sgfp (S65T)-nos was obtained using a modified method of site-directed mutagenesis by PCR (Cho and Lemaux 1997). The three-primer strategy was used. A shorter fragment of 0.5-kb DHORSS was produced by PCR in the first reaction using primers, Dhor4 (5'-agaaagcttg-gtaccCTTCGAGTGCCCGCCGAT-3'; SEQ ID NO: 35) and DhorSSsGFP1 R (5'-GAACAGCTCCTCGC-CCTTGCTCAC AGCGGTGGTGAGAGCCACGAGGGC-3'; SEQ ID NO: 36), with the template pHor3-1 containing a genomic clone of D hordein (Sørensen et al., 1996), and this first PCR product (megaprimer) was diluted 50 times. DhorSSsGFP1 R is an overlapping primer which contain the sgfp(S65T) coding sequence and a partial signal peptide sequence (underlined) from the D-hordein promoter. For the second PCR reaction, five µl of the diluted megaprimer (DHORSS), twenty ng of template (pActl1sGFP-1; Cho et al., 2000) and 40 pmol of external primers [Dhor4 and NoslR (5'-cggaattc-GATCTAGTMCATAGATGACA-3': SEQ ID NO: 37)] were mixed to a final volume of 100 µl in 1× PCR buffer; pActl1sGFP-1 contains synthetic gfp gene [sgfp (S65T)] (Chiu et al, 1996) controlled by the rice actin1 promoter and its intron and terminated by nos. The resulting chimeric PCR product was digested with HindII and EcoRI and ligated into the HindII/EcoRI-digested pBluescript II KS(+) vector, further confirmed by DNA sequencing of the PCR-amplified fragment [D-hordein promoter with its signal peptide sequence plus the junction region with the 5' sgfp(S65T)], and used for stable transformation of wheat.

(2) pDhWTRXhN-2: Described previously.

(3) pdBhssWTRXhN3-8: Described previously.

Figure 12:
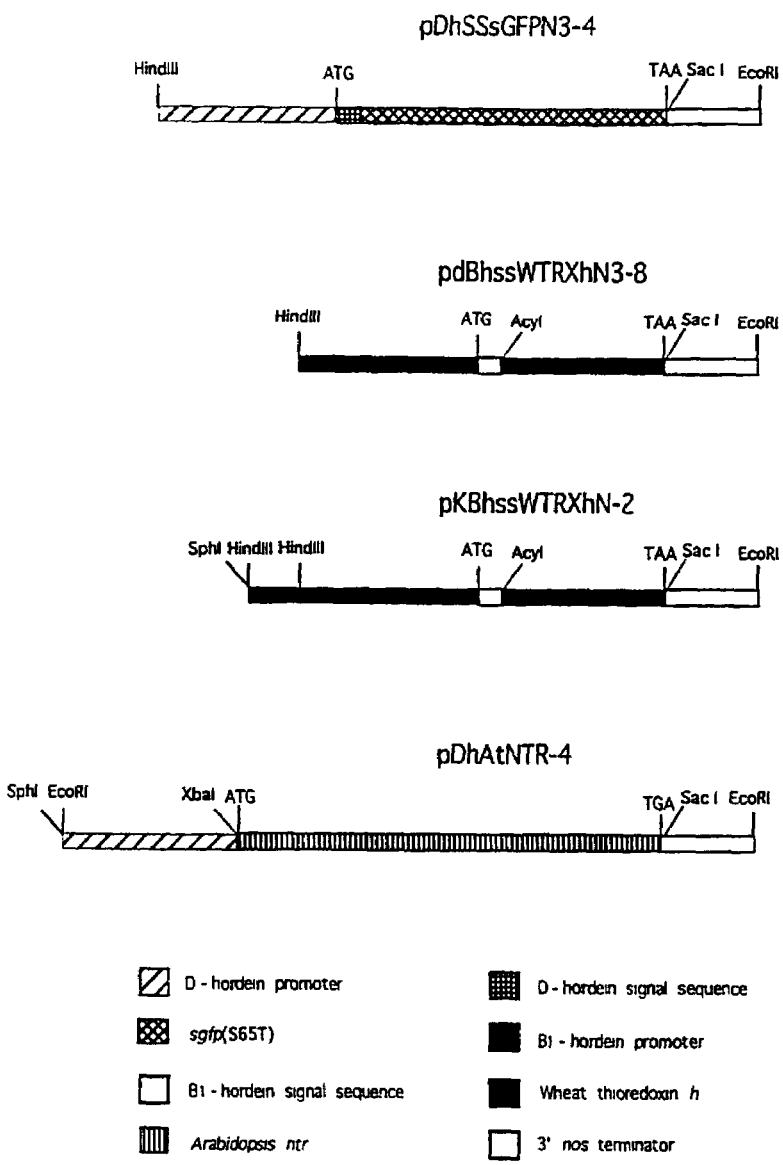
FIG. 12 depicts the DNA constructs used for wheat transformation.

(4) pKBhssWTRXN-2: pBhor-1 was digested with SphI and SacI in order to obtain the 0.55-kb 5'-flanking region of $B_1$-barley hordein promoter. The 0.55-kb SphI/SacI fragment was ligated into pSPORT 1 (GIBCO BRL, Gaithersburg, Md.) to make pSPBhor-4. pdBhssWTRN3-8 was digested with HindIII/EcoRI and the HindIII/EcoRI fragment containing the 0.43-kb barley endosperm-specific $B_1$-hordein promoter plus its signal peptide sequence, wrxh and nos was ligated into the HindIII/EcoRI-digested pSPBhor-4 to generate the pSPBhssVVrRXN-4 plasmid. In order to remove ampicillin resistance gene, the 1.3-kb SphI/EcoRI fragment of pSPBhssWTRXN-4 was ligated into SphI/EcoRI-digested pJKKmf(−) containing kanamycin resistance gene to form pKBhssWTRXN-2. Thus, the kanamycin'-backbone construct, pKBhssWTRXN-2, contains the 0.55-kb 5'-flanking region of the $B_1$-barley hordein promoter plus its signal peptide sequence, wrxh and mos (FIG. 12).

(5) pDhAtNTR-4: pDhAtNTR-4 was made by replacing the wtrxh gene in pDhWTRXN-2 (described above) with the PCR-amplified XbaI/SacI fragment containing Arabidopsis ntrcoding sequence from pAtNTR (a gift from Dr. S. Y. Lee). Primers, AtNTR1 (5'-ggtctaga ATGGAAACTCACAAAACC-3'; SEQ ID NO: 40) and AtNTR2R (5'-gggagctc TCAATCACTCTTACCCTC-3'; SEQ ID NO: 41), were used for amplification of the 1.009-Kb XbaI/SacI fragment containing 0.993-Kb Arabidopsis ntr coding sequence; small letters contain a restriction enzyme site for subcloning of the DNA construct containing Arabidopsis ntr gene and underlined letters indicate the Arabidopsis ntr sequences. The Arabidopsis ntr fragment was purified from a 0.7% agarose gel using QIAquick® gel extraction kit, digested with XbaI and SacI and ligated into XbaI/SacI-digested pDh-WTRXN-2 to generate the pDhAtNTR-4 plasmid. Nucleotide sequences of the PCR-amplified Arabidopsis ntr coding region were determined by DNA sequencing.

Stable Wheat Transformation

Stable transgenic lines of wheat transformed with pDh-SSsGFPN3-4, pdBhssWTRXhN3-8, pKBhssWTRXN-2 or pDhAtNTR4 were obtained using highly regenerative, green tissues as, transformation targets. Highly regenerative tissues have a high percentage of totipotent cells capable of sustained cell division and competent for regeneration over long period. In order to induce highly regenerative green tissues, whole immature embryos (IEs; 1.0–2.5 mm) were aseptically removed, placed scutellum side down on DBC3 medium (callus-induction medium containing 1.0 mg/L 2,4-dichlorophenoxyacetic acid, 0.5 mg/L BAP and 5.0 PM $CuSO_4$ Cho et al., 1998a–c). Five to 7 days after initiation, germinating shoots and roots were removed by manual excision. After 3 weeks of incubation at 24±1° C. under dim light conditions (approximately 10 to 30 µE, 16 Might), highest quality tissues from the scutellum were selected and maintained on DBC3 medium. Alternatively, highly regenerative, green tissues were obtained from daughter tissues, oval-shaped tissues with highly embryogenic structures which were emerged at the base of germinating shoots or from the outside layer of the tissues near the base of germinating shoots. Seven to 14 days after initiation, daughter tissues (2–4 mm in length) were isolated from germinating IEs by manual excision and transferred to fresh DBC3 medium. After an additional 3- to 4-week incubation, the tissues were selected again, broken into 2 to 4 pieces of about 3 to 5 mm in size and transferred onto fresh medium. The tissues were maintained on fresh medium, subculturing at 3- to 4-week intervals.

Only good quality tissues were selected for bombardment. The highly regenerative tissues (preferably about 3 to 4 mm in size) were transferred for osmotic pretreatment to DBC3 medium containing equimolar amounts of mannitol and sorbitol to give a final concentration of 0.4 M. Four hours after treatment with the osmoticum, the tissues were bombarded as previously described (Wan and Lemaux 1994; Lemaux et al. 1996). Gold particles (1.0 um) were coated with 25 µg of a 1:1 or 1:2 molar ratio of a mixture of pActl IHPT-4 (or pUbiINPTII-1) and and one of 4 plasmids, pDhSSsGFPN3-4, pdBhssWTRXhN3-8, pKBhss-WTRXN-2 or pDhAtNTR-4, followed by bombardment using a PDS-1000 He biolistic device (BioRad, Inc., Hercules, Calif.) at 600 or 900 psi. The plasmid pActIHPT-4 contains the hygromycin phosphotransferase (hpt) coding sequence under control of the rice actin1 promoter (ActI), its intron and the nos 3' terminator (Cho et al., 1998a–c). pUbiINPTII-1 contains the neomycin phosphotransferase (nptII) gene under control of the maize ubiquitin promoter and first intron and terminated by nos. Sixteen to 18 hr after bombardment, the bombarded tissues were placed to DBC3 medium without osmoticum and grown at 24±1° C. under dim light.

Following the initial 10- to 14-day culturing period, each regenerative tissue was broken into 1 to 3 pieces depending on tissue size and transferred to DBC3 medium supplemented with 20–25 mg/L hygromycin B (Boehringer Mannheim, Mannheim, Germany) for selection for hptor 30 mg/L G418 (Sigma, Saint Louis, Mo.) for nptII. Three weeks after the first round of selection, the cultures were transferred to fresh DBC3 medium containing 30 mg/L hygromycin B or 40 mg/L G418. From the third round selection, the tissues were subcultured and maintained on DBC3 medium containing 30 mg/L hygromycin B or 40 mg/L G418 at 3- to 4-week intervals. After the fourth or fifth round of selection, surviving tissues were transferred to DBC3 medium without selective agent. Following the identification of green tissues with sufficient regenerative structures on DBC3, the tissues were plated on solid regeneration medium without selective agent and exposed to higher intensity light (approximately 45–55 µE). After four weeks on regeneration medium (callus-induction medium without phytohormones), the regenerated shoots were transferred to Magenta boxes containing the same medium without selective agent. When the shoots reached the top of the box plantlets were transferred to the soil.

Polymerase Chain Reaction (PCR) and DNA Hybridization

Total genomic DNA from leaf tissues was purified as described (Dellaporta, 1993). To test for the presence of wtrxh in genomic DNA of putatively transformed lines, 500 ng of genomic DNA was amplified by PCR using either of two primer sets, WTRXh1 (5'-ATATCTAGAATGGCG-GCGTCGGCGGCA-3'; SEQ ID NO: 25) and WTRXh2R (5'-ATAGAGCTCTTACTGGGCCGCGTGTAG-3'; SEQ ID NO: 26) or WTRXh4 (5'-CCAAGAAGTTC-CCAGCTGC-3'; SEQ ID NO: 31) and WTRXh5R (5'-ATAGCTGCGACAACCCTGTCCTT-3'; SEQ ID NO: 32). The presence of hpt and nptII was tested by using each of the primer sets, HPT6F (5'-AAGCCTGAACTCACCGC-GACG-3'; SEQ ID NO: 42) plus HPT5R (5'-AAGACCAAT-GCGGAGCATATAC-3'; SEQ ID NO: 43) (Cho et al., 1998a-c) and NPT1 F (5'-CAAGATGGATTGCACGCAG-GTTCT-3; SEQ ID NO: 44) plus NPT2R (5'-ATAGAAG-GCGATGCGCTGCGAAT-3'; SEQ ID NO: 45). Amplifications were performed with Taq DNA polymerase (Promega, Madison, Wis.) in a 25-µl reaction (Cho et al., 1998a–c). Twenty-five µl of the PCR product with loading dye was electrophoresed on a 1.0% agarose gel with ethidium bromide and photographed using exposure to UV light. Presence of 0.4- and 0.14 kb fragments was consistent with an intact and truncated wtrxh fragments, respectively; 0.81-kb hpt and 0.76-kb nptII fragments for the pActl IHPT-4 and pUbiINPTII-1 plasmids, were produced with hpt and nptII primers, respectively. Homozygous lines for wtrxh were screened using $T_1$, $T_2$ or $T_3$ plants by PCR analysis.

GFP Expression Detection by Fluorescence Microscopes

GPF expression was monitored at higher magnification using a Nikon Microphot-5A fluorescent microscope equipped with a Nikon B-2A filter block containing a 450–490 excitation filter and a BAS20 emission barrier filter (Cho et al., 2000).

Western Blot Analysis

Western blot analysis was performed on seeds from selected transgenic wheat lines as well as from control counterparts grown under the same conditions. Thioredoxin h purified from seeds of a bread wheat cultivar, cv. Capitole, was used as a reference. Whole seeds were ground to a fine powder with a mortar and pestle under liquid nitrogen. Ten seeds were used for each sample; the volume of extraction buffer [50 mM Tris HCl or phosphate buffer, pH 7.8, 0.5 mM PMSF, 1 mM EDTA] varied from 2 to 4 ml depending on the number of seeds used and the viscosity of the extract. Grinding was continued for an additional min after buffer addition, the preparation was centrifuged at 14,000×g for 10 min and the supernatant solution was saved as the soluble (albumin-globulin) fraction. SDS-PAGE of the soluble fraction was performed in 12–17% polyacrylamide gradient gels at pH 8.5 (Laemmli, 1970). Equal amounts of protein (40 µg) of each sample quantitated according to Bradford (1976) were diluted 1:2 v/v in Laemmli sample buffer, boiled for 3 minutes, loaded onto gels and subjected to electrophoresis at a constant current of 15 mA. Proteins were transferred to nitrocellulose at a constant voltage of 40 V for 4 hours at 4° C. using a Hoefer Transphor Transfer Unit (Alameda, Calif.) (all at 25° C.). Nitrocellulose was blocked with 5% powdered milk in TBS for 2 hours, incubated in primary antibody for 4 hours and in secondary antibody for 1 hour. The primary antibody was wheat anti-thioredoxin h II (Johnson et al., 1987b) diluted 1 to 500; secondary antibody was goat anti-rabbit alkaline phosphatase (Bio-Rad, Hercules, Calif.) diluted 1:3000. Blots were developed in NBT/BCIP alkaline phosphatase color reagent (Bio-Rad, Hercules, Calif.). Images were scanned using a Bio-Rad GelDoc 1000 (Hercules, Calif.) and analyzed using Bio-Rad Multi Analyst, version 1.0.2.

Results and Discussion

Construction of Expression Vectors

To overexpress sGFP(S65T), WTRXh and AtNTR in wheat seed, five expression constructs containing wtrxh driven by endosperm-specific hordein promoters, pDhSSs-GFPN3-4, pDhWTRXN-2, pdBhssWTRXhN3-8, pKBhss-WTRXN-2 or pDhAtNTR-4, were made. Out of five constructs, four (pDhSSsGFPN3-4, pdBhssWrRXhN3-8, pKBhssWTRXN-2 or pDhAtNTR-4; FIG. 12) were used for stable transformation of wheat.

Production of Transgenic Plants

Highly regenerative tissues (at least 1 tissue, preferably 50, and most preferably 500 of 3–4 mm in length) were bombarded and cultured on DBC3 medium for the first 10 to 14 days in the absence of selection. For the second transfer (1st round selection), selection was on DBC3 medium supplemented with 25–30 mg/L hygromycin B for hpt selection or 30 mg/L G418 for nptII selection. At the second round selection, DBC3 medium with 30 mg/L hygromycin B or 40 mg/L G418 was used. From the 4th transfer (3rd round selection) onward, the selection pressure was maintained at the same level. In general, hygromycin- or G418- resistant tissues with some green sectors were observed at the third round selection. Putative transgenic calli with green sectors were maintained and proliferated on the same medium without selective agent from after the fourth or fifth round of selection, until the green sectors formed fully developed regenerative structures. Green regenerative tissues were regenerated on regeneration medium and the plantlets transferred to soil approximately 3 to 4 weeks after growth on the same medium of the Magenta boxes. To date using this transformation protocol, we obtained two independent Bobwhite lines, four transgenic Anza lines, two transgenic Yecora Rojo lines transformed with pdBhss-WTRXhN3-8, one Bobwhite line transformed with pKBh-ssWTRXN-2 and one Yecora Rojo line transformed with pDhAtNTR-4 (Table 8). We also obtained two independent Bobwhite lines transformed with pDhSSsGFPN3-4 (data not shown).

Endosperm-Specific Expression of Barley Hordein Promoter in Transgenic Wheat

Figure 13:
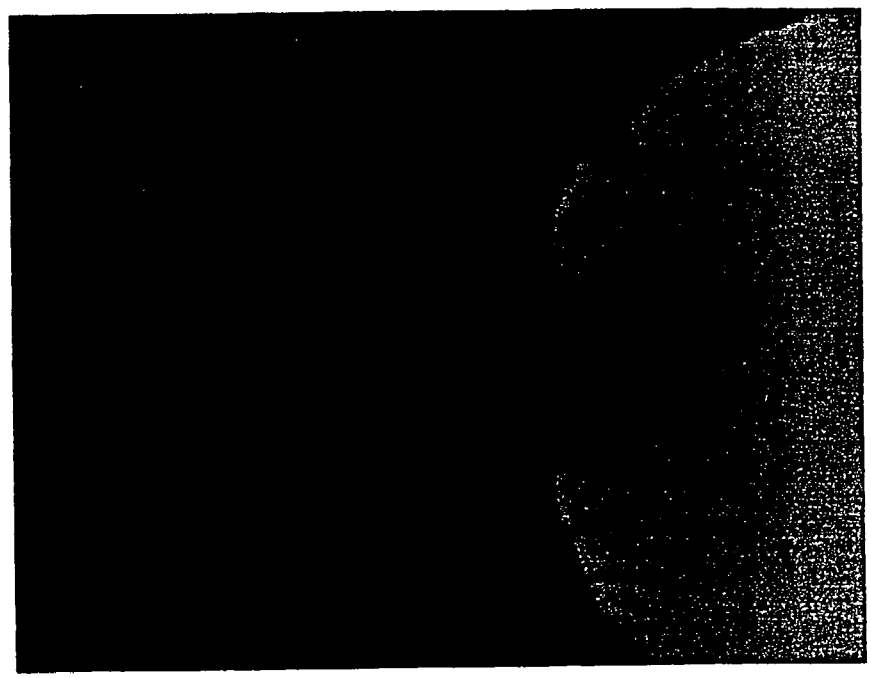
FIG. 13 shows the endosperm-specific expression of barley D-hordein promoter sgfp(S6fT) in transgenic wheat plants. Transgenic endosperm is at the right, transgenic embryo is at the left.

Expression of GFP driven by barley D-hordein promoter was found specifically in the endosperm tissue of developing wheat grains; GFP expression was not clearly observed in immature embryo tissues (FIG. 13).

Analysis of $T_o$ Plants and Their Progeny

Figure 14:
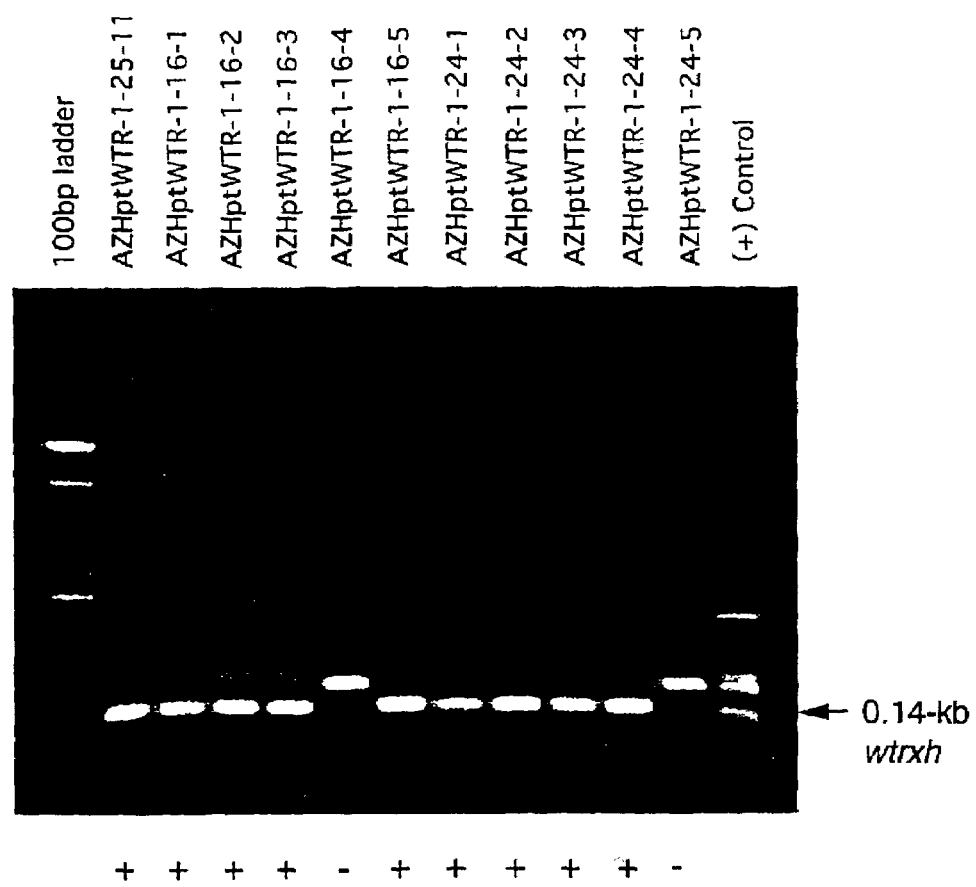
FIG. 14 shows the PCR analysis of genomic DNA from transgenic wheat plants.

PCR analysis was performed using two sets of WTRXh primers and one set of AtNTR primers. PCR zmplification resulted in 0.4-kb intact wtrxh or 0.14-kb truncated wtrxh (FIG. 14) and 0.5-kb internal Atntr fragments from transgenic lines. Seeds of $T_1$ and their progeny from some wtrxh-positive lines were planted in order to screen homozygous lines. Homozygous lines and null segregants were obtained from AZHptWTR-1, AZHptWTR-21 and YRHptWTR-1 (Table 8). Other lines are currently being screened for homozygous lines.

Characterization of Wheat Thioredoxin h Produced in Transgenic Grain

Figure 15:
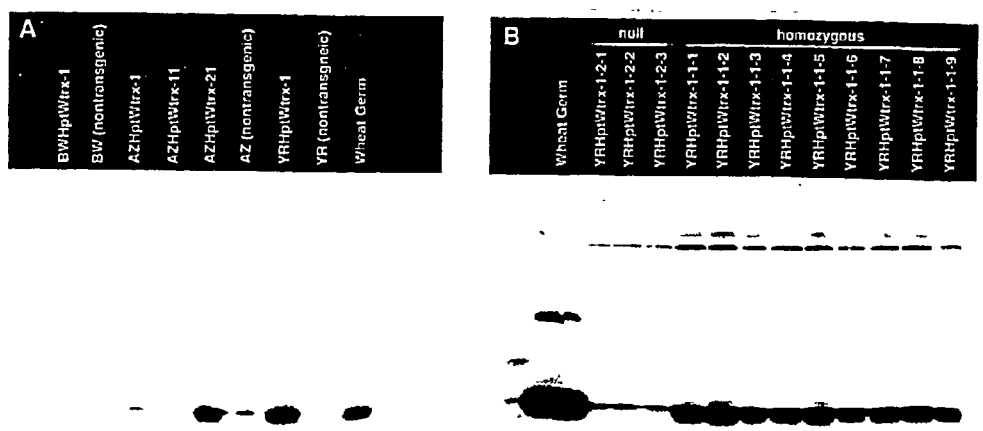
FIGS. 15A–B shows wheat thioredoxin h-overexpressing wheat lines screened by western blot analysis. Panel A: $T_0$ wheat lines. Panel B $T_3$ homozygous line.

Of the stably transformed lines that expressed wheat thioredoxin h, on average, its level was found to be higher in transformants. Western blot analysis of soluble protein fractions from heterozygous mixtures of seeds from three of these lines, AZHptWTR-1, AZHptWTR-21 and YRHptWTR-1, showed approximately 5 times, 20 times, and 30 times more thioredoxin h, respectively, than nontransformed control grain (FIG. 15A). The thioredoxin content of the null segregant (YRHptWTR-1-2-1 to -3) was similar to that of the corresponding, nontransformed control (FIGS. 15A and B).

60 ml of each extraction solution indicated below was added. The mixture was shaken mechanically and then centrifuged for 30 min at 5,000×g. The supernatant fraction was decanted and saved for analysis, and the residue was mixed with the next solution. The powdered grain was extracted sequentially with the following solvents for the indicated times: [1] 2×0.5 M NaCl (30 min); [2] 2×70% ethanol (2 hr); [3] 2×0.1 M acetic acid (2 hr). Supernatant fractions of all extracts were analyzed for protein by the Coomassie dye binding method (Bradford, 1976) and then were stored at −20° C. until use. By convention, the fractions are designated: [11 albumin/globulin (water/salt-water); [2] gliadin (ethanol); and [3] glutenin (acetic acid) (Kruger et al., 1988; Shewry et al., 1986). These fractions were used for digestion and skin tests in Example 5, below.

Digestion of Glutenins

For reduction of glutenins extracted as above from non-transgenic green house plants, 4.2 µg NTR, 2.4 µg thioredoxin (both from *E. coli*), and 1 mM NADPH were added to 240 µg of target protein and incubated in a 37° C. water bath for 45 minutes. NTS (NTR/thioredoxin/NADPH) treated and untreated glutenins were incubated in 100 µl of simulated intestinal fluid (SIF) (Board of Trustees (ed.), 1995, Simulated Gastric Fluid, TS., pp 2053, The United States Pharmacopeia, 23, The National Formulary 18, United States Pharmacopeial Convention, Inc., Rockville, Md.) as described below. SIF contained 5 µg trypsin (or 20 µg pancreatin), 48.9 mM monobasic potassium phosphate, and 38 mM sodium hydroxide. After addition of the enzymes the pH was brought to 7.5 with 0.2 M sodium hydroxide.

TABLE 8

Summary of Transformation Experiments for Three Wheat Cultivars: Bobwhite, Anza and Yecora Rojo

| Cultivars/Plasmids or bombardment | Transgenic wheat lines | DNA PCR ($T_0$ leaf) hpt | DNA PCR ($T_0$ leaf) wtrx | DNA PCR ($T_0$ leaf) ntr | WTRXh or NTR expression in $T_1$ seeds | Comments |
|---|---|---|---|---|---|---|
| BW/pAct1IHPT-4 + pdBhssWTRXhN3-8 | BWHptWTR-1 | + | + | | n.d. | |
| | BWHptWTR-3 | + | − | | n.d. | |
| | BWHptWTR-4 | + | + | | n.d. | |
| | BWHptWTR-5 | + | − | | n.d. | |
| AZ/pACT1IHPT-4 + pdBhssWTRXhN3-8 | AZHptWTR-1 | + | + | | + | homozygous |
| | AZHptWTR-11 | + | + | | + | |
| | AZHptWTR-13 | + | + | | n.d. | |
| | AZHptWTR-21 | + | + | | + | homozygous |
| YR/pACT1IHPT-4 + pdBhssWTRXhN3-8 | YRHptWTR-1 | + | + | | + | homozygous |
| | YRHptWTR-2 | + | − | | n.d. | |
| | YRHptWTR-8 | + | + | | n.d. | |
| BW/pUbilNPTII-1 + pKBhssWTRN-2 | BWHptBhWTR-10 | + | + | | n.d. | |
| YR/pAct1IHpt-4 + pDHAtNTR-4 | YRHptAtNTR-1 | + | | + | n.d. | |

BW, AZ and YR represent Bobwhite, Anza, Yocora Rojo, respectively
n.d.: not determined Effect of Thioredoxin Reduction on Digestion of Wheat Glutenins by Trypsin and Pancreatin Sequential Extraction of Grain Proteins from Transgenic Wheat Grains Transgenic grain (YRHptWTR-1-1) and null segregant (YRHptWTR-1-2) grain were ground with a coffee grinder at room temperature. Ground powder from 10 grams of each line was placed in a 250-ml screw-top centrifuge bottle and Digests were incubated in a 37° C. water bath for 0, 20, 60, or 80 minutes. To stop the reaction, 100 mM PMSF and leupeptin (1 µg/ml) was added for trypsin digests and 1 N HCl for pancreatin digests. SDS-PAGE analysis of the digested samples was performed in 8–16% gradient gels as described by Laemmli (1970). Gels of 1.5 mm thickness were developed for 16 hr at a constant current of 7 mA. SIDS gels were stained with Coomassie brilliant blue R-250 in 10% acetic acid for 30 min, and destained in 10% acetic acid for 30 min with the aid of a microwave oven. Protein stained gels were captured by Gel Doc 1000. The quantification of protein (optical density×mm×mm) on the gels was carried out with a software program for image analysis- Multi-Analyst, version 1.0 (Bio-Rad). Relative digestion was expressed as the percentage of zero time undigested protein.

Figure 16:
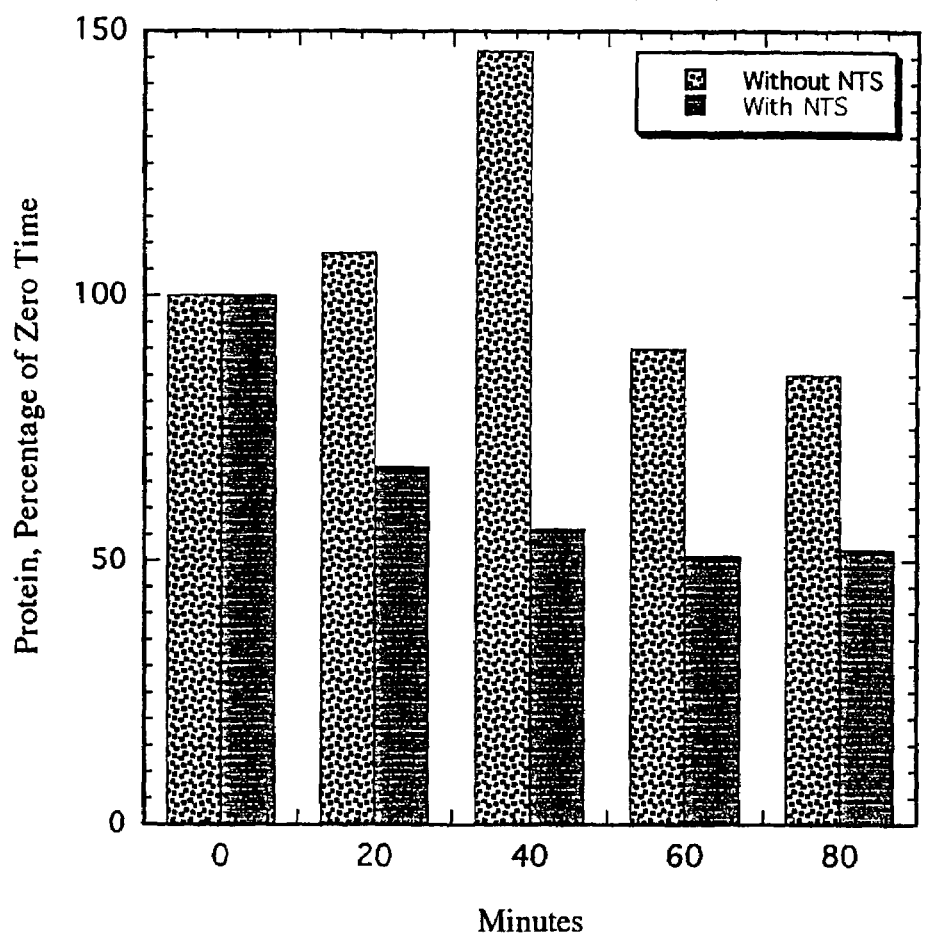
FIG. 16 shows the effect of thioredoxin reduction on digestion of wheat glutenins by trypsin.
Figure 17:
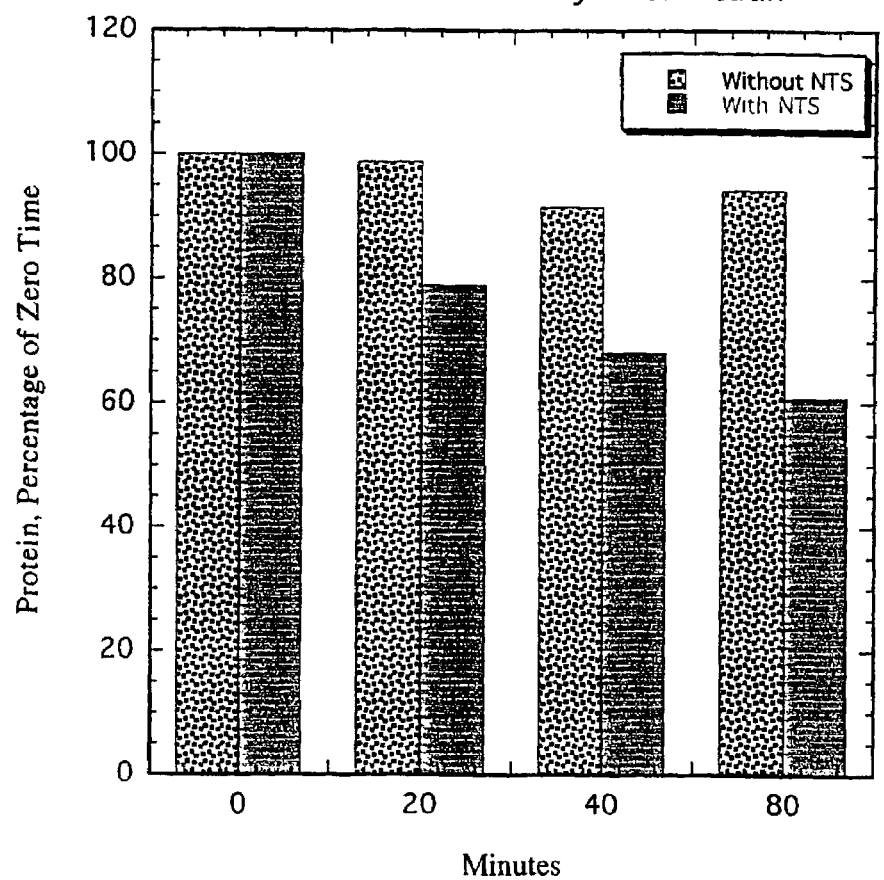
FIG. 17 shows the effect of thioredoxin reduction on digestion of wheat glutenins by pancreatin.

The results shown in FIGS. 16 and 17 demonstrate that thioredoxin reduction results in enhanced susceptibility of glutenins to protease digestion by trypsin and pancreatin, respectively. The most pronounced effects were observed with trypsin where about 55% of protein remained at 60 minutes post-digestion in the NTS treated sample in comparison to about 90–95% of the starting protein remained in the non-NTS treated sample. In the trypsin digestions, proteolysis progressed for 60 minutes and apparently plateaued. In the pancreatin digests, proteolysis progressed less rapidly. At 80 minutes post-pancreatin treatment, about 60% of the starting proteins remained in the NTS treated sample in comparison to 95% protein remaining in the non-NTS sample. Thus the transgenic grains of the present invention are more susceptible to digestion and are hyperdigestible. The increase in the digestibility is at least 5% in the transgenic plants in comparison to the non-transgenic grains.

Example 3

Effect of NTR on the Reduction of Proteins in Extracts of Wheat Grains Overexpressing Thioredoxin h In vitro Reduction of Proteins by NADPH or NTR or NADPH & NTR Aliquots of the albumin/globulin fraction from the homozygous lines overexpressing thioredoxin h as described in Example 2 and null segregant lines were used. The reaction was carried out in 30 mM Tris-HCl buffer, pH 7.9. As indicated the treatments were: (i) control, (ii) 1.25 mM NADPH, (iii) 3.0 lag $Arabidopsis$ NTR, (iv) NADPH & NTR combined, and (v) 5 mM dithiothreitol (DTT). The above reagents were added to 70 microliters of this buffer containing 60 µg of protein. Total reduction by dithiothreitol (DTT) was achieved by boiling for 5 min. After incubation for 60 min at 37° C., 100 nmoles of mBBr were added and the reaction was continued for another 15 min at room temperature. To stop the reaction and derivatize, excess mBBr, 10, µl of 100 mM MET was added. The reduced samples, after adding 25 µl of 4× Laemmli sample buffer, were analyzed as described by mBBr/SDS-PAGE (Kobrehel, K. et al. 1992).

Figure 18:
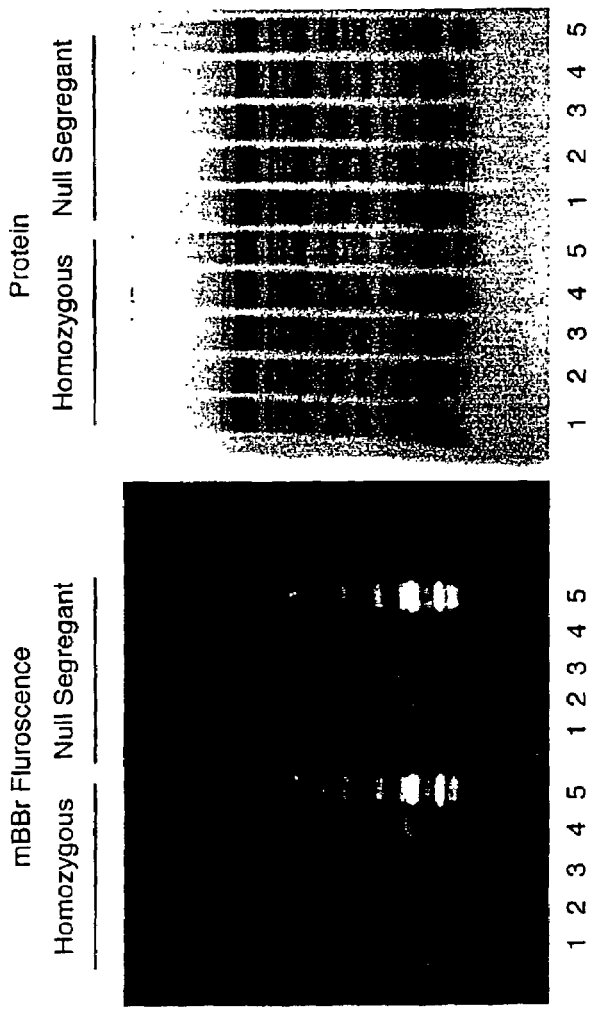
FIG. 18 show the effect of NTR on the reduction of proteins in extracts of transgenic wheat overexpressing thioredoxin h verses a null segregant.

The results shown in FIG. 18 indicate that the albumin/globulin proteins in the homozygous transgenics overexpressing thioredoxin h are more efficiently reduced than the albumin/globulin fraction of grain from their null segregant counterparts.

Example 4

Effect of Overexpressed Thioredoxin h on Allergenicity of Proteins from Wheat Grain The following protocol was approved by the appropriate committees at both the University of California-Davis (Animal Use and Care Administrative Advisory Committee, effective Jan. 21, 1999–Jan. 21, 2000) and the University of California-Berkeley (Animal Care and Use Committee, effective May 11, 1999–Apr. 30, 2000). The animals representing the sixth or seventh generation of the colony were housed in AAAALAC-accredited facilities and were cared for according to Institute of Animal Resources guidelines.

Dogs from the UC-Davis sensitized Dog Colony (Ermel et al., 1997) that were sensitized to commercial whole wheat grain extract (Bayer), were selected as strong reactors from two groups: 1) 2 year-old, designated "young dogs," and 2) 7 year-old, "old dogs." Before starting the skin tests, each animal received an intravenous injection of 5 ml sterile saline solution containing 0.5% Evans Blue (0.2 ml/kg). After 5 min, skin tests were performed by 100 µl intradermal injections of log dilutions of each wheat protein fraction in PBS buffer on the ventral abdominal skin. The quantity of protein injected ranged from 33 pg to 10 µg. The fractions tested were: 1) salt water-soluble (albumins and globulins); 2) ethanol-soluble (gliadins); acetic acid-soluble (glutenins). After 20 min, length and width of wheal areas were measured by a blinded reader. The total area was calculated as an ellipse (n/4×L×W). Protein allergenicity of the null segregant (control) and the homozygous wheat lines was obtained by comparison of the total wheal area generated by the different dilutions of each extract.

Figure 19:
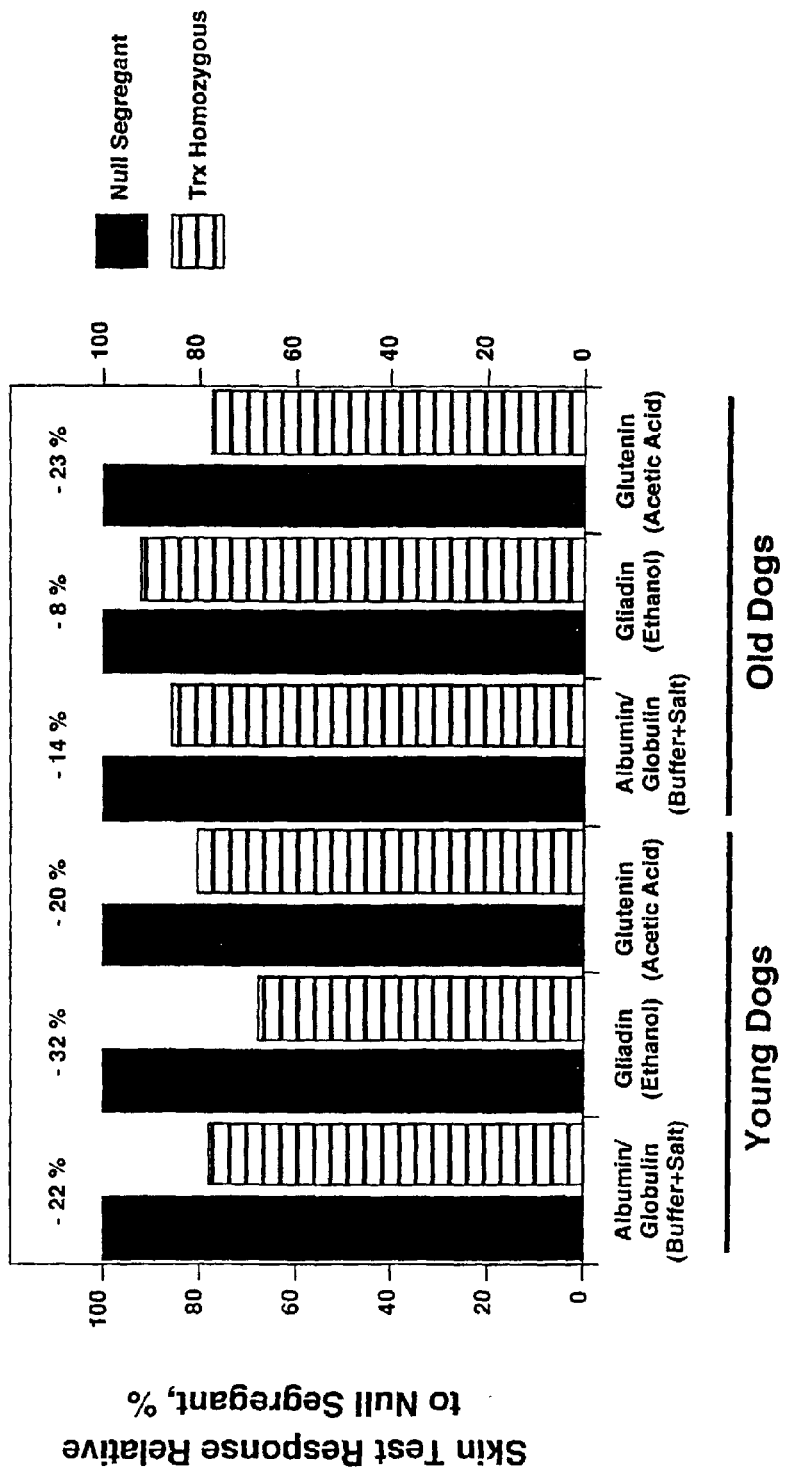
FIG. 19 shows the effect of overexpressed thioredoxin h on allergenicity of proteins from wheat grain.

The responses of the animals are shown in FIG. 19 and indicate that the proteins obtained from the transgenic wheat are less allergenic that the protein obtained from the null segregant. For each fraction tested, both young and old animals were less responsive to proteins from transgenic wheat. The allergenicity with the transgenics were decreased at least 5% in comparison to nontransgenic controls. The allergencity in the young dogs was more substantially reduced, ranging from 20 to 32% decrease. In contrast, the allergenicity in older animals was reduced by 8 to 23%.

To demonstrate the hypoallergenicity of malt produced from the transgenic wheat grain, malt is produced according to standard protocols known in the art from the transgenic seeds. Extracts of the malt are produced according to the above procedure. Young and old sensitized dogs, as described above, are injected intravenously with about 5 ml sterile saline solution containing 0.5% Evans Blue (0.2 ml/kg). After about 5 min, skin tests are performed by 100 µl intradermal injections of log dilutions of each malt protein fraction in PBS buffer on the ventral abdominal skin. The quantity of protein injected is about 33 pg to 10 µg. The fractions are as described above. After about 20 min, the length and width of the wheal areas are measured by a blinded reader and the total area is calculated as an ellipse. Malt protein allergenicity of malt produced from a null segregant (control) and malt from homozygous wheat lines are obtained by comparison of the total wheal area as described above. The allergenicity in the young dogs is more substantially reduced, and range from about 20–30% decrease. The older animals allergenicity is reduced by about 5–20%.

Accordingly, a food product such as beer produced from the hypoallergenic malt also is hypoallergenic.

Example 5

Transgenic Sorghum Expressing Barley Thioredoxin h Seed Digestibility

Seeds from ten major cultivars of $Sorghum\ bicolor$ are screened for a thioredoxin-dependent increase in digestibility of constituent proteins using simulated gastric (pepsin), and intestinal (pancreatin) fluids. The cultivars are representative of those grown in the United States, Australia and different parts of Africa.

Albumin, globulin, kafirin, and glutelin protein fractions are isolated according to their differential solubilities. Seed, 3 g, is ground in a coffee grinder, extracted sequentially with 30 ml of: [1] 0.5 M NaCl, [2] 60% (v/v) 2-propanol, and [3] 0.1 M sodium borate buffer, pH 10, on a shaker at 25° C. for 30 min, 4 hours, and 4 hours, respectively. The extracted fractions correspond, respectively, to [1] albumin plus globulin [2] kafirin, and [3] glutelin. Total kafirins or cross-linked kafirins are extracted with 60% 2 propanol plus 1% 2-mercaptoethanol (Shull et al., 1992). Each suspension is clarified by centrifugation at 10,000×g for 20 min at 4° C.; three successive extractions are performed with the salt solution followed by two water washes. The remaining extractions are repeated twice. Resulting supernatant solutions are pooled and the digestibility of each fraction is tested on the same day as isolation.

Aliquots of individual sorghum protein fractions are reduced either with the NADP/thioredoxin or the NADP/glutathione system prior to digestion and the results compared with untreated control preparations. Alternatively, total protein extracted with sodium myristate, a nonreducing detergent that solubilize wheat gliadins and glutenins in a biochemically active form (Kobrehel and Buchuk, 1978) can be tested for digestibility. Reduction of the disulfide bonds of proteins is performed using mBBr/SDS-PAGE as previously described (del Val et al, 1999) in a volume of 100 µl with either: (i) the NADPlthioredoxin system, consisting of 5 µl of 25 mM NADPH, 8 µl of 0.3 mg/ml *E coli* thioredoxin and 7 ul of 0.3 mg/ml *E. coli* NTR; or (ii) the NADPlglutathione system composed 5 µl of 25 mM NADPH, 10 µl of 30 mM glutathione and 15 µl of 0.1 mg/ml glutathione reductase. Reactions are carried out in a 30 mM physiological buffered saline (PBS) solution containing 50 µg of each protein. The reaction mixtures are incubated at 4° C. overnight or at 37° C. and 55° C. for 15 min (Kobrehel et al., 1992; del Val et al., 1999). The temperature found to work best is used for subsequent experiments. For complete reduction, samples are incubated in PBS with 5 µl 100 mM DTT and boiled 5 min. Protein fractions (albumin-globulin, kafirin, glutelin: 240 µg protein) is subjected to simulated digestion, either untreated or reduced with NADP/thioredoxin or NADP/glutathione, by pepsin (gastric simulation) or trypsin/chymotrypsin/carboxypeptidase (pancreatin: intestinal simulation).

Pepsin Assay

Each fraction, 500 µg of protein, is added to 100 µl of simulated gastric fluid [0.32% pepsin (w/v) and 30 mM NaCl adjusted to pH 1.2 with HCl] (Astwood et al., 1996). The reaction mixture is incubated for up to 60 min at 37° C. and stopped with 0.375-fold volume of 160 mM $Na_2CO_3$ to give neutral pH. The protein mixture is subjected to SDS-PAGE and stained for protein with Coomassie blue as described below.

Pancreatin Assay

Each fraction, 500 µg protein, is added to 100 µl of simulated intestinal fluid (1% porcine pancreatin (w/v), 48.9 mM monobasic potassium phosphate and 38 mM NaOH adjusted to pH 7.5 with NaOH) (see United States Pharmacopeai, 1995). The reaction mixture is incubated for up to 60 min at 37° C. and stopped with 1/10 volume of 100 mM PMSF plus 1 pg/ml leupeptin. The protein mixture is subjected to SDS-PAGE and stained with Coomassie blue as described below.

Two widely grown cultivar showing the most improved susceptibility to proteolytic and starch digestion after reduction by the thioredoxin system are used for the transformation work.

Isolation and Digestibility of Starch

Starch Granule Isolation

Starch granules from dry mature sorghum grain are extracted as described (Sun and Henson 1990). Sorghum grain is washed with distilled water and steeped for 48 h in 20 mM Na-acetate buffer, pH 6.5, containing 0.02% NaAzide. Softened kernels are ground first with a mortar and pestle and then with a VirTis homogenizer for 6 min at 80% full speed and the grist passed through two sieves (250 and 75 um). Crude starch that passes through both sieves is purified by centrifugation (60×g for 2.5 min) through a layer of 65% (w/v) sucrose. Pelleted starch granules are recentrifuged one or two times under the same conditions and resuspended in 20 mM sodium acetate buffer, pH 6.5 containing 0.02% sodium azide.

Starch Digestion

Starch digestibility is measured based on enzymatic hydrolysis using porcine pancreatic alpha-amylase (Type VI-B, Sigma Chemical Co., St. Louis, Mo.). Incubation mixtures containing 2% (w/v) starch, 0.5% (w/v) BSA, 0.02% (w/v) azide, 25 mM NaCl, 5 mM $CaCl_2$ and 10 units of alpha-amylase in 10 mM sodium phosphate buffer, pH 6.9, are incubated 37° C. Aliquots (50 to 100 µl) of reaction mixture is periodically removed for determination of glucose and total reducing sugars released from starch granules. Reducing sugar concentration is measured by the dinitrosalicylic acid method (Bernfeld, 1955) and total starch content by the enzymatic procedure of McClear et al (1994).

Reduction of Protein on Starch Granules

Aliquots of the isolated 2% (w/v) starch are incubated with the NTS system to reduce the proteins on the surface of the granule as described above (Examples 3 and 4). Following reduction, the starch granules are tested for digestibility by alpha-amylase (McCleary et al., 1994) and stimulated intestinal fluid (Board of Trustees, 1995)

Production of Stably Transformed Sorghum Lines and $T_1$ Plants Containing Barley TRXh Using a cDNA library from scutellum tissues of barley (constructed by R. Schuurink, UCB), a full-length gene for thioredoxin h (trxh; FIG. 20) was isolated and characterized (Calliau, del Val, Cho, Lemeaux, Buchanan, unpublished). The full-length cDNA clone has been placed into expression vectors with the hordein promoters plus the targeting sequence as described (Cho et al, unpublished) is used for sorghum transformation. This vector, pdBhssBTRXN-2, contains the 0.43-kb $B_1$-hordein promoter plus its signal sequence, barley trxh (btrxh) and nos.

Sorghum is transformed by the methods of Cho et al., (1998b, 1999b, 1999c, 1999d, 2000) to give rise to highly regenerative green tissues. These tissues contain multiple, light-green, shoot meristem-like structures, which were characterized as such in barley because they expressed a gene associated with maintenance of the shoot meristematic state, a knotted I homologue (Zhang et al., 1998). Target tissues such as these highly regenerative tissues, which a high percentage of totipotent cells capable of sustained cell division and competent for regeneration over long period, represent a high-quality target tissue for transformation. They can be maintained for more than a year with minimal loss in regenerability (Cho et al., 1998b, 1999b, 1999c, 1999d, 2000; Kim et al, 1999; Ha et al, 2000). In addition, the result from genomic DNA methylation analyses (Zhang et al. 1999b) showed that barley plants regenerated from these highly regenerative tissues were less variable in terms of methylation pattern polymorphism and agronomic performance than those regenerated from callus maintained in the embryogenic state.

Media developed for the other cereals and grasses are utilized for optimizing the response of the sorghum variety, TX430, to produce high quality, green regenerative tissues with sorghum similar to those observed with other cereals and grasses. Such tissues have been used successfully for stable transformation with all varieties tested. Briefly, this method, the development of green, regenerative tissues, involves the initiation of embryogenic cultures from immature embryos of cultivar TX430. The medium giving the highest quality tissue is D'BC2 and DBC3 (Cho et al., 1998a–c, 1999d). Such media, containing copper, maltose, and cytokinins have been found to improve the quality and long-term regenerability of tissue from other cereal and grasses. Tissue developed on this medium is used as transformation targets using bombardment.

The desired DNA construct(s) containing barley TRXh are introduced into target cells via bombardment. Selection to identify transformants is via bialaphos, kanamycin, hygromycin, or other appropriate selection agents according to published procedures (Cho et al., 1998a–c; Lemaux et al., 1999). Small portion of putatively transformed calli are analyzed by PCR (Cho et al., 1998a–c) for barley trxh and transformed tissue is manipulated to regenerate plants (Cho et al, 1998a–c). Leaf tissue is tested for resistance to the selective agent, if possible, and as appropriate is analyzed by PCR for the transgene(s). Plants are grown to maturity to obtain $T_1$ seeds and homozygous $T_2$ plants.

Determination of Amounts and Activity of TRXh in Stably Transformed Sorghum

The activity of the barley thioredoxin h from the different production systems (targeted vs. nontargeted, i.e, with or without the signal sequence, respectively) and obtained with different fractionation procedures, as described above, is assayed using the DTNB [2',5'-dithiobis (2-nitrobenzoic acid)] method (Florencio et al., 1988) as described (Cho et al., 1999). The NTR and thioredoxin controls are prepared from wheat grains as described by Johnson et at (1987a, b).

Western Blot Analysis

Western blots are performed on extracts from selected transgenic lines as well as control seeds. Lots of 10 to 20 intact seeds are processed and analyzed for content of TRXh and NTR by SDS-PAGE and western blot procedures (Cho et al., 1999e).

Preparation of Seed Extract, Heat Treatment and Column Chromatography

Extracts are prepared, heat treated, and fractionated by column chromatography as described by Cho et al. (1999e).

Measurement of Thioredoxin h Activity

Thioredoxin h is assayed by the chloroplast NADP-malate dehydrogenase procedure as adapted for barley (Cho et al., 1999e).

Protein Determination

Protein is determined or measured according to Bradford (1976) using the Coomassie blue method with gamma-globulin as a standard. Protein content is confirmed by measuring total nitrogen in an automated gas analyzer or by standard micro-kjeldahl procedure.

Measurements in Changes in Abundance and Redox State of Endosperm Proteins

Transgenic sorghum seeds overexpressing barley thioredoxin h are the staring material used to demonstrate that increased levels of this protein cause altered digestibility. Preliminary mBBr measurements are also made with the genetically engineered grain. Changes in the redox state of endosperm protein are determined using the mBBr/SDS-PAGE procedure (Krobehel et al., 1992). As the major indigenous storage proteins in sorghum are known to be insoluble, propanol as well as the different aqueous endosperm extracts are monitored in the grain. Residues are extracted sequentially, as described above (A. Seed Digestibility) for the various protein fractions. Supernatant fractions of each extract is analyzed for protein and fluorescence by the mBBr/SDS-PAGE technique.

Dry grain, 1 g, from transgenic and null segregant lines are ground with a mortar and pestle in liquid nitrogen. When the liquid nitrogen evaporates, 3–6 ml of 30 mM Tris-HCl, pH 7.9 buffer containing 1 mM EDTA and 1 mM mBBr is added and mixed for 1 min. After thawing the extract is incubated 15 min, centrifuged (10 min at 12,000× g), extracted sequentially with salt, propanol, and borate solutions as described above (A. Seed Digestibility). Sixty µg protein samples are loaded onto a 10–20% SDS-polyacrylamide gradient gel as described above. Following electrophoresis (1 h, constant current of 30 mA), gels are soaked for 2 h in 12% (w/v) trichloroacetic acid and transferred to a solution containing 40% methanol and 10% acetic acid for 12 h to remove excess mBBr. Gels are scanned for fluorescence with a UV light source (365 nm) and stained for protein with Coomassie blue.

Measurements of Change in Digestibility and Solubility of Endosperm Proteins in $T_1$ Heterozygous and $T_2$ Homozygous Sorghum Grain In parallel with the in vitro experiments (Oria et al., 1995), the extent that in vivo thioredoxin-mediated reduction contributes to the digestibility and solubility of sorghum endosperm proteins is determined. The extent of solubilization of protein is measured using the ratio of the soluble to the insoluble protein in the transgenic, relative to a null segregant. Extracts are prepared in parallel without mBBr labeling and tested for susceptibility to digestion by simulated gastric and intestinal fluids are described above (Example 3). The proteins from the different transgenic grain also are reduced with thioredoxin and glutathione as described above (A. Seed Digestibility).

Measurements of Change in Digestibility of Starch in $T_1$ Heterozygous and $T_2$ Homozygous Sorghum Grain As in the case of the kafirin storage proteins, the ability of the overexpressed thioredoxin h to enhance the digestibility of starch with alpha-amylase is determined. The starch is isolated from both transgenic and null segregant lines and its digestibility tested in vitro with alpha-amylase as described above (B. Isolation and Digestibility of Starch). Because of their association with starch granules, an increase in the digestibility of the kafirin proteins is accompanied by an increase in the digestibility of the starch.

Thioredoxin h Overexpressed in Sorghum to Improve Digestibility of Grain Protein The above-noted digestibility of the different protein fractions (albumin/globulin, kafirin, glutelin) is tested with simulated gastric and intestinal fluids. The results from the transgenic grain overexpressing barley TRXh is compared to those with the null segregant to demonstrate improvement in digestibility in the transgenic grain.

Example 6

Improvement of Dough Quality

In U.S. application Ser. No. 08/211,673 (expressly incorporated by reference), dough quality was improved by reducing the flour proteins using the NADP/thioredoxin system. Without being bound by theory, reduced thioredoxin specifically breaks intramolecular sulfur-sulfur bonds that cross-link different parts of a protein and stabilize its shape. When these cross-links are broken the protein can unfold and supposedly link with other proteins in dough, creating an interlocking lattice that forms an elastic network. The dough rises because the network helps trap carbon dioxide produced by yeast during the fermentation process. It was proposed that the reduced thioredoxin, in turn, reduced the gliadins and glutenins in flour letting them recombine in a way that strengthened the dough. Reduced thioredoxin facilitated their forming a protein network during dough making. Treatment of intermediate or poor quality wheat flour (Apollo cultivar) with *E. coli* thioredoxin, NADP-thioredoxin reductase, and NADPH showed dough strengthening (higher farinograph measurements) and improved loaf volume and viscoelasticity in comparison with untreated flour. Higher farinograph measurements of dough correspond to improved dough strength and improved baked good characteristics such as better crumb quality, improved texture and higher loaf volume.

Wheat Bread Baking Studies and Farinograph Measurements

The baking tests are carried out by using a computer operated PANASONIC bread maker to demonstrate improved quality of dough made using flour prepared from the transgenic seeds of the present invention.

---
Composition of bread:

Control:

| Flour*: | 200 gm (dry) |
|---|---|
| Water: | 70% hydratation |
| Salt (NaCl): | 5.3 g |
| Yeast: | 4.8 g (Saccharomyces cerevisiae) (dry yeast powder) |

*Flour samples are obtained from transgenic and non-transgenic wheat (cv. Anza, Thesee, Apollo, Arbon, and other animal feed grades having from poor to good baking quality), sorghum, corn, and rice.

*Flour samples are obtained from trangenic and non-trangensic wheat (cv. Anza, These, Apollo, Arbon, and other animal feed grade and other grades having from poor to good baking quality), sorghum, corn, and rice.

Experimental Conditions

Flour and salt are weighed and mixed

The volume of water needed to reach a hydration of 70% was put into the bread maker.

The mixture of flour and salt is added to the water and the baking program is started by the computer. The complete program lasts about 3 hrs 9 min and 7 secs.

Yeast is added automatically after mixing for 20 min and 3 secs.

The program operating the Panasonic apparatus is:

| | | Mixing | |
|---|---|---|---|
| Segments | Duration | Conditions | Heating |
| Mixing | 00:00:03 | T1 | off |
| Mixing | 00:05:00 | T2 | off |
| Mixing | 00:05:00 | T1 | off |
| Rest | 00:10:00 | TO | off |
| Mixing | 00:17:00 | T2 | off |
| Mixing | 00:07:00 | T1 | off |
| Rest | 00:30:00 | TO | to reach 32° C. |
| Mixing | 00:00:04 | T1 | 32° C. |
| Rest | 01:15:00 | TO | 32° C. |
| Baking | 00:14:00 | TO | to reach 180° C. |
| Baking | 00:26:00 | TO | 180° C. |

Mixing Conditions: TO = no mixing (motor at rest)
T1 = normal mixing
T2 = alternately 3 second mixing, 3 second rest After the dough is formed, farinograph readings are taken as described in U.S. application Ser. No. 081211,673. Bread loaf volume is measured at the end of the baking, when bread loaves reach room temperature.

Farinograph readings of dough produced from flour made from transgenic wheat seeds of the invention are at least about 10–20% higher and are maintained about 40% longer than dough produced from flour made from non-transgenic seeds. Bread produced from flour made from transgenic seeds of the invention has at least about 5% and up to about 20% increased volume in comparison to bread produced from flour made from non-transgenic seeds. Bread-like products made from transgenic flour of cereals that normally produce a nonglutenous flour, for example, rice, hold together and hold gas better than products produced from the flour of their nontransgenic counterparts. They also show at least a 3% increase in loaf volume when compared to their nontransgenic counterparts.

Example 7

Effect of Glucose-6-Phosphate Dehydrogenase on Reduction of Proteins in Extracts of Homozygous vs. Null Segregant Wheat Grain Overexpressing Thioredoxin h Samples were from the salt-soluble fractions (albumin and globulin) of the trasngeic and null segregant wheat grain overexpressing wheat thioredoxin h. Reactions were carried out in 30 mM Tris-HCl buffer, pH 7.9, in a final volume of 100 µl. The complete reaction mixture contained 10 pmol glucose-6-phosphate, 0.25 pmol NADP, 2 units glucose-6-phoshate dehydrogenase (Bakers Yeast, Type XV, Sigma, St. Louis, Mo.), plus or minus 1.5 µg NTR (*Arabidopsis*), and 80 µg protein. Other treatments, where omission of one or two component(s) of the NADPH-generating system, were as indicated. The negative control was the extracted protein alone. As a positive control NADPH was used in place of NADP/glucose-6-phoshate/glucose-6-phosphate dehydrogenase.

After incubation at 37° C. for 60 min, 100 nmol mBBr was added to the reaction mixture, and the reaction was continued for 15 min. Ten ul of 100 mM 2-mercaptoethanol was added to stop the reaction and derivatize excess mBBr. An appropriate amount of 4× Laemmeli sample buffer was added and the samples were applied onto 10–20% polyacrylamide gel in the presence of SDS. Electrophoresis was carried out at room temperature at 7 mA/gel for 16 hours.

Flourescence of sulfhydryl containing proteins on gels was captured by Gel Doc 1000 (Blo-Rad), protein was stained by 0.025% Coomassie Brilliant Blue G-250 in 10% acetic acid.

For visualizing the effect of glucose-6-phosphate dehydrogenase (FIG. 23): in the presence of NTR, comparison of lanes 2 vs. 4 (−NADP) and lanes 5 vs 7 (+NADP) (+NTR gel on the left); in the absence of NTR, compare lanes 1 vs. 3 (−NADP) and lanes 2 vs. 4 (+NADP) (−NTR gel on the right). The maximal increase in reduction effected by glucose-6-phosphate dehydrogenase was observed in the presence of NTR, without NADP (lane 2 vs. lane 4, gel on the left). Note also the greater reduction of NTR in lane 4 vs. lane 2.

Figure 23:
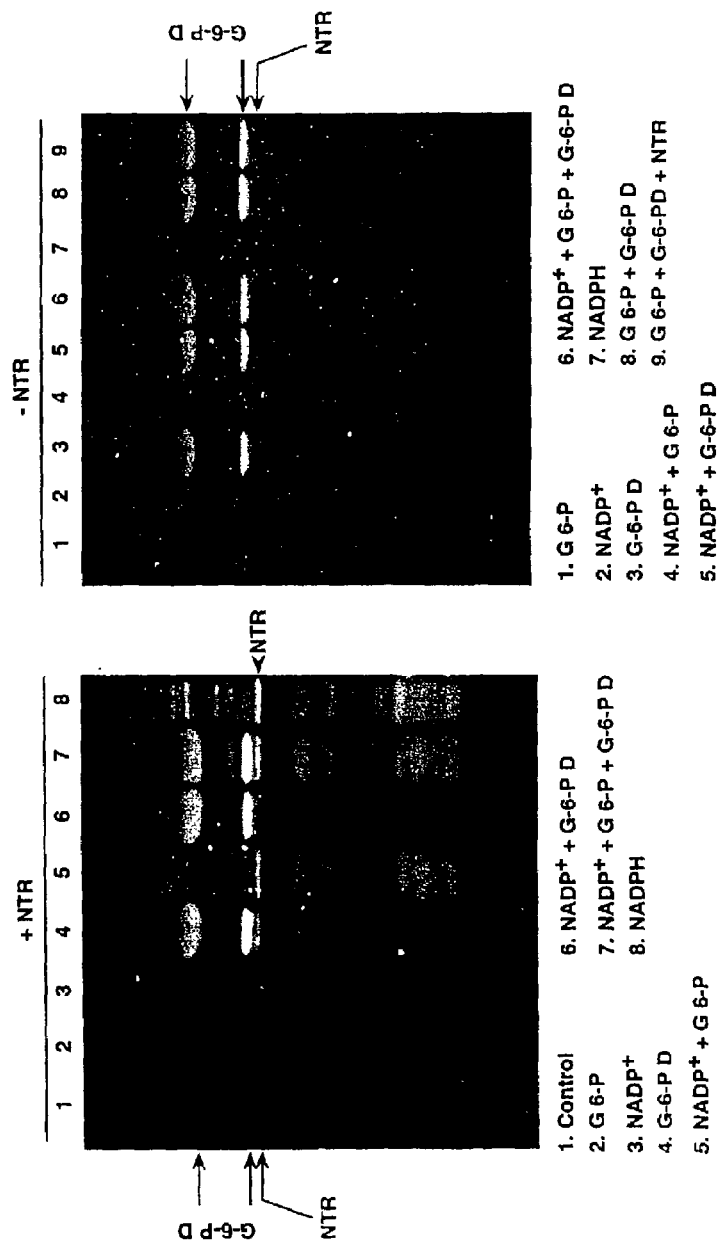
FIG. 23 shows the effect of glucose-6-phosphate dehydrogenase on the reduction of proteins in extracts of transgenic wheat overexpressing thioredoxin h in the presence of glucose 6-phosphate and *Arabidopsis* NTR:+/–NTR.
Figure 24:
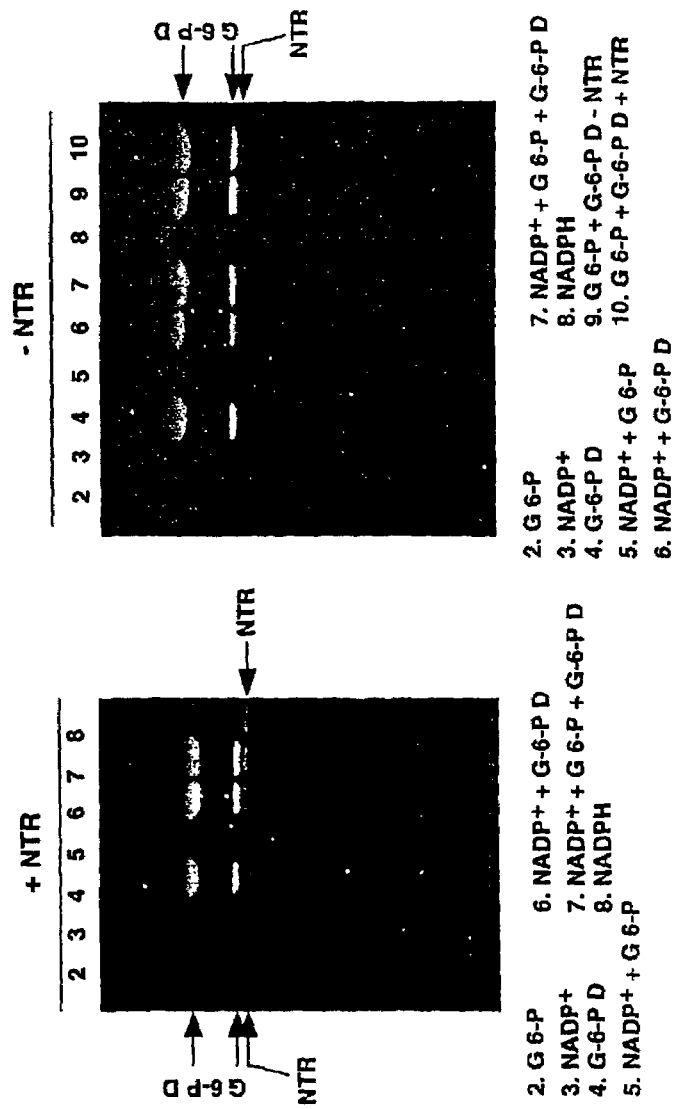
FIG. 24 shows the effect of glucose-6 phosphate dehydrogenase on the reduction of proteins in extracts of null segregant derived from wheat grain overexpressing thioredoxin h in the presence of glucose 6-phosphate and *Arabidopsis* NTR:+/–NTR.

With the null segregant (FIG. 24), note the greater reduction of NTR in the presence of glucose-6-phosphate dehydrogenase (lane 4 vs. lane 2) but a lower extent of the reduction of the smaller target proteins (lane 4) compared to the corresponding treatment (lane 4) with the transgenic extract (FIG. 23).

Example 8

Redox Status of Thioredoxin-Linked Proteins in Seeds

The redox status of the thioredoxin-linked proteins in seeds was investigated in a series of experiments taking advantage of transgenic wheat grains overexpressing thioredoxin h produced using a B-hordein promoter and a signal sequence that targeted the linked protein to the protein body (Cho et al., 1999). Ground grain was extracted sequentially for albumins, globulins, gliadins, and glutenins. The fluorescent probe monobromobimane (mBBr), which preferentially binds to sulfhydryl groups of reduced proteins, was only present in the initial aqueous solvent used for extraction (buffer plus salt). The rationale is that any protein that existed in the sulfhydryl form in the dry grain will be labeled at this step. Two types of analyses were carried out: one in which extracts were labeled without treatment, and a second in which extracts were incubated with two components of the NADP/thioredoxin system—NADPH and NADP-thioredoxin reductase—prior to adding mBBr. In this treatment the only thioredoxin h present in the grain is at either the control or overexpressed level. In each of these experiments we compared the proteins that were labeled with mBBr in the homozygous line with those in the corresponding null segregant. Only data on the albumin fraction are being presented in this report.

Materials and Methods

Materials and chemicals. Transgenic wheat (*Triticum aestivum* L. cv. Yecoro Rojo) lines overexpressing thioredoxin h were generated as previously described for cereals (Cho et al, 1999; Kim et al. 1999). *Chlamydomonas reinhardtii* thioredoxin h, and *Arabidopsis thaliana* NTR were kind gifts of J. -P. Jacquot (Université de Nancy I, Vandoeuvre, France).

Chemicals. Reagents for IEF and SDS-polyacrylamide gel electrophoresis were purchased from Bio-Rad Laboratories (Hercules, Calif.). Monobromobimane (mBBr) or Thiolite was obtained from Calbiochem Co. (San Diego, Calif.). Other chemicals and biochemicals were purchased from commercial sources and were of the highest quality available.

Methods

Protein Extraction. Wheat grains ($3^{rd}$ generation) from greenhouse-grown plants were ground in a Wiley Mill fitted with a 40-mesh screen. One gram ground wheat grain was extracted with 20 ml 5% NaCl in 20 mM Tris-HCl, pH 7.5 containing 2 mM mBBr at 25° C. for 30 min. Excess mBBr was derivatized with 2-mercaptoethanol. The resultant supernatant fraction was dialyzed against 100-fold excess of the Tris-HCl buffer overnight at 4° C. After centrifugation (15 min at 27,000×g), the supernatant fraction (containing the albumins) was divided into 2-ml aliquots and stored at −80° C. until use.

In vivo and in vitro Reduction of Protein. The control experiments were designed to ascertain the in vivo reduction status of proteins in the ground transgenic grain with no extra treatment. A second treatment was designed to visualize the effect of overexpressed thioredoxin h in the presence of excess reducing power by adding NADPH and NTR. In the latter case the two components were incubated first for 10 min at 37° C., added to the grain extract without mBBr and then incubated for 60 min at 37° C. mBBr was then added, the solution incubated for 15 min, and the sample processed as described above.

Reversed Phase HPLC Chromatography. Thawed aliquots of the albumin extracts from equivalent amounts of homozygote and null segregant grain were clarified by centrifugation (10 min at 14,000 rpm). A two-ml filtered sample was injected into a Sephasil Protein C4 column (5 um ST 4.6/250) that had been equilibrated with Buffer A ($H_2O$ containing 0.1% trifluoroacetic acid or TFA). After washing with 12 ml Buffer A to remove unbound protein, the column was eluted with a gradient of 20% to 80% Buffer B (acetonitrile containing 0.1% TFA) on a BioCad Sprint System (P E Biosystems) equipped with both fluorescent and UV detectors. One-ml fractions were collected. The fractions containing protein were either lyophilized or treated as indicated below.

SDS-Reducing 1D PAGE. mBBr-labeled albumin samples, from the reversed phase step above, that had been previously reduced by thioredoxin h were dissolved in Laemmli sample buffer, and subjected to electrophoresis in 10 to 20% Criterion gel at a constant voltage of 150 on a Criterion Precast Gel System (Bio-Rad). After electrophoresis, the image of fluorescent protein bands was captured using Quantity One on a Gel Doc 1000 (Bio-Rad) over a 365-nm UV light box. The proteins were then stained with 0.025% Coomassie brilliant blue G-250 in 10% acetic acid, and de-stained in the same acetic acid solution without the dye. Protein patterns were captured as above using a white light instead of an UV light box. Proteins were quantified using the Volume Tools of Quantity One Quantitation Software, Version 4 (Bio-Rad). The mean value—i.e., the intensity of the pixels inside the volume boundary-was measured for each protein band in question.

IEF/SDS-Reducing 2D PAGE. A two-ml aliquot of each of the original albumin samples was thawed and clarified extract was desalted and concentrated in Ultrafree-15 Centrifugal Filter Unit with 5,000 MWCO membrane. The concentrated sample was buffer-exchanged with 1-ml rehydration buffer twice. The equilibrated sample was added to IPG strips (pH 5–8), rehydrated for 10 h at 20° C. in rehydration tray on the Protean IEF Cell (Bio-Rad). Isoelectric focusing was performed in a Protean IEF Cell using a preset program with 35,000 total voltage-hour and an upper voltage limit of 8,000 V. After termination of isoelectric focusing, the IPG strip was removed and dipped in Equilibration Tricine buffer for 20 min. Then the strip was applied horizontally to a 16.5% Peptide Criterion gel, and electrophoresis in the second dimension was performed at constant 150 V at 25° C. for 1.5 h on a Criterion Precast Gel System (Bio-Rad). Fluorescent and protein images were captured as described above.

Identification of Protein Targets

In-gel Digestion and Peptide Fractionation

Reduction/alkylation and trypsin in-gel digestion of mBBr-labeled proteins were carried out essentially by the procedure described by Shevchenko et al. (1996). Extracted trypsin-digested peptides from gels were separated by microbore C18 reversed-phase column (1 mm×25 cm; Vydac, Hesperia, Calif.) on ABI 172 HPLC system (Applied Biosystems). After injection of the sample, the column was washed with 95% solvent A (0.1% TFA in water), 5% solvent B (0.075% trifluoroacetic acid in 70% acetonitrile) for 5 min for column equilibration. The column was eluted first with a linear gradient from 5% to 10% solvent B for 10 min, second with a linear gradient from 10% to 70% B for 70 min that increased to 90% solvent B over 15 min.

Amino Acid Sequence Analysis of Peptides

Sequence analysis of C18-purified peptides was performed at the Molecular Structure Facility (University of California, Davis) by automated Edman degradation on an ABI model 494 Procise sequencer (Applied Biosystems). Nontarget proteins were analyzed by nano-electrospray ionization tandem mass spectrometry (nano ESI/MS/MS) using a hybrid mass spectrometer QSTAR (Perkin-Elmer). Nanospray capillaries were obtained from Protana (Odense, Denmark). For nano ESI/MS/MS, in gel digested peptide mixture was analyzed directly without any C18 column fractionation.

Results and Discussion

Figure 25:
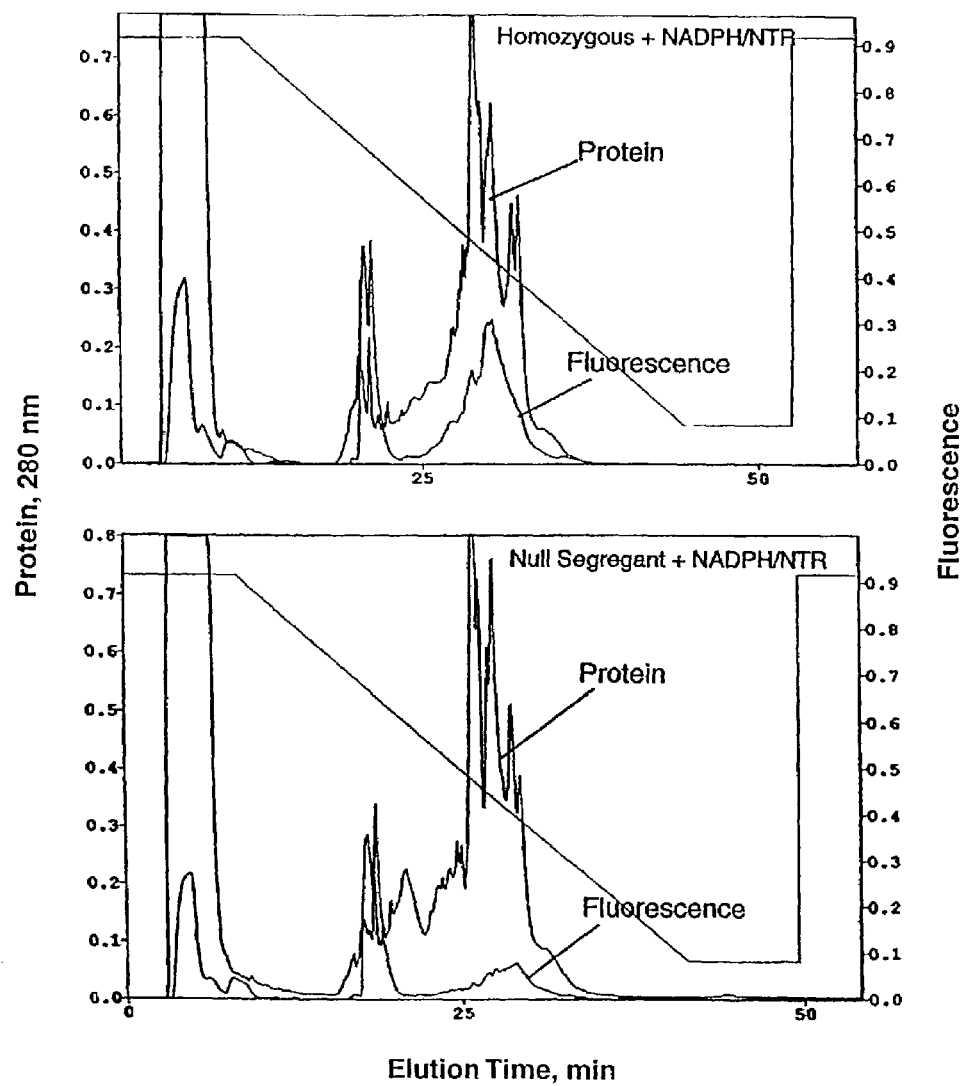
FIG. 25 shows an elution profile of albumin fraction of transgenic wheat on reversed-phase HPLC.

Analyses revealed that there was extensive fluorescent label in the albumin fraction using the above labeling and protein fractionation techniques. The relative reduction of protein (area of fluorescence/protein) was calculated from the elution profile obtained on a C4 reversed phase column. A significant (ca. 11%) difference was noted in the reduction of proteins from the homozygous wheat line overexpressing thioredoxin h relative to the null segregant counterpart (Table 9, Experiment I). Moreover, with added NADPH and NTR, this difference increased to 3.9-fold (Table 9, Experiment II). As there were notable differences in the reversed phase column profiles of the homozygote and the null segregant extracts with NADPH and NTR (FIG. 25), the protein fractions from the two lines were further analyzed by electrophoresis (first 1D SDS-PAGE and then 2D IEF/SDS-PAGE).

TABLE 9

Relative Reduction of Proteins in the Albumin Fraction from a Homozygous Line of Wheat Overexpressing Thioredoxin h vs. the Null Segregant either without (Experiment I) or with Reduction by NADPH and NTR (Experiment II).

| Experiment | Line | Relative Reduction* | Homozygous/Null Segregant |
|---|---|---|---|
| I. −NADPH/NTR | Homozygous | 0.10519 | 1.11 |
|  | Null Segregant | 0.0946 |  |
| II. +NADPH/NTR | Homozygous | 0.23211 | 3.91 |
|  | Null Segregant | 0.05927 |  |

*Area of fluorescence of peaks divided by area of protein of peaks. Area is expressed as micro-Absorbance Units (AU) × sec.

Figure 26:
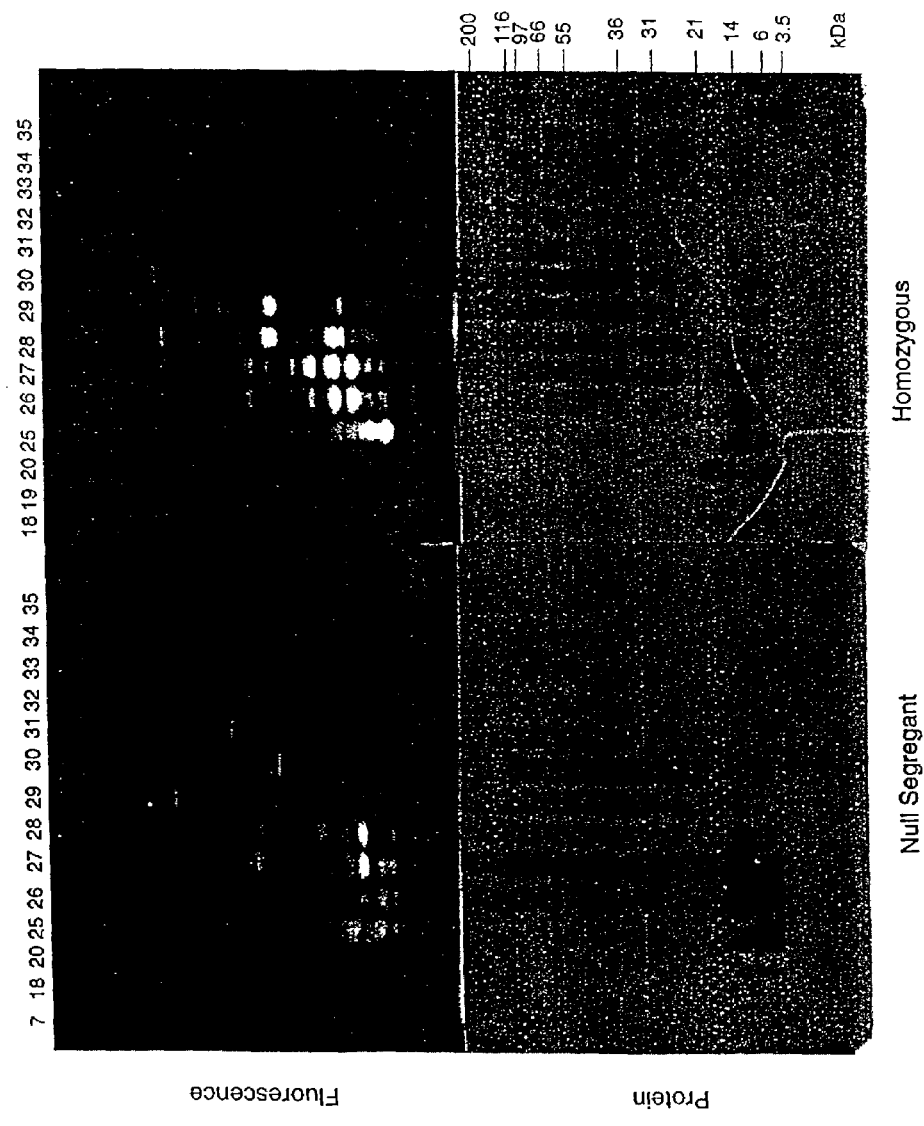
FIG. 26 shows a one-dimensional SDS/PAGE gel of reversed phase albumin fractions from transgenic wheat with NADPH and NTR.
Figure 27:
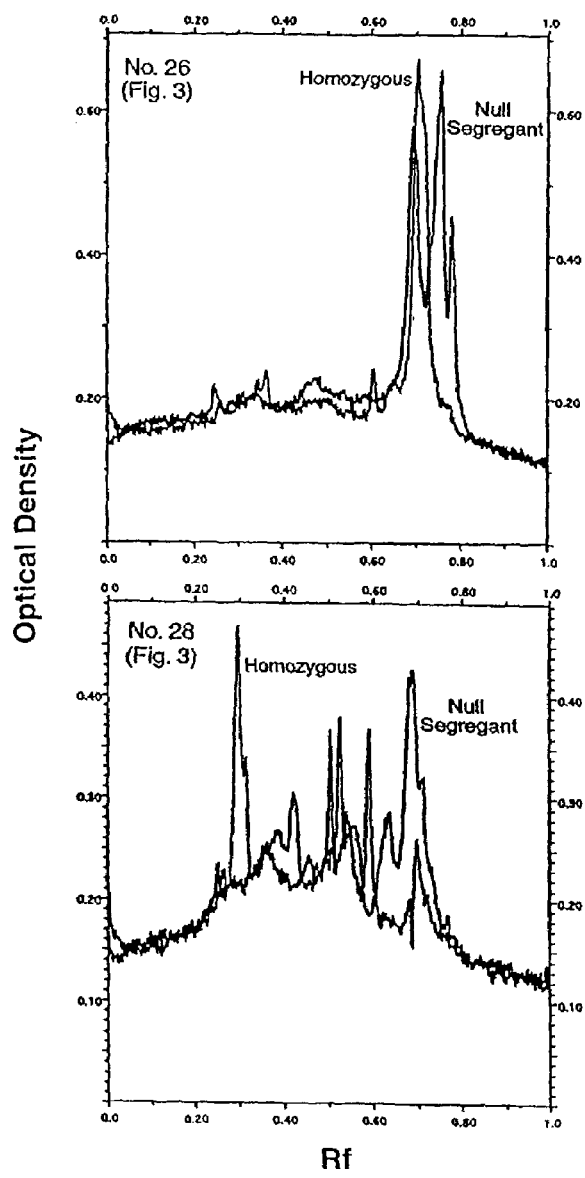
FIG. 27 shows a scan profile of protein fractions 26 and 28 from reversed phase HPLC C4 column after separation by SDS-PAGE.

FIG. 26 shows a composite of the fluorescence and protein profiles of selected reversed phase-HPLC fractions of the albumins from the homozygous wheat line overexpressing thioredoxin h (right) and the corresponding null segregant wheat line (left) following treatment with NADPH and NTR. This figure illustrates the upper limit of the proteins that could be reduced in the dry grain of the homozygous wheat line overexpressing thioredoxin h when NADPH and NTR are not limiting. It is interesting to note that the protein patterns from homozygous and null segregant lines were not the same. There seemed to be a decrease in the abundance of protein from the 3.5 to ca.16 kDa region in the homozygote (designated by an asterisk in FIG. 26), particularly an almost complete absence of the band at approximately 3.5 kDa. It is noted that thioredoxin h was detected in fractions 30 to 35 with gel immunoblots (data not shown). Scanning of a 1D SDS-PAGE developed with two of the fractions differing in protein profile from the two wheat lines (nos. 26 and 28) further illustrates the difference in protein pattern eluted from the reversed phase column (FIG. 27). The other fractions analyzed (nos. 25–32) also showed dissimilar protein profiles. In addition to indication of a change in the distribution of proteins in the homozygote, the results presented so far revealed that the albumin fraction contained numerous proteins targeted for reduction by thioredoxin.

Figure 28:
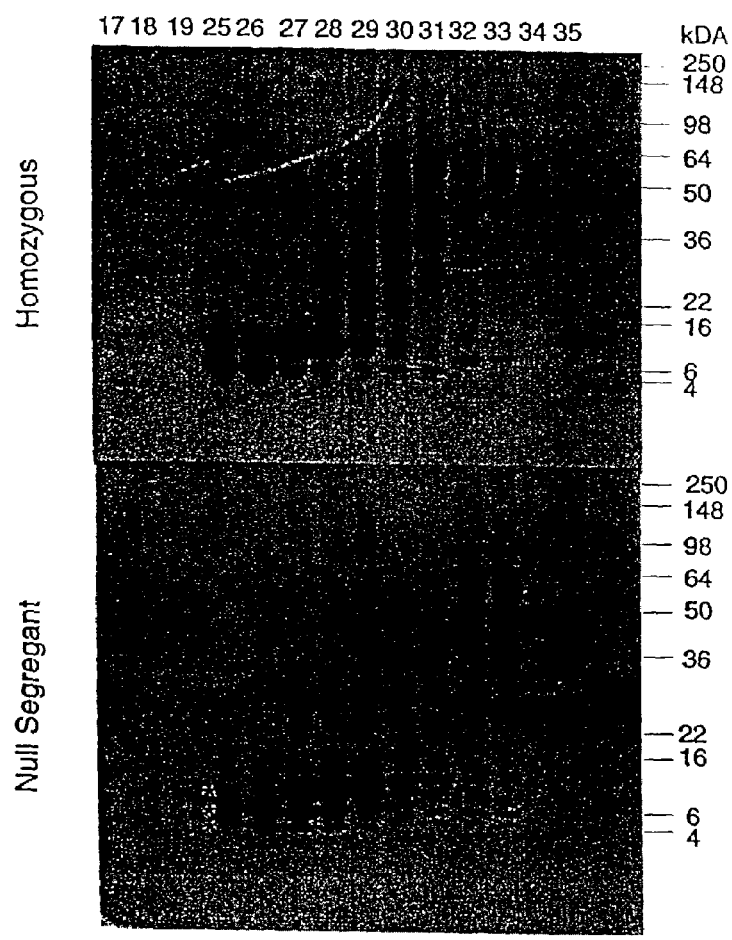
FIG. 28 shows a one dimensional SDS-PAGE gel of reversed phase albumin fractions from transgenic wheat without NADPH and NTR.

A change in the distribution of albumin proteins was also observed when comparing untreated extracts from the homozygote overexpressing thioredoxin h and the null segregant (FIG. 28). Here we observed a shift in the homozygote similar to that reported above for the NADPH/NTR-treated extracts. Again, especially noteworthy was the general decrease in proteins in the 3.5 to 16 kDa regions in the homozygote and the accompanying absence of the 3.5 kDa band (see asterisk, FIG. 4, top panel). Quantitation revealed that proteins in the 3.5–16 kDa region, that included the alpha-amylase and alpha-amylase/trypsin inhibitors, were reduced by 22% in the homozygote relative to the null segregant (Table 10). On the basis of these results, it appears that the overexpression of thioredoxin effected a change such that the level of certain proteins is decreased. The basis for this change is under investigation.

TABLE 10

Effect of Overexpressing Thioredoxin h on the Abundance of Albumin Proteins in the 3.5 to 16 kDa Range. The numbers were obtained with the gels shown in FIG. 28.

| Grain | Mean Optical Density | Relative Abundance |
|---|---|---|
| Homozygote | 2,350.0 | 78 |
| Null segregant | 3,007.5 | 100 |

Figure 29:
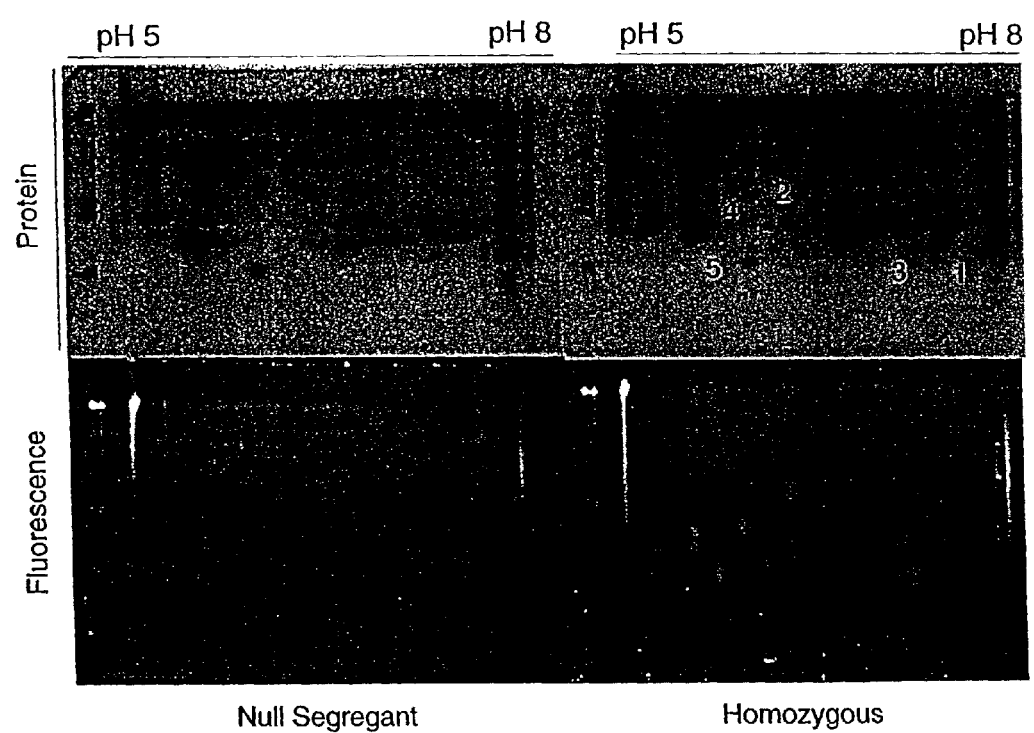
FIG. 29 shows an isoelectric focusing gel (IEF) for pH 5–8/Tris-Tricine (16.5%) PAGE of albumin fraction from transgenic wheat overexpressing thioredoxin h.
Figure 33:
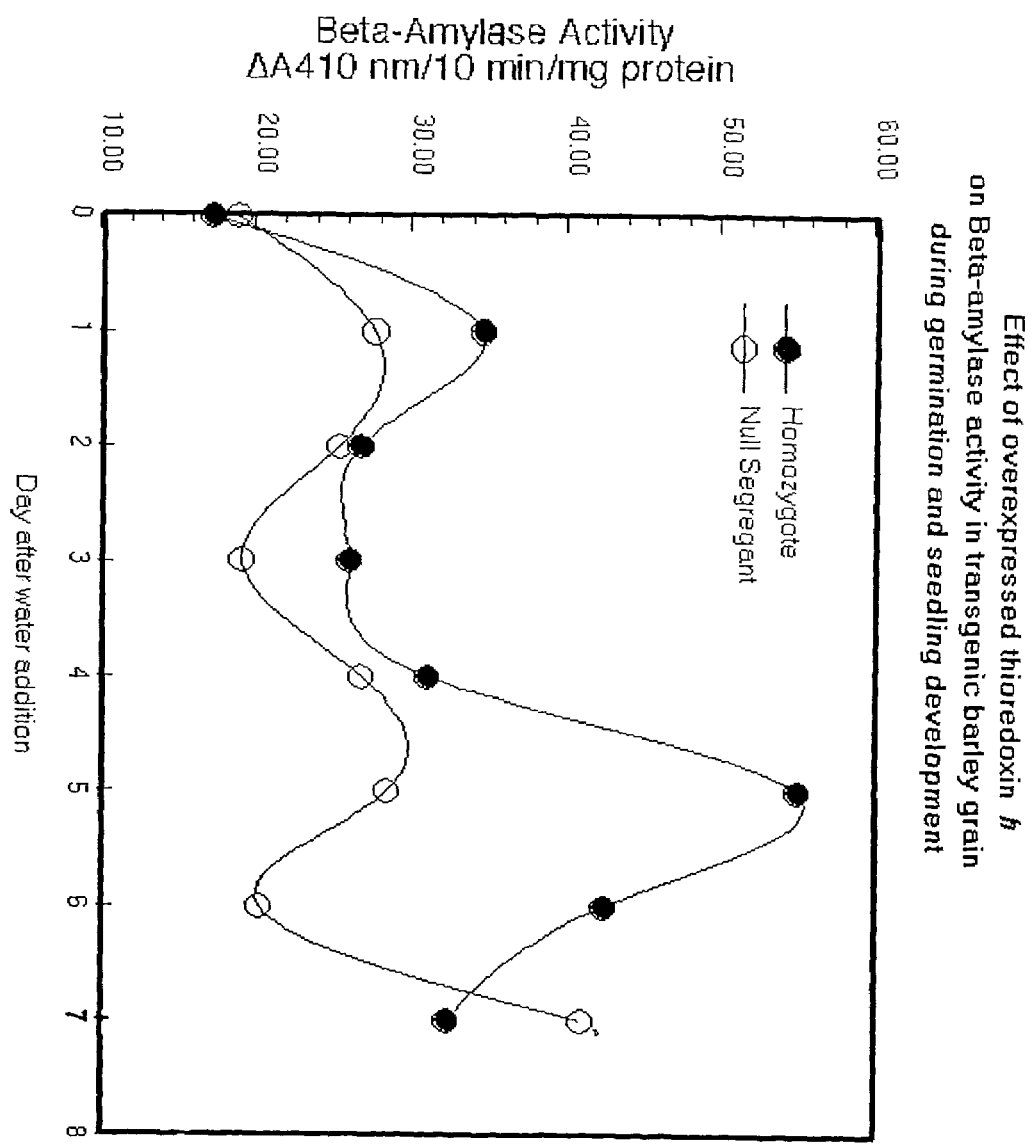
FIG. 33 shows the effect of overexpressed wheat thioredoxin h on the activity of B-amylase.

The question arises as to whether, in addition to changing the protein distribution in the albumin fraction, overexpressed thioredoxin h changed their redox state. We have sought an answer to this question by analyzing extracts of the null segregant and homozygote, without treatment with NADPH and NTR, by mBBr/2D IEF/SDS-PAGE (FIG. 29). It may be seen that a number of proteins were more reduced (more fluorescent) in the homozygote. Most of the prominent protein spots were of low molecular mass. When comparing the 2-D gels from the two lines, five proteins were observed to be more highly reduced in extracts of the homozygote (spots 1–5, FIG. 29).

Amino acid sequence analysis led to the identification of three of the purified proteins as wheat alpha-amylase and alpha-amylase/trypsin inhibitors: spot #1 was an alpha-amylase inhibitor isoform with a calculated pI of 6.66, #3 was an alpha-amylase/trypsin inhibitor and #4 was a mixture of an alpha-amylase inhibitor isoform (pI 5.23) plus thioredoxin h (Table II). Alpha-amylase inhibitors are reported to be the major cause of Baker's asthma (Amano et al., 1998). Significantly, the proteins in spots numbers 1 and 4 showed 100% identity with one of the alpha-amylase inhibitor allergens (0.19 inhibitor) (Maeda et al., 1985) whose allergenic properties were studied by Amano et al. (1998). The alpha-amylase inhibitors identified in this study can thus be considered isoforms of this allergen that show a similar molecular weight but different isoelectric points (FIG. 29). Members of this protein family were earlier found to be reduced by thioredoxin in vitro (Kobrehel et al., 1991), and when so reduced to show loss of activity and increased susceptibility to digestion by trypsin (Jiao et al., 1992; 1993). Based on this property, the alpha-amylase inhibitors of the transgenic grain would be more digestible (hyperdigestible) and less allergenic (hypoallergenic) compared to the null segregant counterpart (del Val et al, 1999 and references therein). The proteins inhibiting trypsin would not only lose activity and be more digestible, but would also be more sensitive to heat and susceptible to proteases (Jiao et al., 1992; 1993). The decreased abundance of the inhibitor proteins would also contribute significantly to lowering the total allergenicity and trypsin inhibitory activity of the homozygous grain. Spot #5 was identified as an isoform of thioredoxin h (Table III) that differed in molecular mass from its counterpart in spot #4 (FIG. 29).

Protein #2 of Table 11 showed strong homology to oat avenin (also called "seed storage protein") (Shotwell et al, 1990)—a wheat gliadin homolog. A minor spot adjacent to #2–#2'—that is not obvious in FIG. 29 was also sequenced and shown to contain an isoform of the wheat gliadin homolog identified in spot #2 (data not shown). As with the alpha-amylase inhibitors, the gliadin isoforms showed a similar molecular weight but different isoelectric points. It is noteworthy that gliadins containing disulfide groups, like the one identified in Table 11, are major food allergens in children (Varjonen et al., 1995). Furthermore, the allergenic effect of these proteins is alleviated following reduction by thioredoxin (Buchanan et al., 1997). On this basis, it can be concluded that the increased reduction of the representative gliadins identified in the homozygote would render the grain less allergenic. It is also possible that this increase in reduction could alter gastrointestinal processing so as to make the grain more tolerant for sufferers of coeliac disease where gliadins have been identified as the causative agent (Buchanan et al, 1997; del Val et al., 1999; Howdle and Blair, 1992; Kagnoff et al., 1982).

TABLE 11

Internal Amino Acid Sequence Analysis of Thioredoxin Target Proteins in Transgenic Wheat Overexpressing Wheat Thioredoxin h. The SwissPROT accession numbers are: Spot #1, P01085; #2, Q38794; #3, P16851; #4, P01084 (inhibitor), O64394 (thioredoxin); #5, O64394. Note that the alpha-amylase inhibitors showed similar molecular weights but different isoelectric points of 6.06 and 5.23 (see FIG. 5). By contrast, the thioredoxin h showed a similar isoelectric point but differed in molecular mass.

| No. | Internal Sequence | SEQ ID NO | Homologous protein | MW | Amino Acid | Identity Matches |
|---|---|---|---|---|---|---|
| 1 | SGPWMCYPGQAFQVPALPACR | 46 | Wheat alpha-amylase pI 6.66 inhibitor | 13,337 | 21/21 | 100.0 |
| 2 | DALLQQCSPVADMSFLR | 47 | Oat avenin, mature protein* | 22,072 | 14/17 | 82.4 |
| 3 | EYVAQQTCGVGIVGS | 48 | Wheat alpha-amylase/trypsin inhibitor | 15,460 | 15/15 | 100.0 |
| 4 | DCCQQLADISEWCR | 49 | Wheat alpha-amylase pI 5.23 inhibitor | 13,185 | 13/14 | 92.9 |
|   | KFPAAVFLK | 50 | Wheat thioredoxin h-type | 13,392 | 9/9 | 100.0 |
| 5 | IMAPIFADLAK | 51 | Wheat thioredoxin h-type | 13,392 | 11/11 | 100.0 |

*Wheat gliadin counterpart, also called "seed storage protein."

Conclusions

Thioredoxin h targeted and overexpressed in the protein body of wheat endosperm effected a significant (11%) increase in the reduction of proteins of the albumin fraction (S—S→2 SH). Included were alpha-amylase and alpha-amylase/trypsin inhibitors and gliadins containing disulfide groups. Members of the alpha-amylase inhibitor, alpha-amylase/trypsin inhibitor and sulfur-rich gliadin families were among the proteins found to be more reduced in the homozygote in vivo. Based on in vitro studies, increased reduction of the alpha-amylase/trypsin inhibitor would decrease its ability to inhibit trypsin and increase its susceptibility to heat and digestion by trypsin—i.e., make the protein hyperdigestible. Thioredoxin h overexpressed in wheat endosperm also effected a change in the distribution of proteins in the albumin fraction such that the level of those in the 3.5 to 16 kDa region, including the alpha-amylase and alpha-amylase/trypsin inhibitors, was decreased by 22% in the homozygote vs. the null segregant. Based on current evidence, a decreased abundance coupled with an increased reduction, would decrease the allergenicity of proteins of the albumin fraction. The alpha-amylase inhibitors and the glidains containing disulfide groups are, respectively, the major cause of Bakers' asthma in adults and wheat allergy in children. The above evidence is, therefore, in accord with the conclusion that the homozygote grain overexpressing thioredoxin h is hypoallergenic and hyperdigestible. More extensive reduction of the albumin proteins was observed in the homozygote when the reducing potential was not limiting—i.e., when the albumin fraction was incubated with NADPH and NTR to reduce indigenous thioredoxin h, that, in turn, reduced the target proteins. This finding suggests that grain engineered to increase the generation of NADPH (e.g., by overexpressing NTR and/or glucose 6-phosphate dehydrogenase) would enhance the reduction of endosperm proteins beyond that observed in the current study. The homozygote overexpressing thioredoxin h is being studied with respect to technological properties—i.e., allergenicity, digestibility and baking quality.

Example 9

Mitigation of Allergenicity in Transgenic Wheat Overexpressing Thioredoxin

Objective

The purpose of the present study was to determine the improvement in the allergenicity of proteins from transgenic wheat (Yecora Rojo) with overexpressed thioredoxin h using the atopic dog model described by Ermel et al. (1997). Allergenicity of the transgenic wheat was compared with that of its null segregant component by skin testing dogs for differential sensitivity to the isolated protein fractions.

Material and Methods

Transgenic wheat grain. Transgenic Yecora Rojo wheat grain with overexpressed thioredoxin h was produced as previously for barley (Cho et al., 1999; Kim et al., 1999). The homozygote contained about 25-x increase in the protein level of thioredoxin h relative to the null segregant.

Wheat sensitization of atopic dogs. From the original inbred colony of highly allergic dogs, breeding resulted in 2 litters (7FA, 7FC, 18 pups), some of which were immunized with commercial preparation of whole grain bread wheat (1:10 w/v) from Bayer. The allergic response to the preparation was followed systematically over a two-year period. The colony of high IgE-producing atopic dogs was maintained at the Animal Resources Service, University of California, Davis (Ermel et al., 1997). The animals, representing the $7^{th}$ generation of the colony, were cared for according to the principles in the NIH Guide for the Care and Use of Laboratory Animals. Either six or four of the 4-year-old dogs from the $7^{th}$ generation litters that had been sensitized to wheat were used in this study as indicated. Other wheat-sensitive dogs had been culled.

Skin tests. Procedures for skin tests to measure the type I hypersensitivity reaction have been described elsewhere (Ermel et al., 1997; Buchanan et al., 1997; del Val et al., 1999). In brief, Evans blue dye 0.5% (0.2 ml/kg) was injected intravenously 5 minutes prior to skin testing. Aliquots of 0.1 ml of the individual extracts were injected intradermally on ventral abdominal skin. The top concentration of allergen in 0.1 ml equivalent to 10 μg was serially diluted in log steps. Skin tests were read blindly by the same experienced observer scoring two perpendicular diameters of each blue spot.

Extraction of the wheat endosperm proteins. Albumin/globulin, gliadin, and glutenin fractions were isolated according to their differential solubility. One gram of grain was ground with a Wiley mill and extracted sequentially for the indicated times with 3 ml of the following solutions: (i) 0.5 M NaCl for albumins/globulins, 30 min (ii) 70% (vol/vol) ethanol for the gliadins, 2 hr and (iii) 0.1M glacial acetic acid for the glutenins, 2 hr. Samples were extracted using an electrical rotator at 25° C. and then clarified by centrifugation (25,000×g for 10 min at 4° C.). The resulting supernatant solutions were collected. After estimation of protein concentration, each fraction was serially diluted in physiological buffered saline (PBS) and then used for the skin tests.

Protein Assay. Protein concentration was determined by the Bradford method (Bio-Rad) using bovine gamma globulin as standard (Bradford, 1997).

Data Analysis. The data are presented as the logarithm of the lowest protein concentration giving an allergenic response. As the range of concentrations was quite broad, we applied the logarithm of the dose response for statistical analysis. To this end, we used the mean and the standard deviation of the logarithm obtained with the indicated number of dogs tested for the calculations by the complete randomized block design method. The statistical significance of the differences between the homozygote and the null segregant was determined by one-tailed sign rank test. The null hypothesis—assuming no difference in allergenic response between the homozygote and the null segregant—was tested against the alternative hypothesis—assuming a difference between two. The one-tailed sign rank tests were completed at 0.05 level of significance—i.e., a p value <0.05 reflected statistical difference.

Results

Table 12 demonstrates that the albumin/globulin and glutenin fractions did not differ significantly in allergenicity between homozygote and null segregant. Only the gliadin fraction showed a statistically significant difference—i.e., homozygote was less allergenic than null segregant (p=0.033). It seems likely, therefore, that the baker's asthma aeroallergen found earlier to be decreased in the transgenic grain was not detected in the present analyses because this protein is a member of the albumin fraction.

TABLE 12

Skin test response to wheat proteins.

| | Albumin | | Gliadin | | Glutenin | |
|---|---|---|---|---|---|---|
| | Null | HZ | Null | HZ | Null | HZ |
| Allergenicity† | 2.34 | 2.35 | 3.40 | 3.92 | 2.38 | 2.54 |
| S.D. | 1.10 | 1.54 | 2.72 | 2.27 | 1.32 | 1.42 |
| Significance (p value) | 0.481 | | 0.033 | | 0.182 | |

Null: null segregant,
HZ: homozygote

Null: null segregant, HZ: homozygote

Six dogs sensitized to a commercial preparation of wheat were used to test the albumins/globulins. These animals consistently showed a strong response to this fraction. Four dogs were used to test the gliadins and glutenins. Each of these animals displayed consistent sensitivity to these fractions over 2-year period.

† Mean of the logarithm of the lowest amount of protein giving a reaction. The corresponding responsive real numbers (ng protein) left to right were 219, 224, 2512, 8318, 240 and 347.

We have tried to determine whether the differences in the mean of the log number of the lowest concentration giving a reaction between homozygote and the null segregant could be applied to an authentic population of wheat-sensitive dogs (Table 13). To this end, we calculated the probability of an allergenic response induced within a given homozygote relative to the response of the null segregant. We based the calculation on the lowest amount of protein showing a reaction in 50% of the population responding to the null segregant.

TABLE 13

Probability of different proteins of transgenic wheat to induce an allergenic response with allergic population of dogs.

| | Albumin/globulin | Gliadin | Glutenin |
|---|---|---|---|
| | % Responding to test concentration | | |
| Null | 50* | 50* | 50* |
| HZ | 50 | 41 | 45 | allergenic response with allergic population of dogs.
Null: null segregant,
HZ: homozygote
*Corresponds to the probability that an allergenic response is induced in 50% of the population of sensitized dogs with the lowest protein concentration found for the null segregant. The 50% value (ng protein) was 219 for albumin/globulin, 2512 for gliadin and 240 for glutenins.

allergenic response with allergic population of dogs

Null: null segregant, HZ: homozygote

* Corresponds to the probability that an allergenic response is reduced in 50% of the population of sentitized dogs with the lowest protein concentration found for the null segregant. The 50% value (ng protein) was 219 for albumin/globulin, 2512 for giladin and 240 for glutenins.

On this basis, with the gliadin fraction, the homozygote showed about a 10% reduction in allergenicity relative to the null segregant. The corresponding numbers for the albumins/globulins and the glutenins are also included in Table 13, although they are not statistically significant. Nonetheless, with the glutenins, the homozygote continued to show a trend and was lower in allergenicity than the null segregant by about 5%. In the case of the albumins/globulins, there is no indication of a difference between homozygote and null segregant. Interestingly, these finding are similar to those obtained previously by applying reduced thioredoxin to the isolated Yecora Rojo protein fractions (Buchanan et al., 1997). That is, thioredoxin mitigated the allergenicity of the gliadins and glutenins but not of the albumins or globulins. This result is possibly due to the overexpressed thioredoxin h localized in protein bodies via the ER where major storage proteins, gliadins and glutenins, are stored in endosperm tissue. Testing of additional glutenin-sensitive dogs should show whether or not the glutenin difference is significant.

Conclusions

As determined by skin tests with the dog model, thioredoxin h overexpressed in transgenic grain effected a decrease in the allergenic potential of the gliadin fraction. On the basis of this difference, we calculated a 10% reduction in allergenicity in the gliadin fraction of the homozygous transgenic grain with overexpressed thioredoxin h (homozygote) compared with the null segregant.

Example 10

Isolation of the Glucose-6-phosphate Dehydrogenase Gene from *Hordeum vulgare*

Introduction

There are promising demonstrations of the effects of adding the components of a naturally occurring redox system, NADP/thioredoxin system (NTS), to grains in vitro that lead to the production of value-added grains as well as human and animal neutraceuticals. There are three components to this system: thioredoxin (TRX), NADP-thioredoxin reductase (NTR) and NADPH.

Thioredoxins are small ubiquitous proteins (12–14 kDa), that play a variety of physiological roles in the animal, plant and bacterial kingdoms (Holmgren 1985). The protein contains a disulfide bridge between two cysteine residues in the active center, WCGPC (Trp-Cys-Gly-Pro-Cys) (SEQ ID NO: 1), which in heterotrophic tissues is reduced by NTR (Holmgren, 1985). Higher plants are known to possess two types of thioredoxin systems, ferredoxin/thioredoxin system (FrS) and NTS, and three types of thioredoxins, m, f, and h (Jacquot et al., 1997). The NTS is analogous to the system in animals and most microorganisms where thioredoxin (h-type in plants) is reduced by NTR and NADPH is used as an electron donor (Johnson et al., 1987a; Florencio et al, 1988; Suske et al., 1979).

$$NADPH + H^+ + TRX\ h_{ox} \xrightarrow{NTR} NADP + TRX\ h_{red}$$

The driving force of the reaction is the source of electrons, NADPH. This coenzyme can be generated through glucose-6-phosphate dehydrogenase (G6DPH), which catalyzes the first step of the oxidative pentose phosphate pathway (OPPP), namely the conversion of glucose-6-phosphate to 6-phosphogluconolactone. Concomitantly, NADPH is generated. The main function of G6PDH is to generate NADPH for anabolic metabolism, including fatty acid synthesis, amino acid, and ribose synthesis (Copeland ant Turner, 1987; Turner and Turner, 1980; Dennis et al., 1997).

G6PDH has been found in bacteria, yeast and animal tissues as a homodimer or a homotetramer with a subunit size of 50 to 57 kDa (Levy, 1979). In plants, at least two isoenzymes have been found, one in the cytosol and one in the plastid with approximately 65% to 75% identity in the amino acid sequences of the two enzymes (Herbert et al, 1979; Srivastava and Anderson, 1983). The plastidic G6PDH is regulated by covalent redox modification via the ferredoxin/thioredoxin system (FTS), whereas the regulation of the cytosolic isoform appears to be regulated by the ratio of $NADP^+/NADPH$ (Fickenscher and Scheibe, 1986; Buchanan, 1991). The studies of Wenderoth et al. (1997) show that the position of the cysteine residues in the two potato isoenzymes is completely different and that the two cysteine residues (Cys 149 and Cys 157) are involved in the redox regulation of plastidic G6PDH. The complete genomic plastidic clone from tobacco has been isolated and characterized. In addition complete cDNAs have been identified from a number of plant species, including tobacco, *Arabidopsis*, alfalfa, parsley, wheat and maize (Knight et al., 2001; Fahrendorf et al., 1995; Nemoto and Sasakuma, 2000; Redinbaugh and Campbell, 1998; Graeve et al., 1994; Batz et al, 1998).

The NTS has been implicated in a wide variety of biological functions. It appears to be involved in developmentally related processes (Brugidou et al., 1993), self-incompatibility (Li et al., 1995) and as a translocation element in sieve tubes (Ishiwatari et al., 1995). In cereals, NTS functions as a signal to enhance metabolic processes during germination and early seed development (Kobrehel et al., 1992; Lozano et al., 1996; Besse et al., 1996). Serrato et al. (2001) found two forms of thioredoxin h, which are most abundant in mature seeds. Thioredoxin h also functions in the reduction of intramolecular disulfide bridges of low molecular-weight cysteine-rich proteins, including thionins (Johnson et al, 1987b), protease inhibitors and α-amylase inhibitors (Kobrehel et al, 1991). Moreover, gliadins and glutenins, the major wheat storage proteins, are reduced by NTS (Kobrehel et al., 1992). The addition of NTS to wheat flour was shown to improve dough quality, apparently by reduction of intramolecular disulfide bonds of flour proteins. These bonds then undergo sulfhydryl/disulfide interchanges to form new intermolecular disulfide bonds, thereby contributing to further network formation and stronger doughs (Wong et al., 1993). In addition, it has been shown that reduction by NTS of disulfide protein allergens from wheat and milk in vitro decreased their allergenicity (Buchanan et al., 1997; del Val et al., 1999). The NTS treatment also increases the digestibility of trypsin and α-amylase inhibitors and β-lactoglobulin, a major allergen in milk (del Val et al, 1999). Snake venom neurotoxins are also reported to be reduced and inactivated by NTS (Lozano et al., 1994). A recent study with transgenic barley plants that overexpress wheat TRX h in the endosperm showed that the seed progeny have enhanced activity of a starch-debranching enzyme (pullulanase) in germinating barley seeds (Cho et al, 1999).

These promising demonstrations of the effects of adding the components of NTS in vitro to grains, and in one in vivo case to transgenic grains, open the doors to new avenues to produce value-added grains. In order to utilize genetic engineering approaches to the production of this grain, it is necessary to have the genes for the various components. The barley trx h and ntr genes were cloned and transgenic barley and wheat plants overexpressing TRX h and NTR have been produced and both barley TRX h and NTR were biochemically active (unpublished). TRX h and NTR in transgenic wheat grains were expressed at levels 2 to 20 times those of wild type. Now it is of interest to determine the effects of overexpressing another component, the generator of NADPH, that could limit the reactivity of the total NTS. Since a major function of G6DPH is the generation of NADPH, the introduction of the gene encoding this protein should be able to supply additional NADPH and possibly enhance the activity of NTS. The cDNA sequence of barley g6pdh is presented here and the nucleotide and deduced amino acid sequences are compared with known g6pdh sequences from other organisms.

Methods

Amplification of Barley cDNA Library

To amplify barley cDNA libraries, the bacterial strain SOLR was streaked on M9 minimal medium including thiamine and grown at 37° C. for 36 hrs. A single colony was chosen and inoculated into LB broth plus 30 mg/ml kanamycin for approximately 4 hrs. An aliquot of the barley cDNA library phagemid stock, unstressed Morex shoots (*Hordeum vulgare* L. cv. Morex) shoots from 5-day old seedlings grown in the dark was mixed with the bacterial culture and incubated for 15 min at 37° C. After incubation, cells were spread onto LB agar plates containing 30 mg/ml kanamycin and 100 mg/ml ampicillin (to select for the phagemid) and incubated overnight at 37° C. Colonies were collected and phagemids were isolated using a Qiagen plasmid maxi kit (Qiagen, UK).

Identification of Partial Fragment of Barley Genomic g6pdh

Two primers were designed based on the cDNA sequence of wheat glucose-6-phosphate dehydrogenase: WG6PD 7 (5'-TACTTGGAAAAGAGTTGGTCCA-3' (SEQ ID NO: 52)) and WG6PD 9R (5'-GATTCCATATTGAT-CAAAATATCC-3' (SEQ ID NO: 53)). PCR was performed in a programmable thermal controller (MJ Research, Inc, USA). The reaction mixture contained 400 nmol of each primer, 50 μM dNTPs, 40 U/ml pfu DNA polymerase (Staratagene, USA), and 20 μg/ml of barley genomic DNAs (HKK, from selected phagemids). The PCR product was analyzed using a 0.8% agarose gels. The 450 bp-band was excised and purified using Qiaquick gel extraction kit (Qiagen, UK) and sequenced using an automated sequencer.

Obtaining of the Complete cDNA Sequence of g6pdh

Based on the partial sequence of the barley genomic g6pdh fragment obtained above, two primers were designed: BG6PD 12R (5'-AGTGGTAAGAACAAACGGTTCGCA-3' (SEQ ID NO: 54)) and BG6PD 13 (5'-CAGATTGTAT-TCAGGGAGGACT-3' (SEQ ID NO: 55)). These primers, M13F and M13R were combined for PCR reactions for isolated cDNA phagemids as follows: M13F/M13R plus WG6PD 7/BG6PD 13, and M13F/M13R plus WG6PD 9R/BG6PD 12R. PCR products were gel-purified and sequenced. DNA sequence data of all PCR products were combined and the complete cDNA of barley g6pdh was determined.

Results

Identification of Partial Fragment of Barley Genomic g6pdh

Using PCR primers, WG6PD 7 and WG6PD 9R, resulted in an amplification product of approximately 500 bp-from barley genomic DNA. The nucleotide sequence of this fragment is highly homologous to the wheat g6pdhs gene. Two more primers were designed based on this fragment, i.e., BG6PD12 and BG6PD13.

Obtaining the Complete Sequence of the Barley g6pdh Gene

Combinations of different primers, e.g., either WG6PD 7, WG6PD 9R, BG6PD 12R or BG6PD 13 plus either M13F or M13R, were used to amplify ~800 to 900-bp fragments from isolated phagemids from the barley cDNA library. The sequences of the overlapping PCR products were combined and the complete g6pdh cDNA sequence was determined. The barley cytosolic cDNA clone has an open reading frame of 509 amino acids. The estimated molecular weight is 57,864 Da and predicted pI is 6.26. The nucleotide sequence of the barley g6pdh gene shows 98% identity with three g6pdhs genes from *Triticum aestivum,* 88% with *Oryza sativa,* 77% with *Nicotiana tabacum,* and 74% with *Arabidopsis thaliana*. Its deduced amino acid sequence has 96% identity with the three g6pdhs genes of *Triticum aestivum,* 95% with *Oryza sativa,* 81% with *Nicotiana tabacum,* and 78% with *Arabidopsis thaliana* (FIG. 31).

Example 11

Development and Identification of Transformed Cereal Lines

Gene constructs used for stable transformation. Several new constructs were made in order to prepare for the generation of transgenic lines that would eliminate the antibiotic resistance genes and the plasmid backbones. This approach makes use of the maize Ds-based gene delivery system (Koprek et al., 2000). Both the barley trxh and ntr genes, previously isolated in our laboratories, were engineered into constructs in which expression of the genes was driven by barley hordein promoters and in which the expression cassette was contained within Ds inverted repeat ends. Constructs already exist that contain the Ac transposase driven by the maize ubiquitin1 and Ac transposase promoters, which can be introduced into plants that can be crossed with the Ds-containing plants.

| | |
|---|---|
| pBhssBTRX: | B-hordein promoter + B hordein signal sequence + barley thioredoxin gene |
| pBhssBNTR: | B-hordein promoter + B hordein signal sequence + barley thioredoxin reductase gene |
| pDhBTRX: | D-hordein promoter + barley thioredoxin gene |
| pDhBNTR: | D-hordein promoter + barley thioredoxin reductase gene |
| pDsBhssBTRX: | B-hordein promoter + barley hordein signal sequence + barley thioredoxin gene placed within maize transposable element Ds ends |
| pDsBhssBNTR: | B-hordein promoter + barley hordein signal sequence + barley thioredoxin reductase gene placed within maize transposable element Ds ends |

Example 12

Transgenic Barley Grain Overexpressing Thioredoxin h Shows Improved Germination Properties Homozygous lines of transgenic barley that overexpress wheat thioredoxin h (up to 22-fold) were earlier generated using a $B_1$-hordein promoter with a signal peptide sequence and found to be enriched in starch debranching enzyme (pullulanase) and alpha- and beta-amylases. Here we describe the effect of the biochemically active, overexpressed thioredoxin h on germination and seedling development. Relative to the null segregant control, the transgenic barley grain overexpressing thioredoxin h effected [i] an enhancement (up to 1 day) in the rate of germination; [ii] an increase (by 1 day) in the rate of alpha-amylase synthesis; [iii] an enhancement of proteolytic activity (55% on day 2); [iv] a 25% increase in the ratio of relative reduction of the propanol soluble proteins (hordein I fraction); and [v] an increase (up to 12%) in the amount of soluble protein. Similar to wild type lines, thioreodoxin h that was overexpressed in the transgenic grain was reduced and then degraded following imbibition. The increase in the activity of the saccharolytic and proteolytic enzymes together with the increase in reduction status of hordein led to a shift in the distribution of protein from the insoluble to the soluble fraction. These changes are discussed in relation to the faster rate of germination and the amount of overexpressed thioredoxin h.

REFERENCES

Amano M, Ogawa H, Kojima K, Kamidaira T, Suetsugu S, Yoshihama M, Satoh, T, Samejima T and Matsumoto I (1998) Identification of the major allergens in wheat flour responsible for Baker's asthma. Biochem J 330:1229–34

Batz O et al. (1998) Extensive reprogramming of primary and secondary metabolism by fungal elicitor or infection in parsley cells. *J. Biol Chem* 379: 1127–1135

Buchanan B B, Adamidi C, Lozano R M, Yee B C, Momma M, Kobrehel K, Ermel R, Frick O L 1997 Thioredoxin-linked mitigation of allergic responses to wheat. Proc Natl Acad Sci USA 94:5372–5377

Besse I and Buchanan B B 1997 Thioredoxin-linked plant and animal processes: The new generation. Bot Bull Acad Sinica 38: 1–11

Besse I and Buchanan B B 1997 Thioredoxin-linked plant and animal processes: The new generation. Bot Bull Acad Sinica 38: 1–11 Buchanan B B, Adamidi C, Lozano R M, Yee B C, Momma M, Kobrehel K, Ermel R, Frick O L 1997 Thioredoxin-linked mitigation of allergic responses to wheat. *Proc Natl Acad Sci* USA 94:5372–5377

Besse I et al. (1996) Thiocalsin: a thioredoxin-linked, substrate-specific protease dependent on calcium. Proc Natl Acad Sci USA 93: 3169–3175

Bradford, M. (1976) Anal. Biochem. 72, 248–254.

Brugidou et al. (1993) The *Nicotiana tabacum* genome encodes two cytoplasmic thioredoxin genes which are differently expressed. *Mol Gen Genet* 238: 285–293

Buchanan, B. B., Adamidi, C., Lozano, R. M., Yee, B. C., Momma, M., Kobrehel, K., Ermel, R., & Frick, O. L. (1997) Thioredoxin-linked mitigation of allergic responses to wheat. Proc. Natl. Acad. Sci. USA 94:5372–5377.

Buchanan B B (1991) Regulation of $CO_2$ assimilation in oxygenic photosynthesis: the ferredoxin/thioredoxin system. *Arch Biochem Biophys* 288: 1–9

Cho M-J, Wong J H, Marx C, Wen J, Lemaux P G and Buchanan B B (1999) Overexpression of thioredoxin h leads to enhanced activity of starch debranching enzyme (pullulanase) in barley grain. Proc Natl Acad Sci USA 96:14641–14646

Copeland L and Turner J F (1987) The regulation of glycolysis and the pentose-phosphate pathway. *The Biochemistry of Plants* 11: 107–125 del Val, G., Yee, B. C., Lozano, R. M., Buchanan, B. B., Ermel, R. W., Lee, Y. M. & Frick, O. L. (1999) Thioredoxin treatment increases digestibility and lowers allergenicity of milk J. Allerg. Clin. Immunol. 104: 690–697.

del Val G, Yee B C, Lozano R M, Buchanan B B, Ermel R W, Lee Y M, Frick O L 1999 Thioredoxin treatment increases digestibility and lowers allergenicity of milk. J Allergy Clin Immunol 103:690–6977

Dennis D T et al. (1997) Glycolysis, the pentose phosphate pathway and anaerobic respiration. *Plant Metabolism* 105–127

Ermel, R., & Frick, O. L. (1997) Thioredoxin-linked mitigation of allergic responses to wheat. Proc. Natl. Acad. Sci. USA 94:5372–5377.

Ermel, R. W., Kock, M., Griffey, S. M., Reinhart, G. A. & Frick, O. L. (1997) The atopic dog: A model for food allergy. Laboratory Animal Science 47:40–49.

Fahrendorf T et al. (1995) Stress responses in alfalfa (*Medicago sativa L.*) XIX. Transcriptional activation of oxidative pentose phosphate pathway genes at the onset of the isoflavonoid phytoalexin response. *Plant Mol Biol* 28: 885–900 Ermel, R., Kock, M., Griffey, S. M., Reinhart, G. A. & Frick, O. L. (1997) The atopic dog: A model for food allergy. Laboratory Animal Science 47:40–49.

Fickenscher K and Scheibe R (1986) Purification and properties of the cytoplasmic glucose-6-phosphate dehydrogenase from pea leaves. *Arch Biochem Biophys* 247: 393–402

Florencio F. Yee B C, Johnson T C, and Buchanan B B 1988 An NADP/thioredoxin system in leaves: purification and characterization of NADP-thioredoxin reductase and thioredoxin h from spinach. Arch Biochem Biophys 266: 496–507

Frick, O. L., Gertz, E., Wong, J. H., del Val, G., Yee, B. C., Buchanan, B. B., Petersen, W. R., Teuber, S. S. & Ross, R. (1999). New evidence strenthening the dog as a model for human allergies. Amer. Acad. Allergy Asthma. Immunol. 1999 Annual Meeting, Orlando, Fla. J. Allergy Clin. Immunol. 103: S98.

Graeve K et al. (1994) Purification, characterization, and cDNA sequence of glucose-6-phosphate dehydrogenase from potato (*Solanum tuberosum* L.). *Plant J* 5: 353–361

Herbert M et al. (1979) A survey for isoenzymes of glucose phophate isomerase, phosphoglucomutase, glucose 6-phosphate dehydrogenase and 6-phosphogluconate dehydrogenase in $C_3$, $C_4$, and Crassulacean-acid-metabolism plants and green algae. *Planta* 145: 95–104

Holmgren A (1985) Thioredoxin. *Ann Rev Biochem* 54: 237–271

Howdle P D and Blair G E 1992 Molecular biology and coeliac disease. Gut 33:573–575

Ishiwatari Y et al. (1995) Thioredoxin h is one of the major proteins in rice phloem sap. *Planta* 195: 456–463

Jacquot J-P et al. (1997) Thioredoxin: structure and function in plant cells. New Phytol 136: 543–570

Jiao J, Yee B C, Kobrehel K and Buchanan B B 1992 Effect of thioredoxin-linked reduction on the activity and stability of the Kunitz and Bowman-Birk soybean trypsin inhibitor proteins. J Agric Food Chem 40:2333–2336

Jiao J, Yee B C, Wong J H, Kobrehel K and Buchanan B B 1993 Thioredoxin-linked changes in regulatory properties of barley alpha-amylase/subtilisin inhibitor protein. Plant Physiol Biochem 31:799–804

Johnson T C et al. (1987a) Thioredoxin and NADP-thioredoxin reductase from cultured carrot cells. Planta 171: 321–331

Johnson T C, Wada K, Buchanan B B and Holmgren A 1987 Purothionin: reduction by the wheat seed thioredoxin system and potential function as a secondary thiol messenger in redox control. Plant Physiol 85:446–451

Kagnoff M F, Austin R K, Johnson, H C, Bernardin J E, Dietler M D and Kasarda, D D 1982 Celiac sprue: correlation with murine T cell responses to wheat gliadin components. J Immunol 129:2693–2697

Kim H K, Lemaux P G, Buchanan B B and Cho M-J 1999 Reduction of genotype limitation in wheat (*Triticum aestivum* L.) transformation. Congress on In Vitro Biol 35:43–A Knight J S et al. (2001) Isolation and characterization of a full-length genomic clone encoding a plastidic glucose-6-phosphate dehydrogenase from *Nicotiana tabacum*. Planta 212: 499–507

Kobrehel K, Yee B C and Buchanan B B 1991 Role of the NADP thioredoxin system in the reduction of alpha-amylase and trypsin inhibitor proteins. J Biol Chem 266: 16135–16140

Kobrehel K et al. (1992) Specific reduction of wheat storage proteins by thioredoxin h. *Plant Physiol* 99: 919–924

Levy R (1979) Glucose-6-phosphate dehydrogenases. *Adv Enzymol* 48: 97–192

Li X et al. (1995) Thioredoxin acitivity in the C terminus of *Phalaris* S protein. *Plant J* 8: 133–138

Lozano R M et al. (1994) Thioredoxin-linked reductive inactivation of venom neurotoxins. *Arch Biochem Biophy* 309: 356–362

Lozano R M, Wong J H, Yee B C, Peters A, Kobrehel K, and Buchanan B B 1996 New evidence for a role for thioredoxin h in germination and seedling development. Planta 200:100–106

Maeda K, Wakabayashi S and Matsubara H 1985 Complete amino acid sequence of alpha-amylase inhibitor in wheat kernel (0.19-inhibitor). Biochim Biophys Acta 828:213–221

Marcus F, Chamberlain S H, Chu C, Masiarz F R, Shin S, Yee B C and Buchanan B B 1991 Plant thioredoxin h: an animal-like thioredoxin occurring in multiple cell compartments. Arch Biochem Biophys 287:195–198

Nemoto Y and Sasakuma T (2000) Specific expression of glucose-6-phosphate dehydrogenase (G6PDH) gene by salt stress in wheat (*Triticum aestivum* L.). *Plant Sci* 158: 53–60

Redinbaugh M G and Campbell W H (1998) Nitrate regulation of the oxidative pentose phosphate pathway in maize (*Zea mays* L.) root plastids: induction of 6-phosphogluconate dehydrogenase activity, protein and transcript levels. *Plant Sci* 134: 129–140

Serrato A J et al. (2001) Characterization of two thioredoxins h with predominant localization in the nucleus of aleurone and scutellum cell of germinating wheat seeds. *Plant Mol Biol* 46: 361–371

Shevchenko A, Wilm M, Vorm O and Mann M 1996 Mass spectrometric sequencing of proteins from silver-stained polyacrylamide gels. Anal Chem 68:850–858

Shotwell M A, Boyer S K, Chesnut R S and Larkins B A 1990 Analysis of seed storage protein genes of oats. J Biol Chem 265:9652–9658

Srivastava D K and Anderson L E (1983) Isolation and characterization of light- and dithiothreitol-modulatable glucose-6-phosphate dehydrogenase from pea chloroplasts. *Biochem Biophys Acta* 724: 359–369

Suske G et al. (1979) NADPH thioredoxin reductase and a new thioredoxin from wheat. *Z Naturforsch* C 34: 214–221

Turner J F and Turner D H (1980) The regulation of glycolysis and the pentose phosphate pathway. The Biochemistry of Plants 2: 279–316

Varjonen E, Vainio E, Kalimo K, Juntunen-Backman K, Savolainen J 1995 Skin-prick test and RAST responses to cereals in children with atopic dermatitis. Characterization of IgE-binding components in wheat and oats by an immunoblotting method. Clin Exp Allergy 25:1100–1107

Wenderoth I et al. (1997) Identification of the cysteine residues involved in redox modification of plant plastidic glucose-6-phosphate dehydrogenase. *J Biol Chem* 272: 26985–26990

Wong J H et al. (1993) Thioredoxin and bread wheat. Cereal Chem 70: 113–114

Yano H, Wong J H, Lee Y M, Cho M-J and Buchanan B B 2001 A strategy for the identification of proteins targeted by thioredoxin. Proc Natl Acad Sci USA 98:4794–479

Stemmer WPC. 1994. DNA shuffling by random fragmentation and reassembly: In vitro recombination for molecular evolution. Proc Natl Acad Sci USA 91 : 10747–10751.

Stemmer WPC. 1994. Rapid evolution of a protein in vitro by DNA shuffling. Nature (London) 370: 389–391.

Hoseney, R. C. (1994) in "Principles of Cereal Science and Technology". American Association of Cereal Chemists. St. Paul. Minn. pp. 208–209.

Kobrehel, k., Nimbona. C., Buchanan. B. B., Bergmann, D., Wong, J. H., Yee, B. C. (1994) Thioredoxin-linked Reduction of Wheat Storage Proteins: II, Technological Consequences. In; Gluten Proteins 1993. pp. 381–392. Association of Cereal Research, Detmold, Germany.

Lehrer, S. B., Horner, W. E., Reese, G, 1996. Why are some proteins allergenic? Implications for biotechnology. Crit. Rev. Food Sci. Nutr. 36(6):553–564.

Fennema, O. R. 1996 Food Chemistry, pp. 1–15, Marcel Dekker.

Lasztity, R. 1995. Sorghum proteins. In The Chemistry of Cereal Proteins, $2_{nd}$ edition, CRC Press. New York, Chapter 7, pp. 227–248.

Sicherer, H. H. 1999 Manifestations of food allergy: Evaluation and management. Amer. Fam. Physician. 59:415–24. 429–30.

Marx, C., Lemaux, P. G. and Buchanan, B. B. 2000 The wheat grain: new research developments and arproaches to improvement. In: Black M, and Bewley, J. D. (Eds.) Seed Technology and its Biological Basis, CRC Press LLC. pp. 161–183.

Astwood, J. D., Leach, J. N., Fuchs, R. L., 1996, Stability of food allergens to digestion in vitro, Nat. Biotech. 14. 1269–1273.

Mertz E.T., Hassen, M. M., Cairns-Whittern. C., Kirleis, A. W., Tu, L., Axtell, J. D. 1984. Pepsin digestibility of proteins in sorghum and other major cereals. Proc. Natl. Acad. Sci. USA., 81:1–2.

MacLean, W. C., de Romana, L., Placko, R. P., Graham. G. G. 1981. Protein quality and digestibility of sorghum in preschool children: Balance studies and plasma free amino acids, J. Nutr, 111, 1928–1936.

Hamaker, B. R., Kirleis, A. W., Butler, L. G., Axtell, J. D., and Mertz, E. T. 1987 Improving the in vitro protein digestibility of sorghum with reducing agents. Proc. Natl. Acad. Sci. USA. 84:626–628

Wan Y. Lemaux P G. 1994. Generation of large numbers of independently transformed fertile barley plants. *Plant Physiol.* 104:37–48.

Lemaux P G. Cho M-J, Louwerse J. Williams R. Wan Y. 1996. Bombardment-mediated transformation methods for barley. Bio-Rad Bulletin 2007. pp.1–6.

Sorenson M B. Muller M. Skerritt J. Simpson D. 1996. Hordein prqmoter methylation and transcriutional activity in wild-type and mutant barley endosperm. *Mol Gen Genet* 250:750–760

Brandt A. Montembault A. Cameron-Mills V. Rasmussen S K. 1985. Primary structure of a $B_1$ hordein gene from barley. *Carlsberg Res, Commun* 50:333–345

Cho M-J. Lemaux P G. 1997. Rapid PCR amplification of chimeric products and its direct application to in vivo testing of recombinant DNA construction strategies. *Mol Biotechnol* 8:13–16

Liu S. Kriz A. 1996. Tissue-specific and ABA-regulated maize Glb1 gene expression in transgenic tobacco. *Plant Cell Rep* 16:158–162.

Cho M-J. Jiang W. Lemaux P G. 1998. Transformation of recalcitrant barley cultivars through improvement of regenerability and decreased albinism. Plant Sci 138: 229–244

Cho M-J. Choi HW. Buchanan B B. Lemaux P G. 1999a. Inheritance of tissue-specific expression of uidA in transgenic barley plants. *Theor Appl Genet:* 98: 1253–1262

Cho M-J. Jiang W. Lemaux P G. 1999b. High-frequency transformation of oat via microprojectile bombardment of seed-derived highly regenerative cultures. *Plant Sci.* 148: 9–17

Christensen A H. Quail P G. 1996. Ubiquitin promoter-based vectors for high-level expression of selectable and/9or screenable marker genes in monocotyledonous plants. *Transgenic Res* 5: 213–218

Hunter C P. 1988. Plant regeneration from microspores of barley, Hordeum vulgare. Ph.D. thesis. Wye College, University of London, Ashford Kent.

Shewry, P. R., Field, J. M., Kirkman, M. A. Faulks. A. J. and Miflin, B. J. 1980. The extraction, solubility and characterization of two groups of barley storage polypeptides, J. Exp. Bot. 31: 393–407.

Serre, L., and Lauriere, C. (1990) Specific Assay of alpha-dextrin 6-glucanohydrolast using lableled pullulan. Anal. Biochem. 186:312–315.

Furegan, L., Curioni, A., and Peruffo, A. D. B. (1994) Direct detection of pullulanese activity in electrophoretic polyacrylamide gels. Anal. Biochem. 221:200–201.

Laemmli, U. K. 1970. Cleavage of structural proteins during the assembly of the head of bacteriophage T4. Nature 227:680–685.

Mark, D. F. and Richardson. C. C. 1976. *Escherichia coil* thioredoxin: A subunit of bacteriophage T7 DNA polymerase. Proc. Natl. Acad. Sci. USA 73:780–784.

Macri, L. J., MacGregor, A. W., Schroeder, S. W., and Bazin, S. L. (1993) Detection of a Limit Dextrinase Inhibitor in Barley, J. Cereal Sci. 18:103–106.

MacGregor, A. W., Macri, L. J., Schroeder, S. W., and Bazin, S. L. (1994) Limit Dextrinase from Malted Barley: Extraction, Purification, and Characterization, Cereal Chem. 71(6):610–617.

Wong, J. H., Jiao, J.-A., Kobrehel, Buchanan, B. B. 1995. Thioredoxin-dependent deinhibition of pullulanase of barley malt by inactvation of a specific inhibitor protein. Plant Physicol. 108:67 (abstr. No. 292).

Hardie, D. C. 1975 Control of carbohydrase formation by gibberellic acid in barley endosperm. Phytochemistry 14:1719–1722.

Sissons, M. J., Lance, R. C. M., and Sparrow, D. H. B. 1993 Studies on Limit Dextrinase in Barley. 3, Limit Dextrinase in Developing Kernels, J. Cereal Sci. 17:19–24.

Sissons, M. J., Lance, R. C. M., and Wallace. W. 1994 Bound and Free Forms of Barley Limit Dextrinase. Cereal Chem. 71(5):520–521.

Cho M-J, Ha C D. Lemaux P G. 2000 . Production of transgenic tall fescue and red fescue plants by particle bombardment of mature seed-derived highly regenerative tissues. *Plant Cell Rep* 19:1084–1089

Chiu W-L. Niwa Y. Zeng W. 1996. Engineered GFP as a vital reporter in plants. *Current biology* 6: 325–330.

Dellaporta, S. (1993 ) Plant DNA miniprep and microprep. In The Maize Handbook, eds. Freeling, M. & Walbot, V. Springer, New York, pp. 522–525.

Kruger, J. E., Marchylo, B. A. and Hatcher, D. (1988) Preliminary assessment of a seguential extraction scheme for evaluating quality by reversed-phase high-performance liguid-chromatography and eletrophoretic analysis of gliadins and glutemins. Cereal Chem. 65:208–214.

Shewry, P. R., Tatham. A. S., Forde, J., Kreis, M. and Miflin, B. J. 1986. The classification and nomenclature of wheat gluten proteins: A reassessment. J. Cereal Sci. 4:97–106.

Shull, J. M., Watterson, J. J., and Kirleis, A. W. 1992 Purification and immunocytoschemical locatization of kafirins in Sorghum bicolor (L. Moench) endosnerm. Protoplasma 171:64–74.

KobreheL, K. and Buchuk, 1978, Studies on glutenin, 11. Glutenin solubilization with surfactants in water. Cereal Chem. 55:1060–1064

Sun, Z., and Henson, C. A. 1990. Degradation of native starch eranules by barley alpha-glucasidases. Plant Physiol. 94:320–327.

Bernfeld, P. (1955) Amylases □ and □, Methods Enzymol, 1:149–154.

MaCleary, B. V., Solah, V. and Gibson, T. S. (1994) Quantitative measurement of total starch in cereal flours and producs. J. Cereal Sci, 20: 51–58.

Board of Trustees (ed.). 1995. Simulated Gastric Fluid, T S., pp. 2053 in *The United States Pharmacopeia* 23. *The National Formulary* 18. United States Pharmacopeial Convention. Inc., Rockville, Md.

Smith, T. F. and Waterman, M. S. (1981) J. Mol. Biol. 147:195–197.

Needleman, S. B. and Wunsch, C. D. (1970) J. MoL. Biol. 48:443–453.

Pearson, W. R., Lipman, D. J., (1988) Proc Natl Acad Sci U.S.A. 85: 2444–8.

Higgins, D. G. and Sharp. P. M. (1988) Gene 73(1):237–44.

Higgins, D. G. and Sharp, P. M. (1989) Comput Appl Biosci. 5(2):151–3.

Corpet, F. (1998) Nucleic Acids Res, 16: 10881–10890.

Huang X, et al. (1992) Comput. Appl. Biosci. 8(2):155–65.

Pearson W R. Using the FASTA program to search protein and DNA sequence databases, Methods Mol Biol. 1994: 24:307–31.

Atschul, S. F. et al. (1994) Nat. Genet. 6(2):119–29.

Weissbach & Weissbach (1989) Methods for Plant Molecular Biology, Academic Press.

Gelvin S B. Habeck L L. vir genes influence conjugal transfer of the Ti plasmid of Agrobacterium tumefaciens. J Bacteriol. 1990 Mar; 172(3):1600–8. Related Articles, Links.

---

We claim:

1. A transgenic plant wherein at least a part of said plant comprises a recombinant nucleic acid comprising a promoter active in said part operably linked to a nucleic acid encoding a thioredoxin polypeptide wherein said promoter is a seed or grain maturation-specific promoter and said thioredoxin polypeptide comprises the amino acid sequence WCGPC or WCPPC of SEQ ID NO:1, wherein said transgenic plant exhibits an enhanced pullulanase activity.

2. The transgenic plant of claim 1 wherein said part is a seed.

3. The transgenic plant of claim 1 wherein said part is a grain.

4. The transgenic plant of claim 1 wherein said promoter is selected from the group consisting of rice glutelins, rice oryzins, rice prolamines, rice globulins, barley hordeins, wheat gliadins, wheat glutenins, maize zeins, maize glutelins, oat glutelins, sorghum kafirins, millet pennisetins, rye secalins, and maize embryo-specific globulin promoters.

5. The transgenic plant of claim 1 wherein said plant is a monocot.

6. The transgenic plait of claim 5 wherein said monocot plant is selected from the group consisting of rice, barley, maize, wheat, oat, rye, sorghum, millet, triticale, turfgrass and forage grass.

7. The transgenic plant of claim 1 wherein said thioredoxin is thioredoxin h.

8. The transgenic plant of claim 1 wherein said recombinant nucleic acid further comprises a nucleic acid encoding a signal peptide operably linked to said promoter and said nucleic acid molecule encoding a thioredoxin protein.

9. The transgenic plant of claim 8 wherein said signal peptide targets expression of the thioredoxin polypeptide to an intracellular body.

10. The transgenic plant of claim 8 wherein said promoter is selected from the group consisting of rice glutelins, rice oryzins, rice prolamines, rice globulins, barley hordeins, wheat gliadins, wheat glutenins, maize zeins, maize glutelins, oat glutelins, sorghum kafirins, millet pennisetins, rye secalins, and maize embryo-specific globulin promoters.

11. A transgenic plant comprising a recombinant thioredoxin protein wherein said recombinant thioredoxin protein includes the amino acid sequence WCGPC or WCPPC of SEQ ID NO:1 and said recombinant thioredoxin protein increases the in vivo reduction of thiol groups on one or more proteins in said transgenic plant by at least 5% compared to the in vivo reduction of said one or more proteins in said non-transgenic parent plant or plant cell, wherein said transgenic plant exhibits an enhanced pullulanase activity.

12. The plant of claim 11 wherein said proteins are selected from the group consisting of members of the alpha-amylase inhibitor, the alpha-amylase/trypsin inhibitor and the sulfur-rich gliadin families of proteins.

13. The transgenic plant of claim 11 wherein said plant is monocot.

14. The transgenic plant of claim 11 wherein said plant is a dicot.

15. The transgenic plant of claim 13 wherein said moncot is selected from the group consisting of maize, rice, wheat, sorghum and barley.

* * * * *